United States Patent
Crain et al.

(10) Patent No.: US 6,765,010 B2
(45) Date of Patent: Jul. 20, 2004

(54) COMPOSITIONS AND METHODS FOR ENHANCING ANALGESIC POTENCY OF TRAMADOL AND ATTENUATING ITS ADVERSE SIDE EFFECTS

(75) Inventors: Stanley M. Crain, State College, PA (US); Ke-Fei Shen, Flushing, NY (US); Barry Sherman, Hillsborough, CA (US); Mary Remien, San Francisco, CA (US); Remi Barbier, San Francisco, CA (US); Nadav Friedmann, Lafayette, CA (US)

(73) Assignees: Pain Therapeutics, Inc., South San Francisco, CA (US); Albert Einstein College of Medicine of Yeshiva University, Bronx, NY (US)

( * ) Notice: Subject to any disclaimer, the term of this patent is extended or adjusted under 35 U.S.C. 154(b) by 0 days.

(21) Appl. No.: 10/095,802

(22) Filed: Mar. 12, 2002

(65) Prior Publication Data

US 2003/0148941 A1 Aug. 7, 2003

Related U.S. Application Data

(63) Continuation of application No. 09/929,976, filed on Aug. 14, 2001, now abandoned, which is a continuation of application No. 09/756,331, filed on Jan. 8, 2001, now abandoned, which is a continuation of application No. 09/566,071, filed on May 5, 2000, now abandoned, which is a continuation-in-part of application No. 09/306,164, filed on May 6, 1999, now abandoned.

(51) Int. Cl.[7] .............................................. A61R 31/14
(52) U.S. Cl. ...................................................... 514/282
(58) Field of Search ......................................... 514/282

(56) References Cited

U.S. PATENT DOCUMENTS 5,512,578 A * 4/1996 Crain et al. .................. 514/282
5,672,360 A * 9/1997 Sackler et al. .............. 424/490

* cited by examiner

Primary Examiner—James H. Reamer
(74) Attorney, Agent, or Firm—McAndrews, Held & Malloy, Ltd.

(57) ABSTRACT

The invention generally relates to compositions and methods with tramadol and an opioid antagonist to enhance analgesic potency and/or attenuate one or more adverse effects of tramadol, including adverse side effect(s) in humans such as nausea, vomiting, dizziness, headache, sedation (somnolence) or pruritis. This invention relates to compositions and methods for selectively enhancing the analgesic potency of tramadol and simultaneously attenuating anti-analgesia, hyperalgesia, hyperexcitability, physical dependence and/or tolerance effects associated with the administration of tramadol. The methods of the present invention comprise administering to a subject an analgesic or subanalgesic amount of tramadol and an amount of excitatory opioid receptor antagonist such as naltrexone or nalmefene effective to enhance the analgesic potency of tramadol and attenuate the anti-analgesia, hyperalgesia, hyperexcitability, physical dependence and/or tolerance effects of tramadol.

76 Claims, 24 Drawing Sheets

Morphine 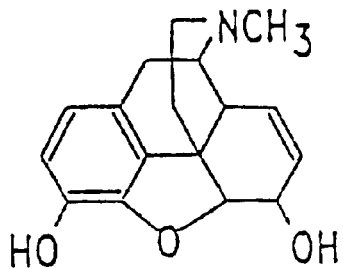
Tramadol 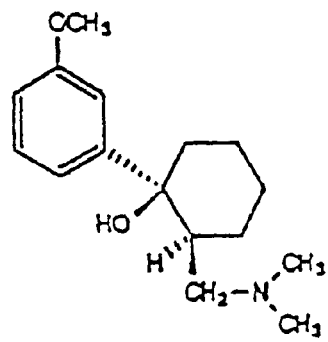
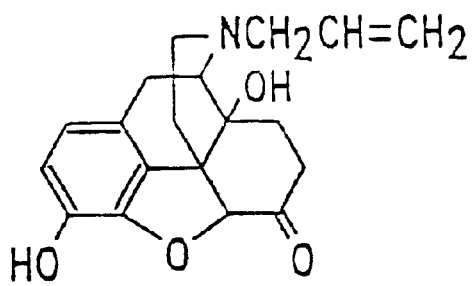
Naloxone
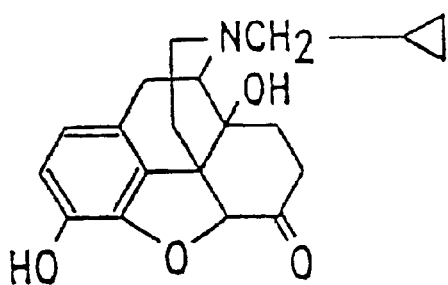
Naltrexone (R=O)
Nalmefene (R=$CH_2$)
FIG. 1

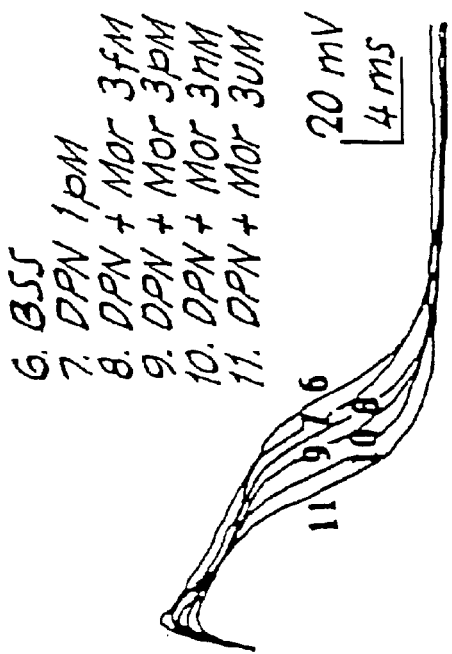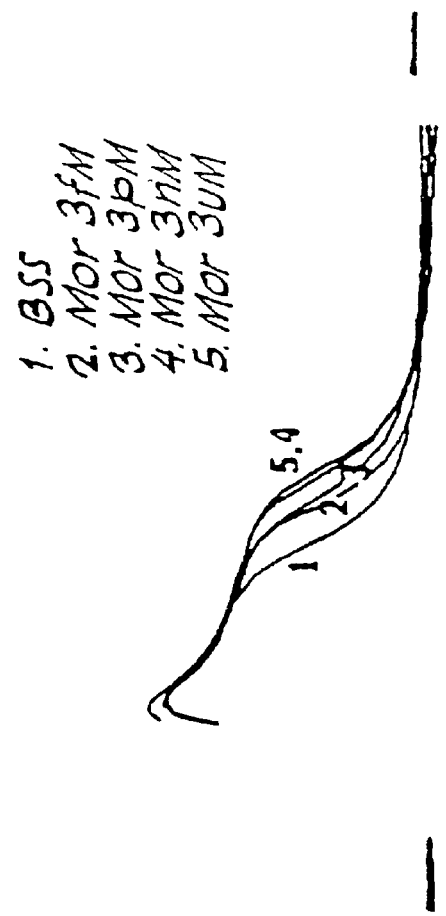
FIG. 4A

| Acute Test | Alteration of Action Potential Duration (APD) | | | |
|---|---|---|---|---|
| | (APD shortening: ↓  ;APD prolongation: ↑  ;No APD change: 0) | | | |
| | Naive DRG Neurons | | Chronic Morphine-Treated Neurons (1uM; >1wk) | Chronic Co-treatment with Mor + Antag. at Excit. Op. Rec. (pM) |
| | Control BSS | BSS + Antag. at Excit.Op.Rec. (pM) | After Washout with BSS | |
| 1 – 10 uM morphine | ↓ (inhibitory) ("analgesia") | ↓↓ | ↑ ("tolerance") | ↓ |
| pM – nM morphine | ↑ ("excitatory antianalgesia") | ↓ (unmasking of inhibitory effects) | ↓ | ↓ |
| ~ fM morphine or dyn A-(1-13) | 0 | 0 | ↑ (excitatory supersensitivity) | 0 |
| nM naloxone | 0 | 0 | ↑ ("dependence") ("withdrawal effect") | 0 |

FIG. 6

Figure 20: Mean Hourly Pain Intensity Difference Scores by Treatment. Intent-to-Treat Subjects Figure 21: Mean Hourly Visual Analog Scale Pain Intensity Difference Scores by Treatment. Intent-to-Treat Subjects

FIGURE 22

|  | Placebo | T 50 mg | T/NTX 0.01 mg | T/NTX 0.1 mg | T/NTX 1 mg |
|---|---|---|---|---|---|
| Patients Studied | 51 | 50 | 51 | 52 | 50 |
| Nausea | 9 17.6% | 20 40% | 11 21.6% | 17 32.7% | 24 48% |
| Vomiting | 2 3.9% | 10 20% | 7 13.7% | 8 15.4% | 12 24% |
| Dizziness | 9 17.6% | 15 30% | 8 15.7% | 12 23.1% | 17 34% |
| Headache | 27 52.9% | 28 56% | 26 51.0% | 28 53.8% | 29 58% |
| Sedation | 22 43.1% | 28 56% | 25 49.0% | 22 42.3% | 25 50% |
| Pruritus | 1 2.0% | 2 4% | 0 | 0 | 3 6% |

COMPOSITIONS AND METHODS FOR ENHANCING ANALGESIC POTENCY OF TRAMADOL AND ATTENUATING ITS ADVERSE SIDE EFFECTS

CROSS-REFERENCE TO RELATED APPLICATION

This is a Continuation of U.S. application Ser. No. 09/929,976 filed Aug. 14, 2001 now abandoned, which is a continuation of U.S. application Ser. No. 09/756,331 filed Jan. 8, 2001 now abandoned, which is a continuation of U.S. application Ser. No. 09/566,071 filed May 5, 2000 now abandoned, which is a CIP of U.S. application Ser. No. 09/306,164 filed May 6, 1999 now abandoned.

BACKGROUND OF THE INVENTION

Morphine or other bimodally-acting opioid agonists are administered to relieve severe pain due to the fact that they have analgesic effects mediated by their activation of inhibitory opioid receptors on nociceptive neurons (see North, Trends Neurosci., Vol. 9, pp. 114–117 (1986) and Crain and Shen, Trends Pharmacol. Sci., Vol. 11, pp. 77–81 (1990)). However, morphine and other bimodally-acting opioid agonists also activate opioid excitatory receptors on nociceptive neurons, which attenuate the analgesic potency of the opioids and result in the development of physical dependence and increased tolerance (see Shen and Crain, Brain Res., Vol. 597, pp. 74–83 (1992)), as well as hyperexcitability, hyperalgesia and other undesirable (excitatory) side effects. As a result, a long-standing need has existed to develop a method of both enhancing the analgesic (inhibitory) effects of bimodally-acting opioid agonists and blocking or preventing undesirable (excitatory) side effects caused by such opioid agonists.

Tramadol is an orally active, clinically effective, centrally acting analgene compound with opioid and non-opioid activity. This synthetic analgesic has a novel mechanism of action involving a complementary and synergistic interaction between inhibition of neuronal monamine uptake and weak affinity for opioid receptors (Raffa et al., Rev. Contemp. Pharmacother. 6:485–497 (1995)). Tramadol is generally well tolerated, with dizziness, nausea, constipation, headache, somnolence (sedation), vomiting, pruritis, CNS stimulation, sezures, asthenia, dyspepsia, diarrhea, dry mouth and/or sweating as adverse side effects. Respiratory depression is uncommon (Lee et al., Drugs 46: 313–340 (1993); Vickers et al., Anaesthesia 47: 291–296 (1992)). Tramadol is marketed in the United States as ULTRAM®. Data from a double-blind, crossover study suggest that oral tramadol 120 mg is equipotent to oral morphine 30 mg (Wilder et al., Ann. Oncol. 5: 141–146 (1994)). A need thus exists for compositions and methods that could enhance the analgesic potency of tramadol and/or block or prevent its adverse side effects, particularly its principal adverse effects in humans.

SUMMARY OF THE INVENTION

The present invention is directed to compositions and methods for enhancing analgesic potency of tramedol and/or attenuating (e.g. reducing, blocking, inhibiting or preventing) its adverse effects, particularly its adverse side effects in humans. Principle adverse side effects of tramadol in humans include dizziness, nausea, constipation, headache, somnolence (sedation), vomiting, pruritis, CNS stimulation, seizures, asthenia, dyspepsia, diarrhea, dry mouth and/or sweating.

The present invention is directed to a method for selectively enhancing the analgesic potency and simultaneously attenuating anti-analgesia, hyperalgesia, hyperexcitability, physical dependence and/or tolerance effects associated with the administration of the tramadol. The method comprises administering to a subject an analgesic or sub-analgesic amount of tramadol and an amount of an excitatory opioid receptor antagonist effective to enhance the analgesic potency of the tramadol and attenuate the anti-analgesia, hyperalgesia, hyperexcitability, physical dependence and/or tolerance effects of the tramadol.

The present invention also provides a method for treating pain in a subject comprising administering to the subject an analgesic or sub-analgesic amount of tramadol and an amount of an excitatory opioid receptor antagonist effective to enhance the analgesic potency of the tramadol and attenuate anti-analgesia, hyperalgesia, hyperexcitability, physical dependence and/or tolerance effects of the tramadol.

The present invention provides a composition comprising an analgesic or sub-analgesic amount of a bimodally-acting opioid agonist and an amount of an excitatory opioid receptor antagonist effective to enhance the analgesic potency of the bimodally-acting opioid agonist and attenuate the anti-analgesia, hyperalgesia, hyperexcitability, physical dependence and/or tolerance effects of the bimodally-acting opioid agonist in a subject administered the composition.

The present invention provides a method for enhancing the potency of tramadol in a human subject by administering to the human subject an analgesic or subanalgesic amount of tramadol and an amount of an opioid antagonist effective to enhance the analgesic potency of the tramadol. Preferred opioid antagonists include naltrexone, naloxone, or nalmefene.

The present invention also provides a method for attenuating an adverse side effect associated with the administration of tramadol to a human subject by administering to the human subject an analgesic or subanalgesic amount of tramadol and an amount of an opioid antagonist effective to attenuate the adverse side effect. Adverse side effects include, but are not limited to, nausea, vomiting, dizziness, headache, somnolence (sedation) or pruritis. Analgesic potency of the agonist may be maintained while one or more side effects are attenuated, without increasing or decreasing the cumulative daily dose of agonist.

The present invention further provides a method for treating pain in a human subject by administering to the human subject an analgesic or subanalgesic amount of tramadol and an amount of an opioid antagonist effective to enhance the analgesic potency of tramadol, as well as a method for treating pain with tramadol and attenuating an adverse side effect of tramadol in a human subject by administering to the human subject an analgesic or subanalgesic amount of tramadol and an amount of an opioid antagonist effective to attenuate the adverse side effect.

The present invention provides a composition of an analgesic or subanalgesic amount of tramadol and an amount of an opioid antagonist effective to enhance the analgesic potency of tramadol. The present invention also provides a composition of an analgesic or subanalgesic amount of tramadol and an amount of an opioid antagonist effective to attenuate an adverse side effect of tramadol.

Compositions and methods of the present invention thus solve the problem of a less than desired analgesic potency and/or adverse side effects associated with tramadol administration in humans.

BRIEF DESCRIPTION OF THE FIGURES

FIG. 1 represents the structural formulae of the bimodally-acting opioid agonist morphine and tramadol, and the excitatory opioid receptor antagonists naloxone, naltrexone and nalmefene. Naltrexone is the N-cyclopropylmethyl congener of naloxone. Nalmefene is the 6-methylene derivative of naltrexone (Hahn, E. F., et al. *J. Med. Chem.* 18: 259–262 (1975)).

FIGS. 4A and 4B represent the selective blocking of excitatory APD-prolonging effects elicited by morphine in DRG neurons by co-administration of a low (pM) concentration of diprenorphine, thereby unmasking potent dose-dependent inhibitory APD shortening by low concentrations of morphine (comparable to the inhibitory potency of etorphine). In contrast, co-treatment with a higher (nM) concentration of DPN blocks both inhibitory as well as excitatory opioid effects.

FIG. 6 represents the assay procedure used to demonstrate that selective antagonists at excitatory opioid receptors prevents development of tolerance/dependence during chronic co-treatment of DRG neurons with morphine.

FIG. 11, curve ■). Tramadol 50 mg/kg (x) was used as the control.

FIG. 22 represents a summary of adverse side effects attenuated by administration of tramadol/antagonists (NTX) combinations in human subjects according to the invention.

DETAILED DESCRIPTION OF THE INVENTION

Figure 2A:
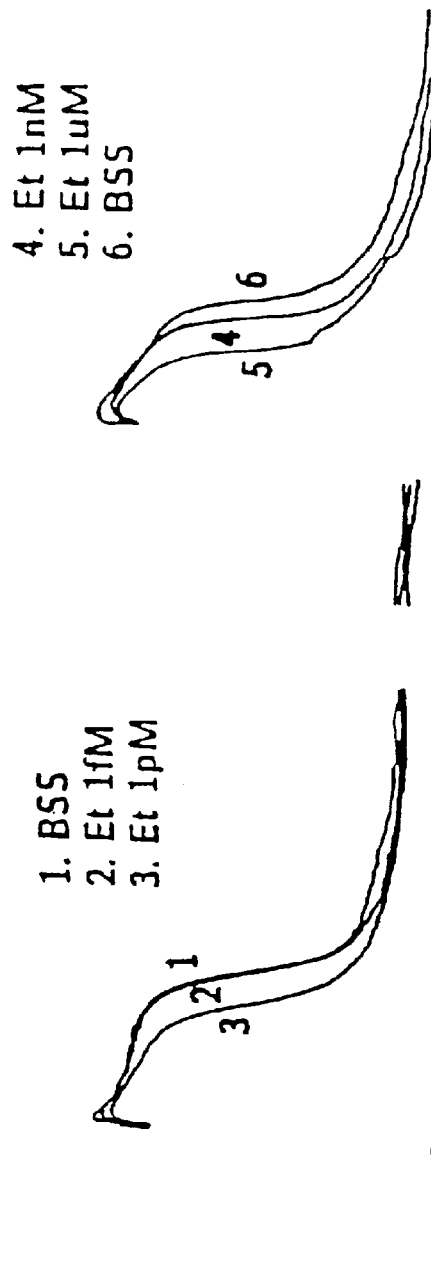
FIG. 2 represents the direct inhibitory effect of etorphine on the action potential duration (APD) of nociceptive types of sensory neurons and the blocking effect of etorphine on the excitatory response (APD prolongation) elicited by morphine. Acute application of low (pM-nM) concentrations of etorphine to naive dorsal root ganglion (DRG) neurons elicits dose-dependent, naloxone-reversible inhibitory shortening of the APD. In contrast, morphine and other bimodally-acting opioid agonists elicit excitatory APD prolongation at these low concentrations which can be selectively blocked by <pM levels of etorphine, resulting in unmasking of potent inhibitory APD shortening by nM morphine.

The present invention is directed to novel compositions and methods with tramadol and opioid antagonists. Combinations of tramadol and an opioid antagonist, such as naltrexone, were unexpectedly efficacious in enhancing the analgesic potency of tramadol and/or attenuating its side effects in humans. For example, potency may be enhanced at least about 2-fold by combination of tramadol and an opioid antagonist, so that the potency of a 50 mg dose of tramadol with a low dose (e.g., 0.01 mg) of antagonist (e.g., naltrexone) was comparable to the potency of a 100 mg dose of tramadol alone.

Tramadol hydrochloride (tramadol) (1RS,2RS)-2 [(dimethylamino)-methyl]-1-(3-methoxyphenyl)-cyclohexanol HCL (FIG. 1) is an orally active, clinically effective, centrally acting analgesic compound with opioid and non-opioid activity. This synthetic analgesic has a novel mechanism of action involving a complementary and synergistic interaction between inhibition of neuronal monamine reuptake and weak affinity for opioid receptors. This duality of action has prompted the classification of tramadol as a non-traditional centrally-acting analgesic. In a study in human volunteers, the attenuation by administration of naloxone was reported to be about 30–35%, demonstrating that the non-opioid mechanism plays a significant role in tramadol's analgesic action in humans. The nature of the non-opioid component of tramadol-induced analgesia in human volunteers has been examined. The α2-adrenoceptor antagonist yohimbine significantly reduced tramadol-induced analgesia (≧89%). The addition of naloxone removed the residual analgesic effect. Since tramadol does not have affinity for α2-adrenoreceptors, the approximately 90% reduction of tramadol-induced analgesia that was observed in human volunteers with yohimbine probably reflects the ability of tramadol to inhibit neuronal reuptake of norepinephrine.

As used herein, the term "opioid" refers to compounds which bind to specific opioid receptors and have agonist (activation) or antagonist (inactivation) effects at these receptors, such as opioid alkaloids, including the agonist morphine and the antagonist naloxone, and opioid peptides, including enkephalins, dynorphins and endorphins. The term "opiate" refers to drugs derived from opium or related analogs.

"Bimodally-acting opioid agonists" are opioid agonists that bind to and activate both inhibitory and excitatory opioid receptors on nociceptive neurons which mediate pain. Activation of inhibitory receptors by said agonists causes analgesia. Activation of excitatory receptors by said agonists results in anti-analgesia, hyperexcitability, hyperalgesia, as well as development of physical dependence, tolerance and other undesirable side effects.

Bimodally-acting opioid agonists suitable for use in the present invention may be identified by measuring the opioid's effect on the action potential duration (APD) of dorsal root ganglion (DRG) neurons in tissue cultures. In this regard, bimodally-acting opioid agonists are compounds which elicit prolongation of the APD of DRG neurons at pM-nM concentrations (i.e., excitatory effects), and shortening of the APD of DRG neurons at $\mu$M concentrations (i.e., inhibitory effects). Suitable bimodally-acting opioid agonists include but are not limited to morphine, codeine, fentanyl analogs, pentazocine, buprenorphine, methadone, tramadol, enkephalins, dynorphins, endorphins and similarly acting opioid alkaloids and opioid peptides. For purposes of treating pain, morphine, codeine and tramadol are preferred.

"Excitatory opioid receptor antagonists" are opioids which bind to and act as antagonists to excitatory but not inhibitory opioid receptors on nociceptive neurons which mediate pain. That is, excitatory opioid receptor antagonists are compounds which bind to excitatory opioid receptors and selectively block excitatory opioid receptor functions of nociceptive types of DRG neurons at 1,000 to 10,000-fold lower concentrations than are required to block inhibitory opioid receptor functions in these neurons.

Excitatory opioid receptor antagonists suitable for use in the present invention may also be identified by measuring their effect on the action potential duration (APD) of dorsal root ganglion (DRG) neurons in tissue cultures. In this regard, excitatory opioid receptor antagonists are compounds which selectively block prolongation of the APD of DRG neurons (i.e., excitatory effects) but not the shortening of the APD of DRG neurons (i.e., inhibitory effects) elicited by a bimodally-acting opioid receptor agonist. Suitable excitatory opioid receptor antagonists of the invention include nalmefene, naltrexone, naloxone, etorphine and dihydroetorphine, as well as similarly acting opioid alkaloids and opioid peptides. Preferred excitatory opioid receptor antagonists are nalmefene and naltrexone because of their longer duration of action as compared to naloxone and their greater bioavailability after oral administration.

The bimodally-acting opioid agonists and the excitatory opioid receptor antagonists for use in the present invention may in the form of free bases or pharmaceutically acceptable acid addition salts thereof. Examples of suitable acids for salt formation include but are not limited to methanesulfonic, sulfuric, hydrochloric, glucuronic, phosphoric, acetic, citric, lactic, ascorbic, maleic, and the like.

The excitatory opioid receptor antagonist alone, or in combination with the bimodally-acting opioid agonist, may be administered to a human or animal subject by known procedures including but not limited to oral, sublingual, intramuscular, subcutaneous, intravenous, and transdermal modes of administration. When a combination of these compounds are administered, they may be administered together in the same composition, or may be administered in separate compositions. If the bimodally-acting opioid agonist and the excitatory opioid receptor antagonist are administered in separate compositions, they may be administered by similar or different modes of administration, and may be administered simultaneously with one another, or shortly before or after the other.

The bimodally-acting opioid agonists and the excitatory opioid receptor antagonists may be formulated in compositions with a pharmaceutically acceptable carrier. The carrier must be "acceptable" in the sense of being compatible with the other ingredients of the formulation and not deleterious to the recipient thereof. Examples of suitable pharmaceutical carriers include lactose, sucrose, starch, talc, magnesium stearate, crystalline cellulose, methyl cellulose, carboxymethyl cellulose, glycerin, sodium alginate, gum arabic, powders, saline, water, among others. The formulations may conveniently be presented in unit dosage and may be prepared by methods well-known in the pharmaceutical art, by bringing the active compound into association with a carrier or diluent, as a suspension or solution, and optionally one or more accessory ingredients, e.g. buffers, flavoring agents, surface active agents, and the like. The choice of carrier will depend upon the route of administration.

For oral and sublingual administration, the formulation may be presented as capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate.

For intravenous, intramuscular, or subcutaneous administration, the compounds may be combined with a sterile aqueous solution which is preferably isotonic with the blood of the recipient. Such formulations may be prepared by dissolving solid active ingredient in water containing physiologically compatible substances such as sodium chloride, glycine, and the like, and having a buffered pH compatible with physiological conditions to produce an aqueous solution, and rendering said solution sterile. The formulations may be present in unit or multi-dose containers such as sealed ampoules or vials.

For transdermal administration, the compounds may be combined with skin penetration enhancers such as propylene glycol, polyethylene glycol, isopropanol, ethanol, oleic acid, N-methylpyrrolidone, and the like, which increase the permeability of the skin to the compounds, and permit the compounds to penetrate through the skin and into the bloodstream. The compound/enhancer compositions also may be combined additionally with a polymeric substance such as ethylcellulose, hydroxypropyl cellulose, ethylene/vinylacetate, polyvinyl pyrrolidone, and the like, to provide the composition in gel form, which can be dissolved in solvent such as methylene chloride, evaporated to the desired viscosity, and then applied to backing material to provide a patch.

When the excitatory opioid receptor antagonist is used in combination with the bimodally-acting opioid agonist, the amount of the bimodally-acting opioid agonist administered may be an analgesic or sub-analgesic amount. As used herein, an "analgesic" amount is amount of the bimodally-acting opioid agonist which causes analgesia in a subject administered the bimodally-acting opioid agonist alone, and includes standard doses of the agonist which are typically administered to cause analgesia (e.g. mg doses). A "sub-analgesic" amount is an amount which does not cause analgesia in a subject administered the bimodally-acting opioid agonist alone, but when used in combination with the excitatory opioid receptor antagonist, results in analgesia. The amount of the excitatory opioid receptor antagonist is an amount effective to enhance the analgesic potency of the bimodally-acting opioid agonist and attenuate the anti-analgesia, hyperalgesia, hyperexcitability, physical dependence and/or tolerance effects of the bimodally-acting opioid agonist. Based on studies of nociceptive DRG neurons in culture and in vivo mouse studies, the amount of the excitatory opioid receptor administered may be between about 1000 and about 10,000,000 fold less, and preferably between about 10,000 and 1,000,000 fold less than the amount of the bimodally-acting opioid agonist administered. The optimum amounts of the, bimodally-acting opioid agonist and the excitatory opioid receptor antagonist administered will of course depend upon the particular agonist and antagonist used, the carrier chosen, the route of administration, and the pharmacokinetic properties of the subject being treated.

When the excitatory opioid receptor antagonist is administered alone (i.e., for treating an opioid addict), the amount of the excitatory opioid receptor antagonist administered is an amount effective to attenuate physical dependence caused by a bimodally-acting opioid agonist such as morphine and enhance the analgesic potency of the bimodally-acting opioid agonist. That is, the amount of the excitatory opioid receptor antagonist is an amount which blocks the excitatory effects (i.e., physical dependence) of the bimodally-acting opioid agonist without blocking the inhibitory effects (i.e., analgesic effects) of the bimodally-acting opioid agonist. This amount is readily determinable by one skilled in the art.

The present invention is described in the following examples which are set forth to aid in the understanding of the invention, and should not be construed to limit in any way the invention as defined in the claims which follow thereafter.

EXAMPLE 1

Etorphine and Dihydroetorphine Act as Potent Selective Antagonists at Excitatory Opioid Receptors on DRG Neurons Thereby Enhancing Inhibitory Effects of Bimodally-Acting Opioid Agonists Methods: The experiments described herein were carried out on dorsal root ganglion (DRG) neurons in organotypic explants of spinal cord with attached DRGs from 13-day-old fetal mice after 3 to 5 weeks of maturation in culture. The DRG-cord explants were grown on collagen-coated coverslips in Maximow depression-slide chambers. The culture medium consisted of 65% Eagle's minimal essential medium, 25% fetal bovine serum, 10% chick embryo extract, 2 mM glutamine and 0.6% glucose. During the first week in vitro the medium was supplemented with nerve growth factor (NGF-7S) at a concentration of about 0.5 μg/ml, to enhance survival and growth of the fetal mouse DRG neurons.

In order to perform electrophysiologic procedures, the culture coverslip was transferred to a recording chamber containing about 1 ml of Hanks' balanced salt solution (BSS). The bath solution was supplemented with 4 mM $Ca^{2+}$ and 5 mM $Ba^{2+}$+(i.e., Ca, Ba/BSS) to provide a prominent baseline response for pharmacological tests. Intracellular recordings were obtained from DRG perikarya selected at random within the ganglion. The micropipettes were filled with 3 M KCl (having a resistance of about 60-100 megohms) and were connected via a chloridized silver wire to a neutralized input capacity preamplifier (Axoclamp 2A) for current-clamp recording. After impalement of a DRG neuron, brief (2 msec) depolarizing current pulses were applied via the recording electrode to evoke action potentials at a frequency of 0.1 Hz. Recordings of the action potentials were stored on a floppy disc using the P-clamp program (Axon Instruments) in a microcomputer (IBM AT-compatible).

Drugs were applied by bath perfusion with a manually operated, push-pull syringe system at a rate of 2–3 ml/min. Perfusion of test agents was begun after the action potential and the resting potential of the neuron reached a stable condition during >4 minute pretest periods in control Ca, Ba/BSS. Opioid-mediated changes in the APD were considered significant if the APD alteration was >10% of the control value for the same cell and was maintained for the entire test period of 5 minutes. The APD was measured as the time between the peak of the APD and the inflection point on the repolarizing phase. The following drugs were used in this and the following Examples: etorphine, diprenorphine and morphine (gifts from Dr. Eric Simon); dihydroetorphine (gift from Dr. B.-Y. Qin, China and United Biomedical, Inc.); naloxone (Endo Labs); naltrexone, DADLE, dynorphin and other opioid peptides (Sigma).

Opioid alkaloids and peptides were generally prepared as 1 mM solutions in $H_2O$ and then carefully diluted with BSS to the desired concentrations, systematically discarding pipette tips after each successive 1–10 or 1–100 dilution step to ensure accuracy of extremely low (fM-pM) concentrations.

Results: Intracellular recordings were made from small- and medium-size DRG neuron perikarya (about 10–30 μm in diameter) which generate relatively long APDs (greater than 3 msec in Ca/Ba BSS) and which show characteristic responsiveness to opioid agonists and other properties of primary afferent nociceptive neurons as occur in vivo. Acute application of selective inhibitory opioid receptor agonists, e.g., etorphine, to these DRG neurons shortens the APD in 80–90% of the cells tested, whereas low concentrations of bimodally-acting (excitatory/inhibitory) opioids, e.g., morphine, dynorphin, enkephalins, prolong the APD in these same cells. Relatively small numbers of large DRG neurons (about 30–50 μm in diameter) survive in DRG-cord explants (about 10–20%) and show much shorter APDs (about 1–2 msec in Ca/Ba BSS), with no clear-cut inflection or "hump" on the falling phase of the spike. The APD of these large DRG neurons is not altered by exogenous opioids.

The opioid responsiveness of DRG neurons was analyzed by measuring the opioid-induced alterations in the APD of DRG perikarya. A total of 64 DRG neurons (from 23 DRG-cord explants) were studied for sensitivity to progressive increases in the concentration of etorphine (n=30) or dihydroetorphine (n=38). Etorphine rapidly and dose-dependently shortened the APD in progressively larger fractions of DRG cells at concentrations from 1 fM (30% of cells; n=26) to 1 μM (80% of cells; n=16) (see FIGS. 2 and 3).

Figure 2B:
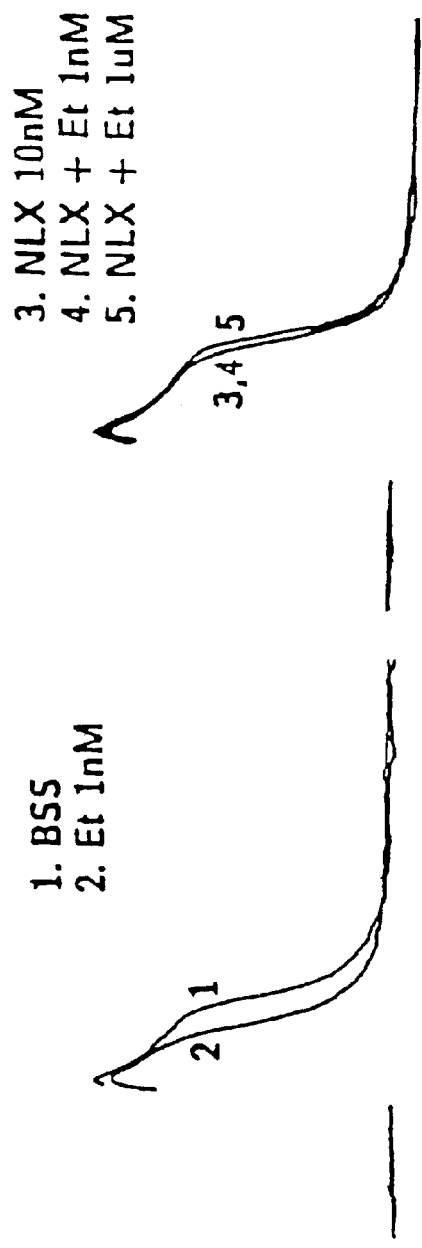

FIG. 2 shows that acute application of low (pM-nM) concentrations of etorphine to naive DRG neurons elicits dose-dependent, naloxone-reversible inhibitory shortening of the action potential duration (APD). In contrast, dynorphin (and many other bimodally-acting opioid agonists, e.g., morphine, DADLE) elicit excitatory APD prolongation at these low concentrations (see FIG. 3), which can be selectively blocked by <pM levels of etorphine, as well as by diprenorphine or naltrexone (see FIGS. 4 and 5). FIG. 2A record 1 shows the action potential (AP) generated by a DRG neuron in balanced salt solution containing 5 mM $Ca^{2+}$ and 5 mM $Ba^{2+}$ (BSS). AP response in this record (and in all records below) is evoked by a brief (2 msec) intracellular depolarizing current pulse. FIG. 2A records 2–5 show that APD is not altered by bath perfusion with 1 fM etorphine (Et) but is progressively shortened in 1 pM, 1 nM and 1 μM concentrations (5 minute test periods). FIG. 2A record 6 shows that APD returns to control value after transfer to BSS (9 minute test). FIG. 2B records 1 and 2 show that APD of another DRG neuron is shortened by application of 1 nM etorphine (2 minute test). FIG. 2B record 3 shows that APD returns to control value after transfer to 10 nM naloxone (NLX). FIG. 2B records 4 and 5 show that APD is no longer shortened by 1 nM or even 1 μM etorphine when co-perfused with 10 nM naloxone (5 minute test periods).

Figure 2C:
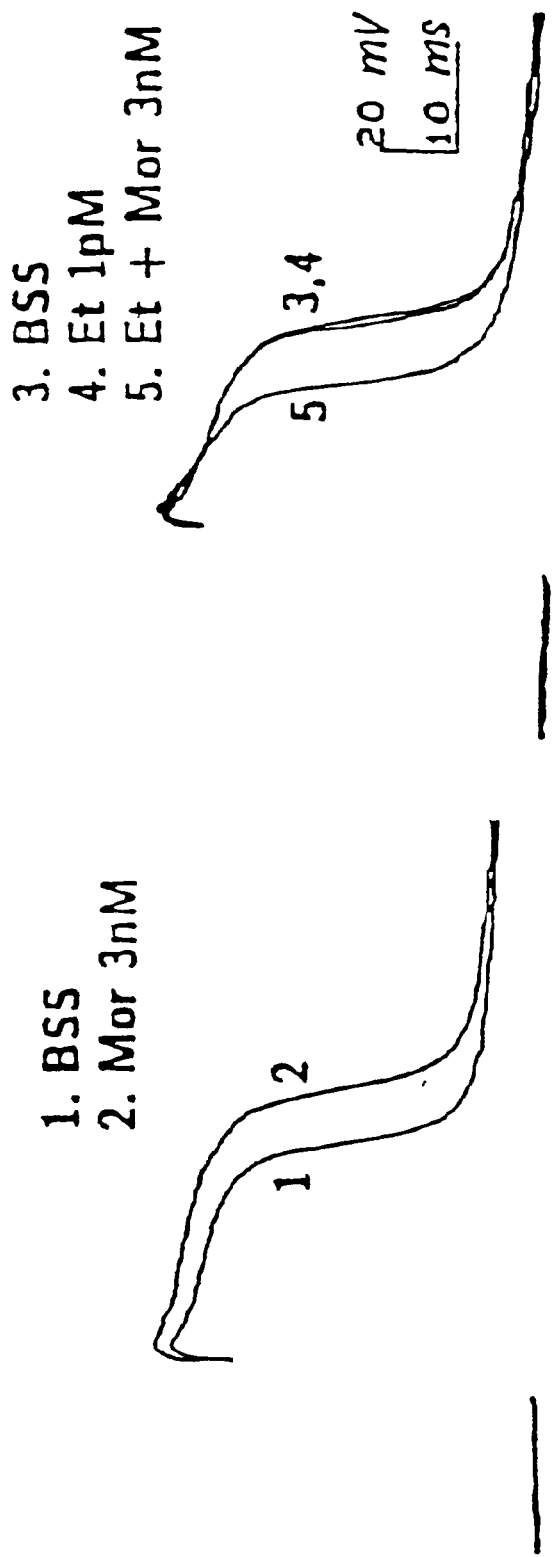

FIG. 2C records 1 and 2 show that APD of another DRG neuron is prolonged by application of 3 nM morphine. FIG. 2C record 3 shows that APD returns to control value by 5 minutes after washout. FIG. 2C record 4 shows that application of 1 pM etorphine does not alter the APD. FIG. 2C record 5 shows that APD is no longer prolonged by 3 nM morphine when co-perfused with 1 pM etorphine and instead is markedly shortened to a degree which would require a much higher morphine concentration in the absence of etorphine. Similar results were obtained by pretreatment with 1 pM diprenorphine (see FIG. 4), with 1 pM naltrexone (FIG. 5) or 1 pM naloxone. Records in this and subsequent Figures are from DRG neurons in organotypic DRG-spinal cord explants maintained for 3–4 weeks in culture.

Figure 3:
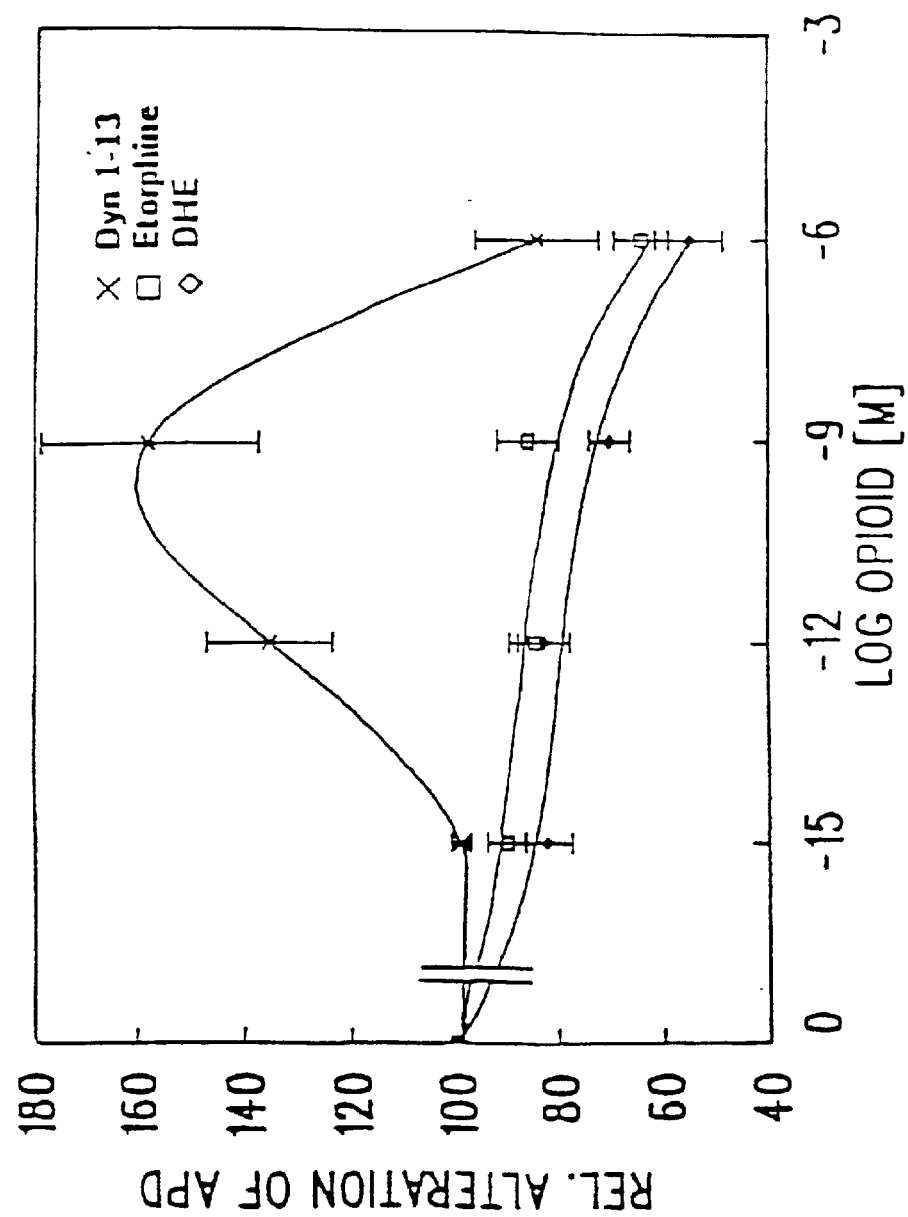
FIG. 3 represents dose-response curves of different opioids, showing that etorphine and dihydroetorphine elicit only inhibitory dose-dependent shortening of the APD of DRG neurons at all concentrations tested (fM-$\mu$M). In contrast, dynorphin A (as well as morphine and other bimodally-acting opioids) elicit dose-dependent excitatory APD prolongation at low concentrations (fM-nM) and requires much higher concentrations (about 0.1–1 $\mu$M) to shorten the APD, thereby resulting in a bell-shaped, dose-response curve.

FIG. 3 shows dose-response curves demonstrating that etorphine (Et) (□) and dihydroetorphine (DHE) (◇) elicit only inhibitory dose-dependent shortening of the APD of DRG neurons at all concentrations tested (fM-μM). In contrast, dynorphin A (1-13) (Dyn) (X) (as well as morphine and other bimodally-acting opioids) elicits dose-dependent excitatory APD prolongation at low concentrations (fM-nM) and generally requires much higher concentrations (about 0.1–1 μM) to shorten the APD, thereby resulting in a bell-shaped dose-response curve. Data were obtained from 11 neurons for the etorphine tests, 13 for the DHE tests and 35 for the dynorphin tests; 5, 8 and 9 neurons were tested (as in FIG. 2) with all four concentrations of etorphine, DHE and dynorphin, respectively (from fM to μM). For sequential dose-response data on the same neuron, the lowest concentrations (e.g., 1 fM) were applied first.

Dihydroetorphine was even more effective (n=38; FIG. 3). Naloxone (10 nM) prevented the etorphine- and dihydroetorphine-induced APD shortening which was previously elicited in the same cells (n=12; FIG. 2B). These potent inhibitory effects of etorphine and dihydroetorphine on DRG neurons at low concentrations are in sharp contrast to the excitatory APD-prolonging effects observed in similar tests with morphine and a wide variety of mu, delta and kappa opioids. None of the DRG neurons tested with different concentrations of etorphine or dihydroetorphine showed prominent APD prolongation.

The absence of excitatory APD-prolonging effects of etorphine and dihydroetorphine on DRG neurons could be due to low binding affinity of these opioid agonists to excitatory opioid receptors. Alternatively, these opioids might bind strongly to excitatory receptors, but fail to activate them, thereby functioning as antagonists. In order to distinguish between these two modes of action, DRG neurons were pretreated with etorphine at low concentrations (fM-pM) that evoked little or no alteration of the APD. Subsequent addition of nM concentrations of morphine, DAGO, DADLE or dynorphin to etorphine-treated cells no longer evoked the usual APD prolongation observed in the same cells prior to exposure to etorphine (n=11; see FIG. 2C). This etorphine-induced blockade of opioid excitatory effects on DRG neurons was often effective for periods up to 0.5–2 hours after washout (n=4).

These results demonstrate that etorphine, which has been considered to be a "universal" agonist at mu, delta and kappa opioid receptors (see Magnan et al., *Naunyn-Schmiedeberg's Arch. Pharmacol.*, Vol. 319, pp. 197–205 (1982)), has potent antagonist actions at mu, delta and kappa excitatory opioid receptors on DRG neurons, in addition to its well-known agonist effects at inhibitory opioid receptors. Pretreatment with dihydroetorphine (fM-pM) showed similar antagonist action at excitatory opioid receptor mediating nM opioid-induced APD prolongation (n=2). Furthermore, after selective blockade of opioid excitatory APD-prolonging effects by pretreating DRG neurons with low concentrations of etorphine (fM-pM), which showed little or no alteration of the APD, fM-nM levels of bimodally-acting opioids now showed potent inhibitory APD-shortening effects (5 out of 9 cells) (see FIG. 2C and FIG. 4). This is presumably due to unmasking of inhibitory opioid receptor-mediated functions in these cells after selective blockade of their excitatory opioid receptor functions by etorphine.

EXAMPLE 2

Diprenorphine, Naloxone and Naltrexone, at Low Concentrations, Also Show Potent Selective Antagonist Action at Excitatory Opioid Receptors Drug tests: Mouse DRG-cord explants, grown for >3 weeks as described in Example 1, were tested with the opioid antagonists diprenorphine, naltrexone and naloxone. Electrophysiological recordings were made as in Example 1.

Results: The opioid receptor antagonists naloxone and diprenorphine were previously shown to block, at nM concentrations, both inhibitory APD shortening of DRG neurons by $\mu$M opioid agonists as well as excitatory APD prolongation by nM opioids. Tests at lower concentrations have revealed that pM diprenorphine, as well as pM naloxone or naltrexone, act selectively as antagonists at mu, delta and kappa excitatory opioid receptors, comparable to the antagonist effects of pM etorphine and dihydroetorphine. In the presence of pM diprenorphine, morphine (n=7) and DAGO (n=7) no longer elicited APD prolongation at low (pM-nM) concentrations (see FIG. 4A). Instead, they showed progressive dose-dependent APD shortening throughout the entire range of concentrations from fM to $\mu$M (see FIG. 4B), comparable to the dose-response curves for etorphine and dihydroetorphine (see FIG. 3 and FIG. 2C). This unmasking of inhibitory opioid receptor-mediated APD-shortening effects by pM diprenorphine occurred even in the presence of 10-fold higher concentrations of morphine (see FIG. 4A, records 11 vs. 5).

Figure 4B:
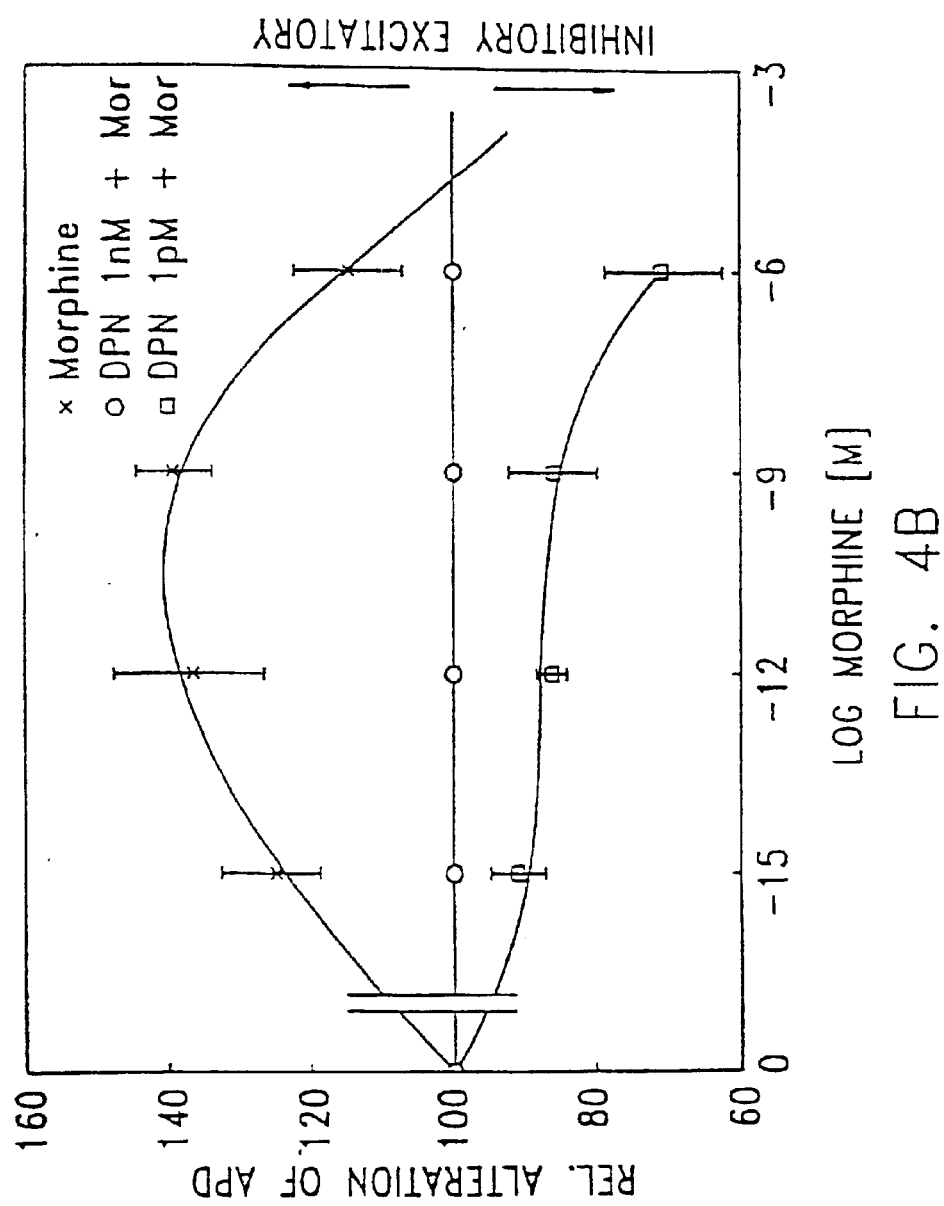

FIG. 4 shows that excitatory APD-prolonging effects elicited by morphine in DRG neurons are selectively blocked by co-administration of a low (pM) concentration of diprenorphine, thereby unmasking potent dose-dependent inhibitory APD shortening by low concentrations of morphine. FIG. 4A records 1–4 show that APD of a DRG neuron is progressively prolonged by sequential bath perfusions with 3 fM, 3 pM and 3 $\mu$M morphine (Mor). FIG. 4A record 5 shows that APD of this cell is only slightly shortened after increasing morphine concentration to 3 pM. FIG. 4A records 6 and 7 show that after transfer to 355, the APD is slightly shortened during pretreatment for 17 minutes with 1 pM diprenorphine (DPN). FIG. 4A records 8–11 show that after the APD reached a stable value in DPN, sequential applications of 3 fM, 3 pM, 3 nM and 3 $\mu$M Mor progressively shorten the APD, in contrast to the marked APD prolongation evoked by these same concentrations of Mor in the absence of DPN (see also FIG. 2C). FIG. 4B dose-response curves demonstrate similar unmasking by 1 pM DPN of potent dose-dependent inhibitory APD shortening by morphine (□) in a group of DRG neurons (n=7), all of which showed only excitatory APD prolongation responses when tested prior to introduction of DPN (X). Note that the inhibitory potency of morphine in the presence of pM DPN becomes comparable to that of etorphine and dihydroetorphine (see FIG. 3). In contrast, pretreatment with a higher (nM) concentration of DPN blocks both inhibitory as well as excitatory effects of morphine (●).

Figure 5:
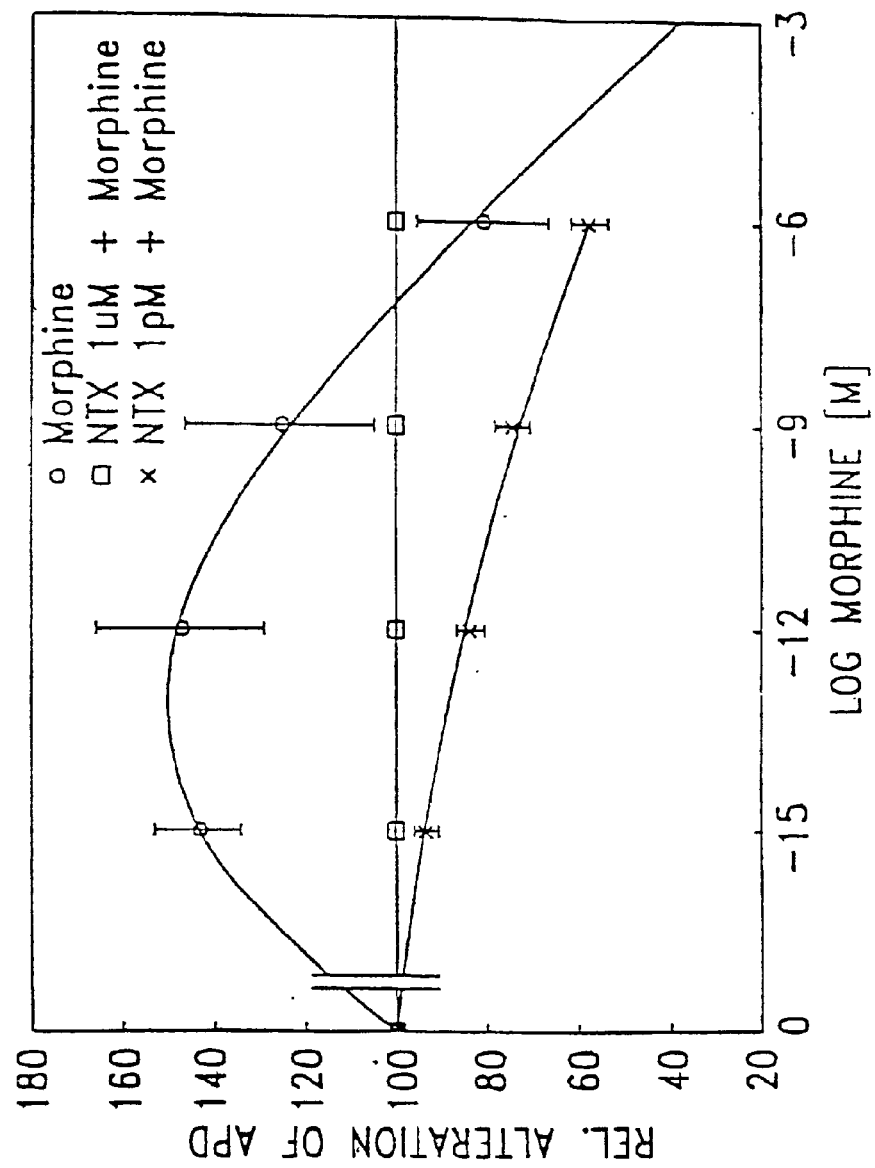
FIG. 5 represents similar selective blocking of excitatory APD-prolonging effects elicited by morphine in DRG neurons when co-administered with a low (pM) concentration of naltrexone, thereby unmasking potent inhibitory APD shortening by low concentrations of morphine. In contrast, a higher ($\mu$M) concentration of naltrexone blocks both inhibitory as well as excitatory opioid effects.

FIG. 5 shows that excitatory APD-prolonging effects elicited by morphine in DRG neurons (○) are also selectively blocked by co-administration of a low (pM) concentration of naltrexone (NTX), thereby unmasking potent dose-dependent inhibitory APD shortening by low concentrations or morphine (X). In contrast, pretreatment with a higher ($\mu$M) concentration of NTX blocks both inhibitory as well as excitatory effects of morphine (□) (similar blockade occurs with 1 nM NTX). These dose-response curves are based on data from 18 neurons, all of which showed only excitatory APD prolongation responses when tested prior to introduction of NTX. The inhibitory potency of morphine in the presence of pM NTX becomes comparable to that of etorphine and dihydroetorphine (see FIG. 3).

EXAMPLE 3

Chronic Co-treatment of DRG Neurons with Morphine and Ultra-low-dose Naloxone or Naltrexone Prevents Development of Opioid Excitatory Supersensitivity ("Dependence") and Tolerance Co-administration of ultra-low (pM) concentrations of naloxone or naltrexone during chronic treatment of DRG neurons with $\mu$M levels of morphine was effective in preventing development of opioid excitatory supersensitivity and tolerance which generally occurs after sustained exposure to bimodally-acting opioids. Acute application of fM dynorphin A-(1–13) or fM morphine (n=21), as well as 1 nM naloxone (n=11), to DRG neurons chronically exposed to 1 $\mu$M morphine together with 1 pM naloxone or naloxone or naltrexone (for 1–10 weeks) did not evoke the usual excitatory APD prolongation observed in chronic morphine-treated cells tested after washout with BSS (see FIG. 6). Furthermore, there was no evidence of tolerance to the usual inhibitory effects of AM opioids (n=6) (FIG. 6).

These results are consonant with previous data that blockade of sustained opioid excitatory effects by cholera toxin-B sub-unit during chronic morphine treatment of DRG neurons prevents development of tolerance and dependence (see Shen and Crain, *Brain Res.*, Vol. 597, pp. 74–83 (1992)). This toxin sub-unit selectively interferes with GM1 ganglioside regulation of excitatory opioid receptor functions (see Shen and Crain, *Brain Res.*, Vol. 531, pp. 1–7 (1990) and Shen et al., *Brain Res.*, Vol. 559, pp. 130–138 (1991)).

Similarly, in the presence of pM etorphine, chronic $\mu$M morphine-treated DRG neurons did not develop signs of tolerance or dependence. FIG. 6 outlines the assay procedure used for testing the effectiveness of these and other antagonists at excitatory opioid receptors in preventing development of tolerance/dependence during chronic co-treatment of DRG neurons with morphine.

EXAMPLE 4

Excitatory Opioid Receptor Antagonists Enhance Analgesic Potency and Reduce Dependence Liability and Other Side Effects of Morphine when Administered in Combination with Morphine Electrophysiological studies on DRG neurons in culture indicated that pretreatment with low fM-pM concentrations of naltrexone, naloxone, diprenorphine, etorphine or dihydroetorphine is remarkably effective in blocking excitatory APD-prolonging effects of morphine or other bimodally-acting opioid agonists by selective antagonist actions at mu, delta and kappa excitatory opioid receptors on these cells. In the presence of these selective excitatory opioid receptor antagonists, morphine and other clinically used bimodally-acting opioid agonists showed markedly increased potency in evoking the inhibitory effects on the action potential of sensory neurons which are generally considered to underlie opioid analgesic action in vivo.

These bimodally-acting opioid agonists became effective in shortening, instead of prolonging, the APD at pM-nM (i.e., $10^{-12}$-$10^{-9}$ M) concentrations, whereas 0.1–1 $\mu$M (i.e., $10^{-7}$–$10^{-6}$ M) levels were generally required to shorten the APD (FIGS. 4B and 5). Selective blockade of the excitatory side effects of these bimodally-acting opioid agonists eliminates the attenuation of their inhibitory effectiveness that would otherwise occur. Hence, according to this invention, the combined use of a relatively low dose of one of these selective excitatory opioid receptor antagonists, together with morphine or other bimodally-acting mu, delta or kappa opioid agonists, will markedly enhance the analgesic potency of said opioid agonist, and render said opioid agonist comparable in potency to etorphine or dihydroetorphine, which, when used alone, are >1000 times more potent than morphine in eliciting analgesia.

Co-administration of one of these excitatory opioid receptor antagonists at low (pM) concentration ($10^{-12}$ M) during chronic treatment of sensory neurons with $10^{-6}$ M morphine or other bimodally-acting opioid agonists (>1 week in culture) prevented development of the opioid excitatory supersensitivity, including naloxone-precipitated APD-prolongation, as well as the tolerance to opioid inhibitory effects that generally occurs after chronic opioid exposure. This experimental paradigm was previously utilized by the inventors on sensory neurons in culture to demonstrate that co-administration of $10^{-7}$ M cholera toxin-B sub-unit, which binds selectively to GM1 ganglioside and thereby blocks excitatory GM1-regulated opioid receptor-mediated effects, but not opioid inhibitory effects (see Shen and Crain, *Brain Res.*, Vol. 531, pp. 1–7 (1990)), during chronic opioid treatment prevents development of these plastic changes in neuronal sensitivity that are considered to be cellular manifestations related to opioid dependence/addiction and tolerance in vivo (see Shen and Crain, *Brain Res.*, Vol. 597, pp. 74–83 (1992)).

EXAMPLE 5

Cotreatment of Mice with Morphine Plus Ultra Low Dose Naltrexone Enhances Opioid Antinociceptive Potency Antinociceptive effects of opioids were measured using a warm-water tail flick assay similar to methods described in Horan, P.J., et al. *J. Pharmacol. Exp. Ther.* 264: 1446–1454 (1993). In this regard, each mouse was inserted into a plastic restraining device that permitted the tail to be dipped into a water bath maintained at 55° C. The latency to a rapid tail flick was recorded; mice with control latencies >5 seconds were excluded from these tests and a 10 second cutoff was used to minimize tissue damage. Six sequential control tests were made, each with a 10 minute interval. The latencies of the last four tests were averaged to provide a control value. Percent antinociception was calculated according to the formula: 100×[(test latency-control latency)/10-control latency)]. Differences between treatment groups were examined for statistical significance by means of ANOVA with Neuman-Keuls tests.

Figure 7:
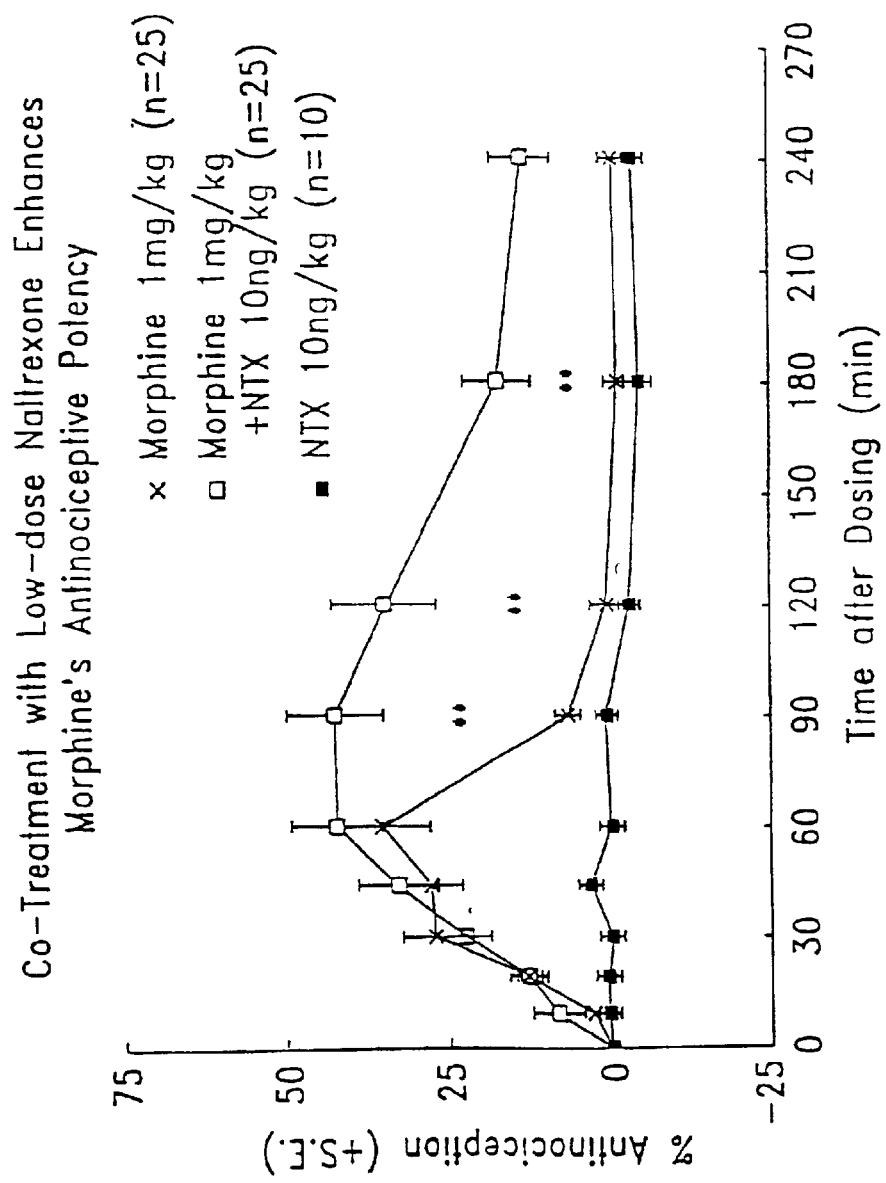
FIG. 7 represents a comparison of the antinociceptive potency of 1 mg/kg morphine administered (i.p.) to mice alone, 10 ng/kg naltrexone administered (i.p.) to mice alone, and a combination of 1 mg/kg morphine and 10 ng/kg naltrexone administered (i.p.) to mice. Shown are the time-response curves for 1 mg/kg morphine (x); 1 mg/kg morphine and 10 ng/kg naltrexone (NTX) (□); 10 ng/kg naltrexone (■), in a warm-water (55° C.) tail-flick test. Twenty-five mice were used per dosing group (10 animals for NTX alone). Injection of 10 ng of NTX per kg alone did not elicit analgesic effects. **, Statistically significant difference between individual morphine vs. morphine plus naltrexone time points: P<0.01.

Untreated mice showed tail-flick latencies of 2.15±0.4 seconds (mean±SD; n+58). Cotreatment of mice with 10 mg of morphine per kg plus a 1000-fold lower dose of naltrexone (10 $\mu$g/kg, i.p.) resulted in moderate attenuation and no significant enhancement of the analgesic potency of morphine injected alone. In contrast, cotreatment of mice with 1 mg of morphine per kg plus a 100,000 fold lower dose of naltrexone (10 ng/kg, i.p.) demonstrated that in the presence of this extremely low dose of naltrexone, the peak values of tail-flick latencies at 1 hour were maintained during the subsequent hour, whereas the antinociceptive effects of morphine alone rapidly decreased during this same period. Furthermore, a remarkable degree of antinociception was maintained for >1.5 hours after the effects of 1 mg of morphine per kg alone were no longer detectable (n=25; FIG. 7). The marked enhancement of the analgesic potency of morphine in mice during cotreatment with 10 ng of naltrexone per kg is quite consonant with the unmasking of potent inhibitory effects of 1 pM-1 nM morphine in DRG neurons in vitro by cotreatment with 1 pM naltrexone.

EXAMPLE 6

Cotreatment of Mice with Morphine Plus Low-Dose Naltrexone Attenuates Withdrawal Jumping Behavior Acute Physical Dependence Assays Acute physical dependence was assessed by recording naloxone-precipitated withdrawal jumping behavior in mice that had been injected 3–4 hours earlier with a 100 mg/kg (s.c.) dose of morphine (Horan, P. J., et al. supra; Yano, I. and Takemori, A. E. *Res. Commun. Chem. Pathol. Pharmacol.* 16: 721–733 (1977); Sofuoglu, M., et al. *J. Pharmacol. Exp. Ther.* 254:841–846 (1990), administered alone or together with a low dose of naltrexone. Each mouse was placed individually in a tall container and the number of abrupt, stereotyped jumps was recorded during a 15 minute period after administration of naloxone (10 mg/kg, i.p.). Differences between treatment groups were examined for statistical significance by means of $X^2$ tests.

Figure 8:
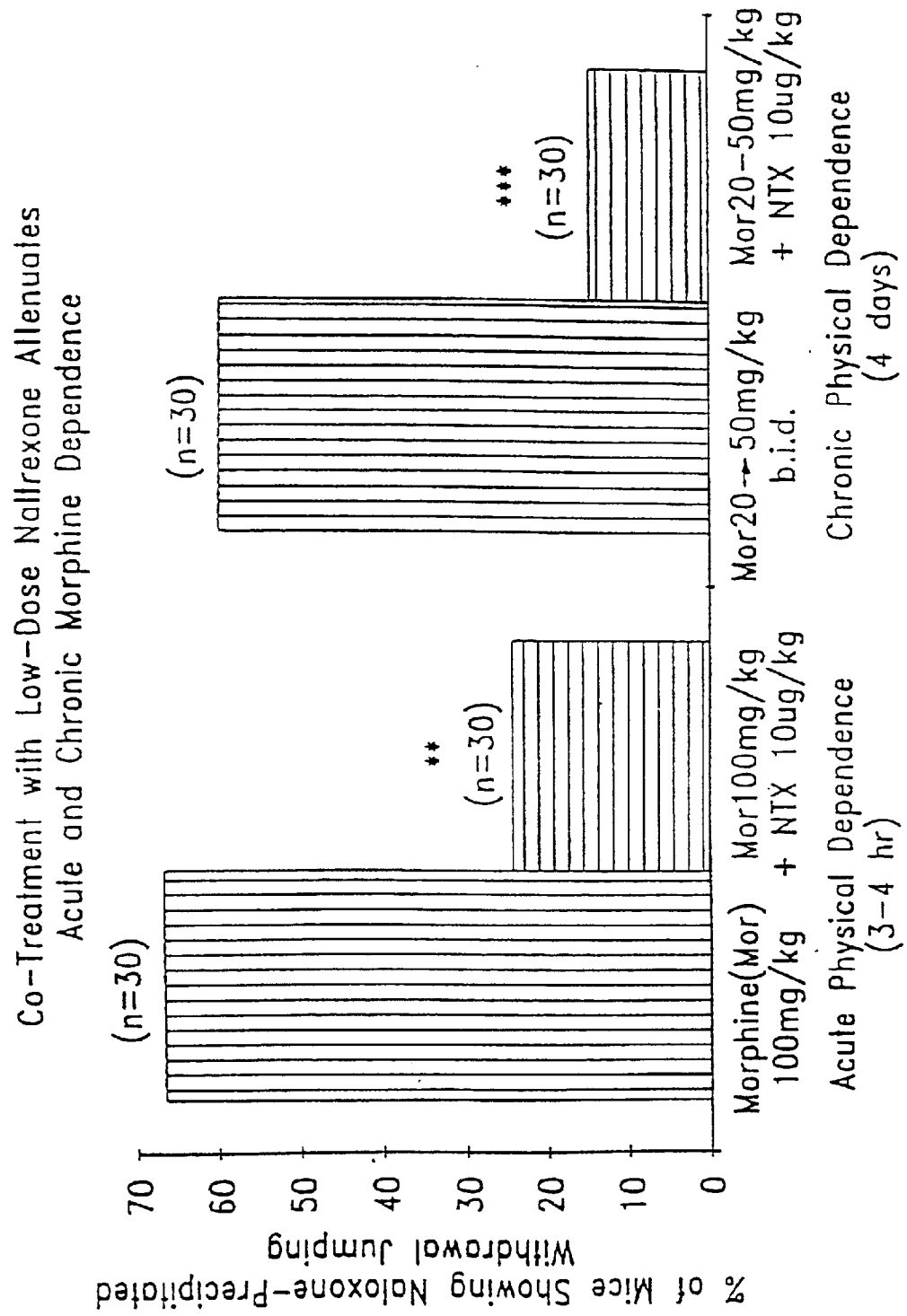
FIG. 8 represents a comparison of the percentage of mice showing naloxone-precipitated withdrawal jumping (i) 3–4 hours after injection with morphine alone (100 mg/kg, s.c.), and morphine (100 mg/kg, s.c.) plus naltrexone (10 $\mu$g/kg, s.c.) (acute physical dependence assay); and (ii) 4 days after increasing daily injections with morphine alone (20–50 mg/kg, s.c.), and morphine (20–50 mg/kg, s.c.) plus naltrexone (10 $\mu$g/kg, s.c.) (chronic physical dependence assay). , Statistically significant difference from control morphine alone group: P<0.01; *, P<0.001.

Three to four hours after the administration of a high dose of morphine (100 mg./kg, s.c.), injection of naloxone (10 mg/kg, i.p.) evoked characteristic withdrawal jumping behavior. About 67% of these treated mice (n=30) showed 5-100 robust jumps during a 15 minute test period (n=30; FIG. 8), whereas jumping behavior was observed in only 10–20% of untreated mice. On the other hand, after cotreatment of mice with a 10,000-fold lower dose of naltrexone (10 µg/kg) administered 15 minutes prior to and together with 100 mg of morphine per kg, the incidence of naloxone-precipitated jumping behavior was markedly reduced to only 23% of the treated animals (n=30; FIG. 8). The mice were routinely pretreated with naltrexone to ensure antagonist binding to excitatory opioid receptors prior to their possible long-lasting activation by morphine. An additional injection of naltrexone (10 µg/kg, s.c.) was made 2 hours after administration of morphine plus naltrexone, because this antagonist has been reported to have a much shorter duration of action in mice, in contrast to humans.

Antinociceptive tail-flick tests on naive mice were made in order to show that this effect of 10 µg of naltrexone per kg was mediated primarily by blocking excitatory, rather than inhibitory, opioid receptor functions. Cotreatment of mice with 100 mg of morphine per kg plus 10 µg of naltrexone per kg (i.p.) did not significantly attenuate the potent (supramaximal) analgesic effect of 100 mg of morphine per kg injected alone. In both groups of treated mice, tail-flick latencies rapidly increased to the peak cutoff value of 10 seconds.

Chronic Physical Dependence and Tolerance Assays

Chronic physical dependence was assessed by similar naloxone-precipitated withdrawal jumping behavior tests as described above in mice that had been injected for four days (twice daily) with increasing doses of morphine (20–50 mg/kg, s.c.), alone or together with a low dose of naltrexone. On the fifth day, the animals were primed with morphine (10 mg/kg) and challenged 1 hour later with naloxone (10 mg/kg, i.p.), as in previous chronic morphine-dependence assays (Sofuoglu, M., et al. *J. Pharmacol. Exp. Ther.* 254: 841–846 (1990); Brase, D. B., et al. *J. Pharmacol. Exp. Ther.* 197: 317–325 (1976); Way, E. L. and Loh, H. H. *Ann. N.Y. Acad. Sci.* 281: 252–261 (1976)). Differences between treatment groups were examined for statistical significance by means of $X^2$ tests.

About 60% of the treated mice showed stereotyped jumping as observed in the acute dependence tests (n=30; FIG. 8). By contrast, after cotreatment of mice with 10 µg of naltrexone per kg (s.c.) administered 15 minutes prior to and together with each of the morphine injections indicated above, naloxone-precipitated jumping occurred in only 13% of the mice (n=30; FIG. 8). Tail-flick assays on naive mice showed that cotreatment with 20 mg of morphine per kg plus 10 µg of naltrexone per kg did not significantly attenuate the analgesic effect of 20 mg of morphine per kg injected alone. In similar chronic cotreatment tests using a 10-fold lower dose of naltrexone (1 µg/kg), withdrawal jumping was still markedly attenuated from 60% down to 30% of the mice (n=30; data not shown). These results demonstrate that chronic cotreatment with morphine plus 50,000- to 5,000-fold lower doses of naltrexone significantly decreased development of physical dependence.

Tail-flick assays on some of these chronic cotreated mice at 1 day after drug withdrawal showed that opioid tolerance was also partially attenuated. Acute injection of 1 mg of morphine per kg resulted in a much larger degree of antinociception in chronic morphine plus 10 ng of naltrexone per kg cotreated mice (15%±3%, n=10; time to peak effect at 30 minutes), as compared to chronic morphine-treated mice (3%±2% at 30 minutes, n=10; peak effect of 7%±1$ at 60 minutes) (data not shown).

EXAMPLE 7

Figure 9:
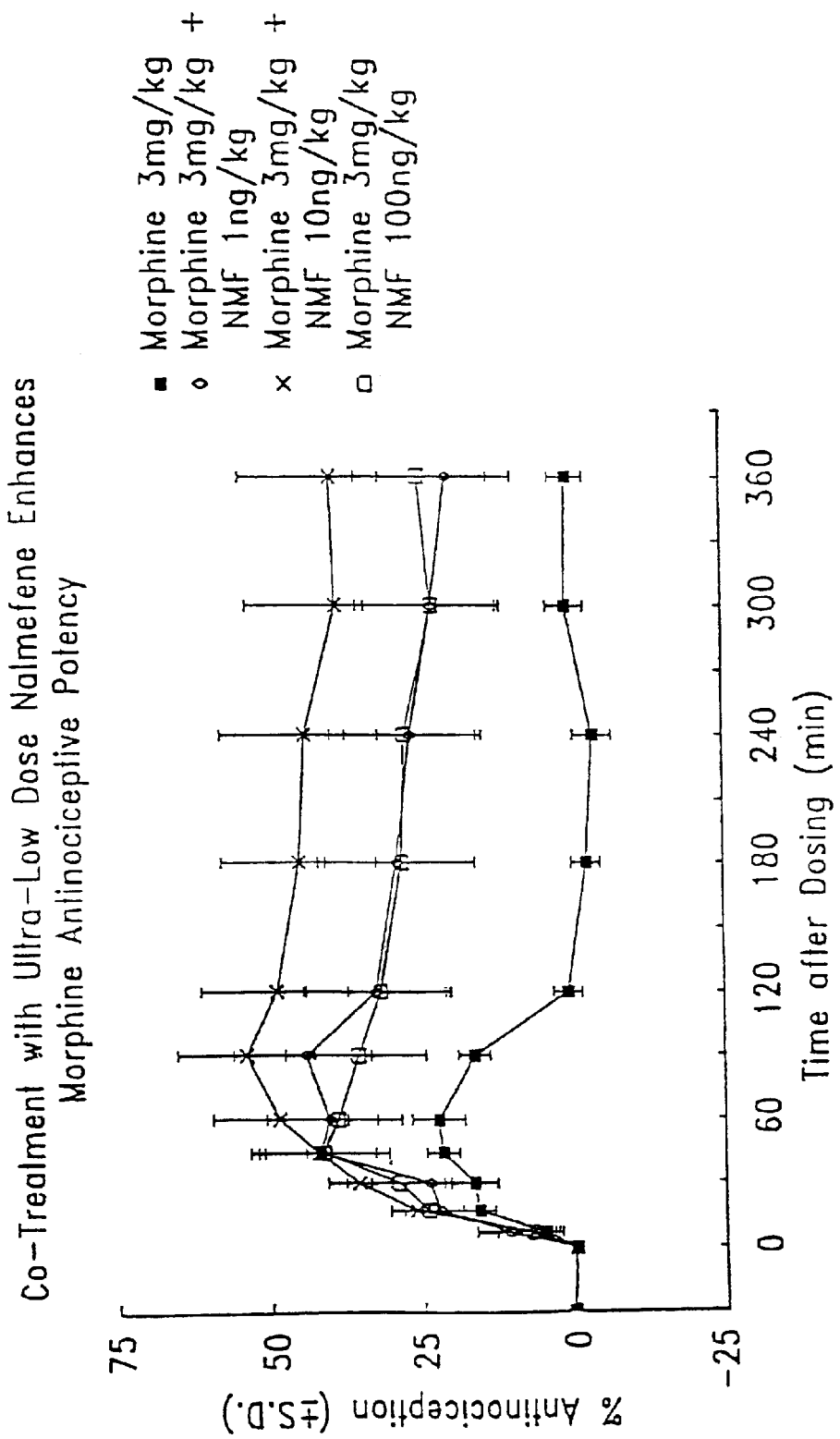
FIG. 9 represents a comparison of the antinociceptive potency of morphine administered (i.p.) to mice alone, and morphine administered (i.p.) to mice in combination with various ultra-low doses of nalmefene (NMF). Shown are the time-response curves for 3 mg/kg morphine (●); 3 mg/kg morphine and 100 ng/kg nalmefene (□); 3 mg/kg morphine and 10 ng/kg nalmefene (x); and 3 mg/kg morphine and 1 ng/kg nalmefene (◇) in a warm-water (55° C.) tail-flick test. Ten mice were used per dosing group.

Cotreatment of Mice with Morphine Plus Low-Dose Nalmefene Enhances Opioid Antinociceptive Potency Mice were injected (i.p.) with 3 mg/kg morphine alone, and 3 mg/kg morphine in combination with 30,000-fold lower dose of nalmefene (100 ng/kg, i.p.), 300,000-fold lower dose of nalmefene (10 ng/kg, i.p.) and 3,000,000-fold lower dose of nalmefene (1 ng/kg, i.p.). Ten mice were used per dosing group. Antinociceptive effects of opioids were measured using a warm-water tail flick assay as described above. The results are presented in FIG. 9. Co-treatment of mice with ultra-low doses of nalmefene (NLF) enhances morphine's antinociceptive potency, in contrast to the characteristic attenuation of morphine analgesia by higher doses of nalmefene. Co-treatment with 1 ng/kg nalmefene was as effective as 10 ng/kg naltrexone in enhancing morphine antinociceptive potency (compare FIGS. 7 and 9).

EXAMPLE 8

Figure 10:
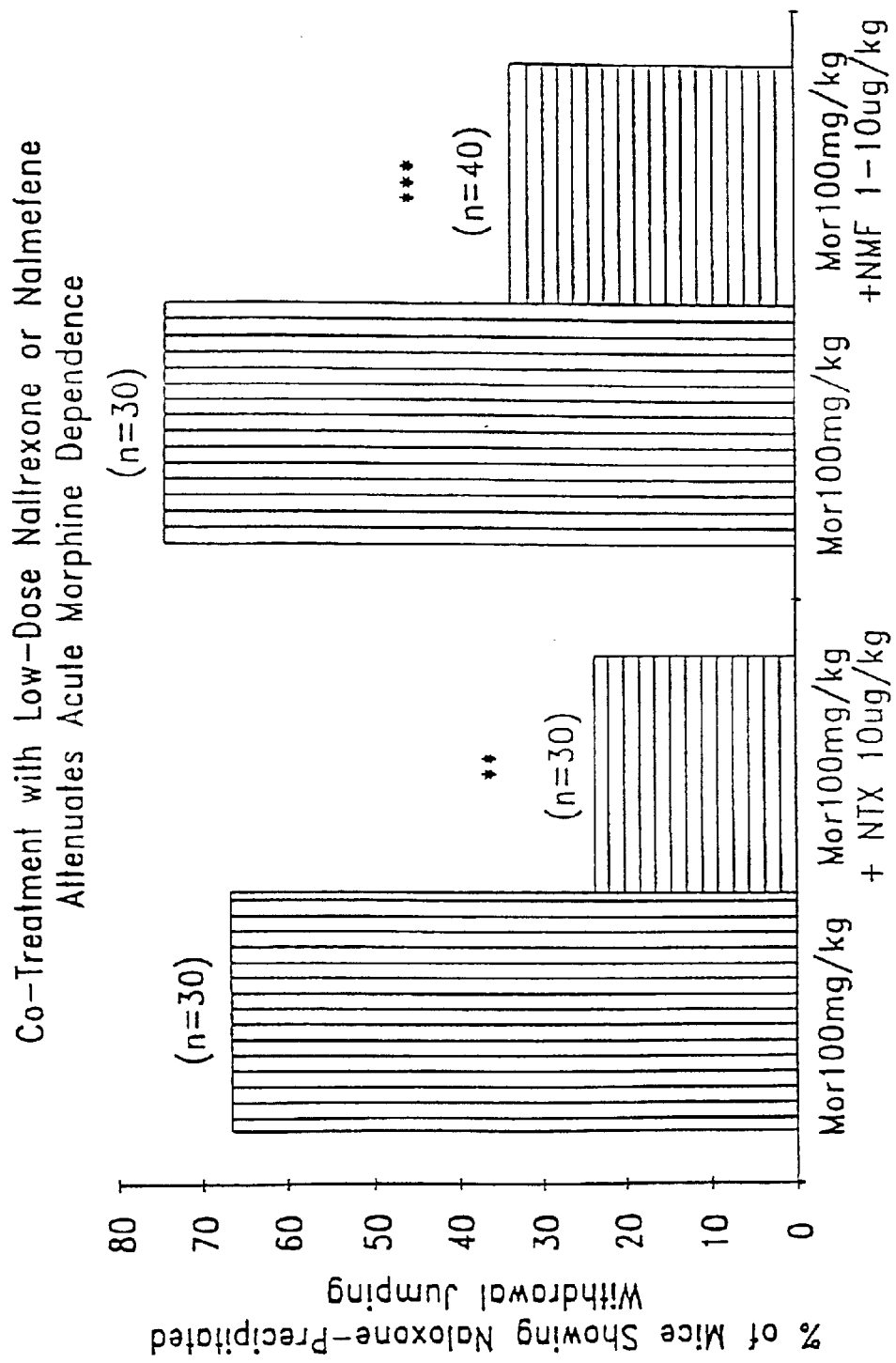
FIG. 10 represents a comparison of the percentage of mice showing naloxone-precipitated withdrawal jumping 4 hours after injection (acute physical dependence assay) with a 100 mg/kg (s.c.) dose of morphine (Mor) alone or in combination with 1 or 10 $\mu$g/kg (s.c.) dose of nalmefene (NMF) or 10 $\mu$g/kg (s.c.) dose of naltrexone (NTX). Additional injections of nalmefene (1 or 10 $\mu$g/kg, s.c.) or naltrexone (10 $\mu$g/kg, s.c.) were made 90 minutes after the initial injections. , Statistically significant difference from control morphine alone group: P<0.01; *, P<0.001.

Cotreatment of Mice with Morphine Plus Low-Dose Nalmefene Attenuates Withdrawal Jumping Behavior Acute Physical Dependence Assays Mice were injected with a 100 mg/kg (s.c.) dose of morphine, administered either alone or in combination with 1 or 10 µg/kg (s.c.) dose of nalmefene or 10 µg/kg (s.c.) dose of naltrexone (as control), followed by additional injections of nalmefene (1 or 10 µg/kg, s.c.) or naltrexone (10 µg/kg, s.c.) 90 minutes after the initial injections. Acute physical dependence was assessed by recording naloxone-precipitated withdrawal jumping behavior in mice 4 hours after the initial injections. The results are presented in FIG. 10. Co-treatment of mice for 4 hours with morphine plus the low dose nalmefene (NLF; n=40) or naltrexone (NTX; n=30) attenuates naloxone-precipitated withdrawal-jumping in the acute physical dependence assays. These results demonstrate that co-treatment with nalmefene is as effective as naltrexone in attenuating morphine dependence liability. Tests with 1 µg/kg nalmefene (n=10) indicate that nalmefene may even be more effective than naltrexone in attenuating morphine dependence liability.

EXAMPLE 9

Cotreatment of Mice with Tramadol Plus Low-Dose Naltrexone Enhances Opioid Antinociceptive Potency Tramadol hydrochloride (1RS,2RS)-2[(dimethylamino)-methyl]-1-(3-methoxyphenyl)-cyclohexanol HCL (FIG. 1)

is an orally active, clinically effective, centrally acting, analgesic compound with opioid and non-opioid activity. Tramadol produces clinical analgesia (by p.o. or parenteral routes) as effectively as codeine and pentazocine (Arend, et al. *Arzneim. Forsch.*, 28: 199–208 (1978); Rost and Schenck, *Arzneim. Forsch*, 28: 181–183 (1978); Schenk and Arend, *Arzneim. Forsch*, 28: 196–199 (1978b); Richter, et al., *Naunyn-Schmiedeberg's Arch. Pharmacol.*, 313: suppl., R62 (1980)) against multiple pain conditions, such as post-surgical pain (Vogel, *Arzneim. Forsch.*, 28: 183–186 (1978)), obstretic pain (Bitsch, et al., *Fortschr. Med.*, 16: 632–634 (1980)), terminal cancer pain (Flohhe, et al., *Arzneim. Forsch.*, 28: 213–217 (1978)) and pain of coronary origin (Rettig and Kropp, *Therapiewoch*, 30: 5561–5566 (1980b)). The antinociceptive activity of tramadol in the mouse tail-flick test is blocked by opioid antagonists (Friderichs, et al., *Arzneim. Forsch.* 28: 122–134 (1978)), suggesting that tramadol-induced antinociception is mediated via opioid receptors. Furthermore, systematic studies on mice by Raffa, et al. (*J. Pharmacol. & Exp. Ther.* 260: 375–285 (1992)) suggest that tramadol produces antinociception not only via an opioid (predominantly $\mu$ receptor) mechanism but also via a separate nonopioid mechanism (probably related to its ability to inhibit neuronal uptake of norepinephrine or serotonin). Both mechanisms contribute to antinociception in vivo (Raffa, *Amer. J. Med.*, 101: Supp.1A: 40–46 (1996)). Data from a double-blind, cross-over study suggest that oral tramadol 120 mg is equipotent to oral morphine 30 mg (Wilder, et al., *Ann. Oncol.*, 5: 141–146 (1994)). Intravenous tramadol is approximately one-tenth as potent as morphine (Lee, et al., *Drugs*, 46: 313–340 (1993)). Tramadol is generally well tolerated, with dizziness, nausea, sedation, dry mouth and sweating being the principal adverse effects. Respiratory depression is uncommon (Lee, et al., *Drugs*, 46: 313–340 (1993); Vickers, et al., *Anaesthesia*, 47: 291–296 (1992)).

In the present example, mice were injected (i.p.) with 50 mg/kg tramadol alone, 50 mg/kg tramadol in combination with a 5,000,000-fold lower dose of naltrexone (10 ng/kg), 500,000-fold lower dose of naltrexone (0.1 $\mu$g/kg), 50,000-fold lower dose of naltrexone (1 $\mu$g/kg), a 5,000-fold lower dose of naltrexone (10 $\mu$g/kg), or a 500-fold lower dose of naltrexone (100 $\mu$g/kg). In another series of assays, mice were injected (i.p.) with 5 mg/kg tramadol alone, or 5 mg/kg tramadol in combination with graded dosages of naltrexone: 0.1 $\mu$g/kg, 1 $\mu$g/kg, or 10 $\mu$g/kg. Seven mice were used per dosing group. Antinociceptive effects of tramadol were measured using a hot-water (55° C.) immersion tail-flick assay similar to methods described above. Each mouse was inserted into a plastic restraining device that permitted the tail to be dipped into a water bath maintained at 55° C. The latency to a rapid tail-flick from water was recorded; mice with control latencies >5 seconds were excluded from these tests and a 10 second cutoff was used to minimize tissue damage. Five sequential control tests were made, each with a 10 minute interval. The latencies of the last four tests were averaged to provide a control value. Differences between treatment groups were examined for statistical significance by means of ANOVA with Neuman-Keuls tests.

Figure 11:
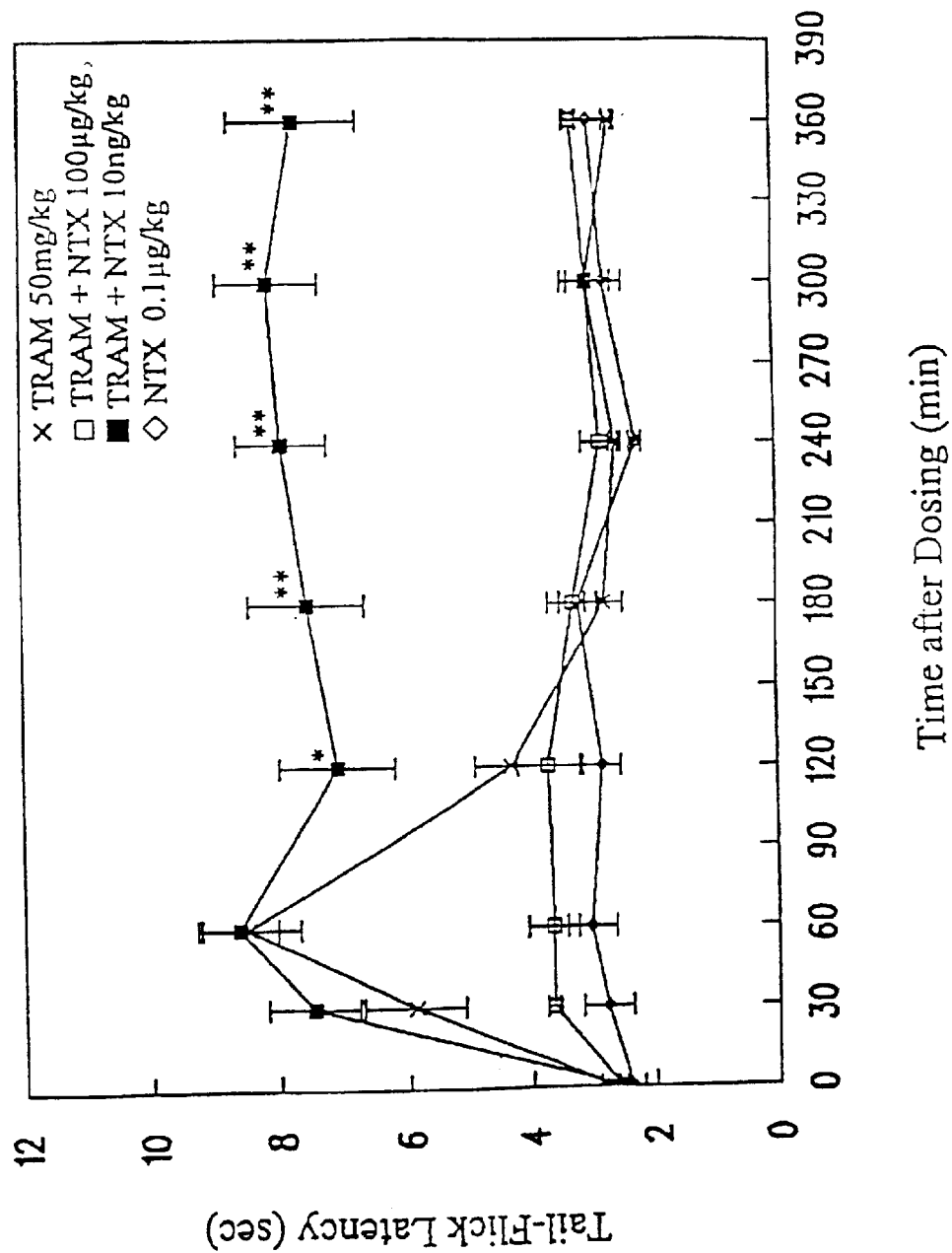
FIG. 11 represents time-effect curves showing the antinociceptive effects of tramadol±naltrexone in mice (measured using tail-flick latencies during hot water (55° C.) immersion tail-flick assays). Cotreatment of mice with a high dose of tramadol (50 mg/kg, i.p.) plus a 5,000,000-fold lower dose of naltrexone (NTX) (10 ng/kg, i.p.) markedly prolonged antinociception for >3 hr after the effect of tramadol alone (x) was not longer detectable (■). By contrast, cotreatment with 50 mg/kg tramadol plus 100 $\mu$g/kg NTX almost completely blocked tramadol's antinociceptive effect (□), in agreement with previous studies showing that higher doses of NTX (>>10 $\mu$g/kg) result in dose-dependent attenuation of tramadol antinociception (e.g. Raffa, et al. *J. Pharm. Exp. Ther.* 260: 275–285 (1992)). Furthermore, injection of 0.1 $\mu$g/kg NTX alone did not elicit analgesic effects under these assay conditions (◇). Note: n=7 for each curve; asterisks indicate statistically significant differences between tramadol vs. tramadol+NTX time points: P<0.01, P<0.05 (similar codes used in FIGS. 12 and 13).
Figure 12:
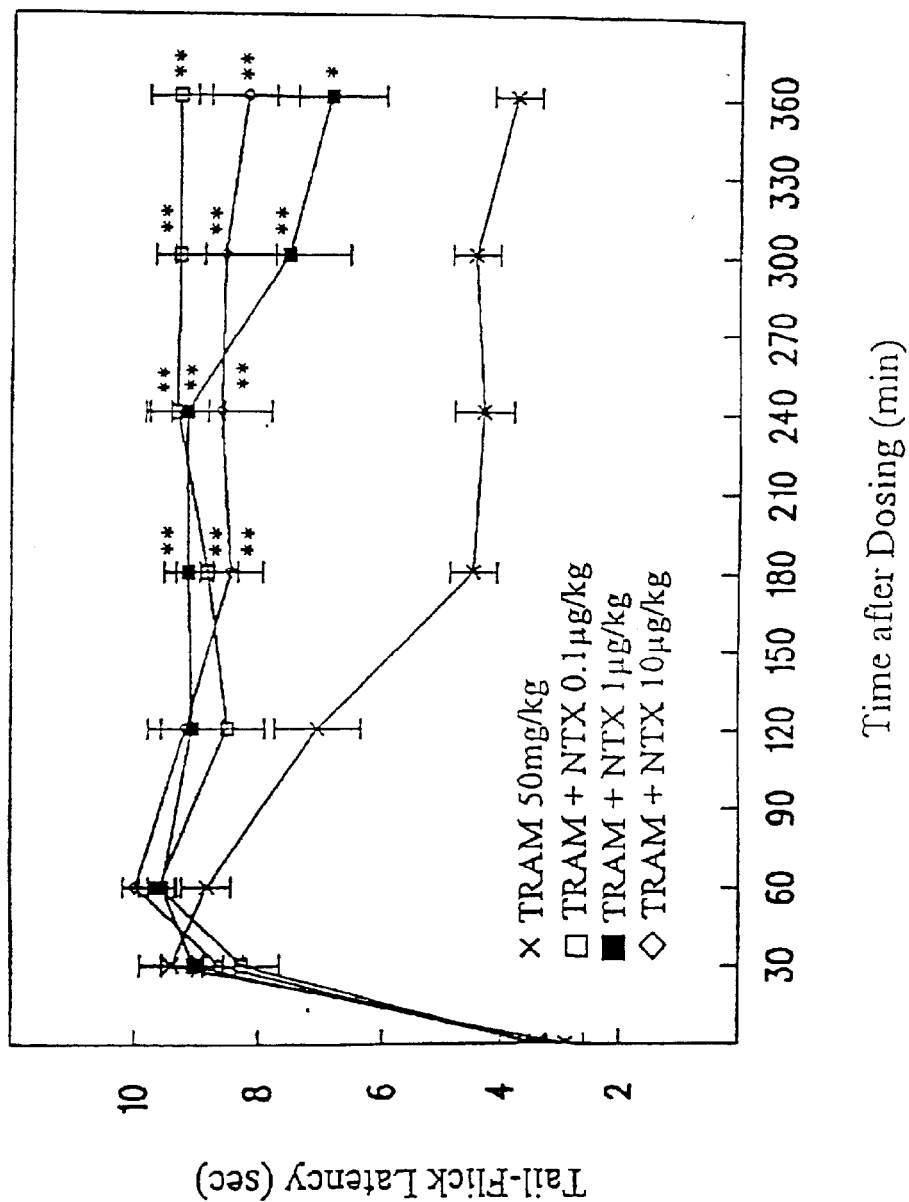
FIG. 12 represents dose-response curves showing cotreatment of mice with 50 mg/kg tramadol plus intermediate doses of NTX: 0.1 $\mu$g/kg (□), 1 $\mu$g/kg (■), and 10 $\mu$g/kg (◇) also markedly prolonged tramadol's antinociceptive effects for >3 hr (cf.
Figure 13:
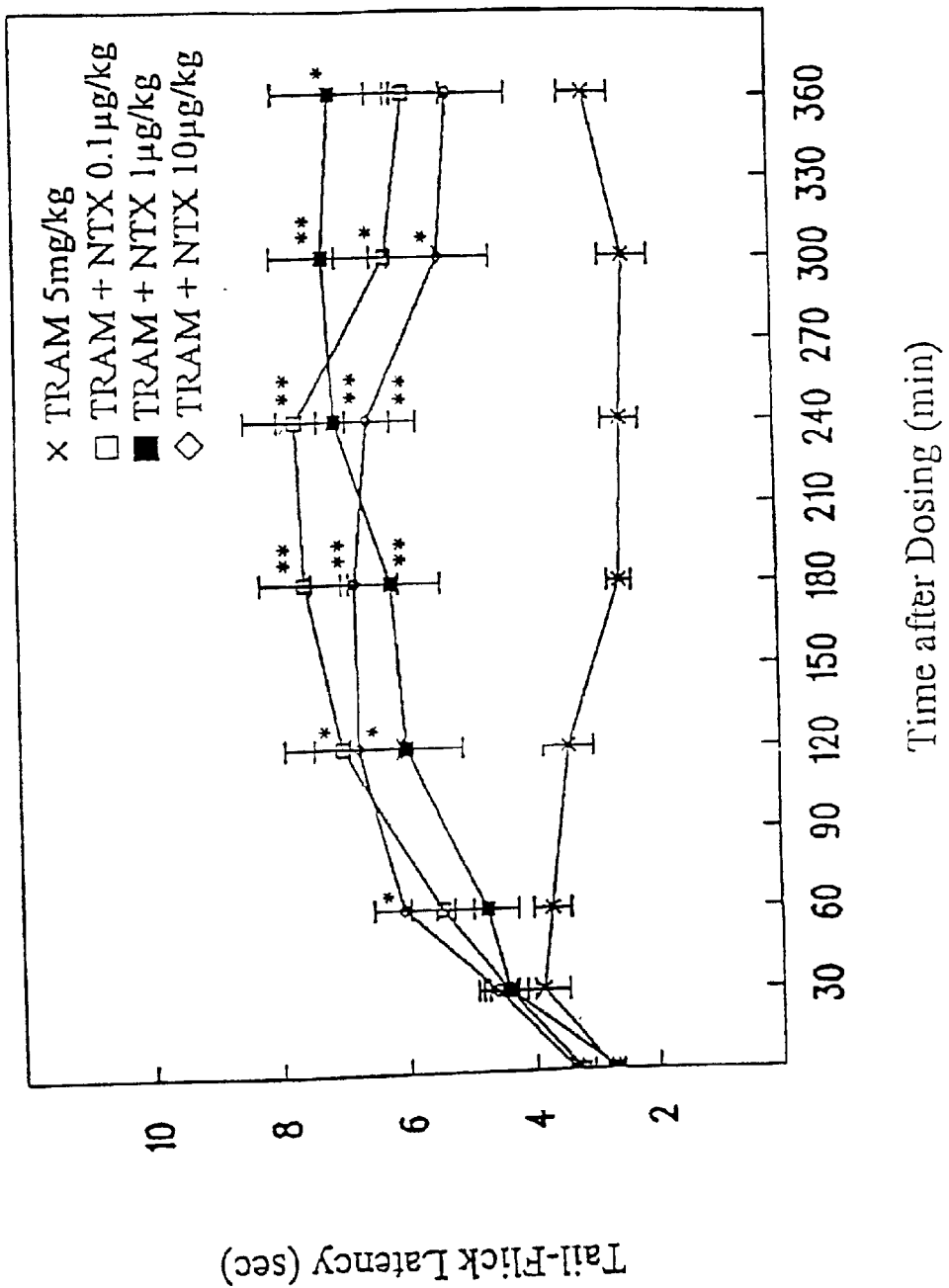
FIG. 13 represents dose-response curves showing cotreatment of mice with a low, almost subanalgesic dose of tramadol (5 mg/kg, i.p.) plus a 50,000-fold, 5,000-fold or 500-fold lower doses of NTX (0.1 $\mu$g/kg (□), 1 $\mu$g/kg (■), or 10 $\mu$g/kg (◇), i.p.) resulted in onset of significant antinociception within 1 hr (comparable to the effect of the much more potent opioid agonist, morphine, administered alone) and maintenance of this degree of antinociception during the subsequent 5-hr test period (as occurs after cotreatment with morphine plus ultra-low dose naltrexone). Tramadol 5 mg/kg (x) was used as the control.

Cotreatment of mice (i.p.) with 50 mg/kg tramadol plus 0.1 mg/kg naltrexone almost completely blocked tramadol's antinociceptive effects. This result is in agreement with previous studies demonstrating that, tramadol-induced antinociception is mediated via inhibitory opioid receptors (Friderichs, et al., *Arzneim. Forsch.* 28: 122–134 (1978); Raffa, et al. *J. Pharm. Exp. Ther.* 260: 275–285 (1992)). By contrast, the marked enhancement of the amplitude and duration of tramadol's analgesic effects in mice during co-treatment with much lower doses of naltrexone (ca. 0.01–10 $\mu$g/kg; FIGS. 11–13) is quite similar to the enhancement of morphine's analgesic potency during cotreatment with ultra-low dose naltrexone which selectively blocks excitatory, but not inhibitory, opioid receptor functions.

EXAMPLE 10

Cotreatment of Humans with Tramadol Plus Various Doses of Naltrexone

Tramadol hydrochloride (tramadol), as described in Example 9, is recognized as a centrally acting analgesic compound with opioid and non-opioid activity. This synthetic analgesic has a novel mechanism of action involving a complementary and synergistic interaction between inhibition of neuronal monamine reuptake and weak affinity for opioid receptors. This duality of action has prompted the classification of tramadol as a non-traditional centrally-acting analgesic (Raffa et al., *Rev. Contemp. Pharmacother.* 6: 485–497 (1995)). In most animal models, the analgesic action of tramadol is attenuated, but not blocked by naloxone. In contrast, however, in the tail-flick test, naloxone totally blocks tramadol as well as morphine- and codeine-induced antinociception (Raffa et al., supra). In a study in human volunteers, the attenuation by administration of naloxone (0.8 mg IV) to the volunteers who had received 100 mg tramadol orally, was reported to be about 30–35%, demonstrating that the non-opioid mechanism plays a significant role in tramadol's analgesic action in humans (Collart et al., *Br. J. Clin. Pharmacol.* 35: 73P (1993)). The nature of the non-opioid component of tramadol-induced analgesia in human volunteers was examined by Desmeules et al. *Experentia.* 50: A79 (1994a) and *Clin. Pharmacol. Ther.* 55: 151 (1994b), following 100 mg orally administered tramadol. The IV administration of the $\alpha$2-adrenoceptor antagonist yohimbine (0.1 mg/kg) significantly reduced tramadol-induced analgesia ($\geq$89%). The addition of naloxone (0.8 mg IV) removed the residual analgesic effect. Since tramadol does not have affinity for $\alpha$2-adrenoreceptors, the approximately 90% reduction of tramadol-induced analgesia that was observed in human volunteers with yohimbine probably reflects the ability of tramadol to inhibit neuronal reuptake of norepinephrine (Raffa et al., supra). The norepinephrine uptake-inhibiting property of tramadol seems to reside primarily in the (–) enantiomer, whereas the modest opioid and 5-HT update-inhibiting properties of tramadol appear to reside primarily in the (+) enantiomer. Both enantiomers produce analgesia in humans, however, together they act in a complementary and synergistic manner. The synergy does not appear to extend to side effect measures (Raffa et al., supra).

In this study in human subjects/patients with pain, tramadol was administered alone or in combination with various amounts (doses) of an opioid antagonist, naltrexone. Opioid antagonists, such as naltrexone, are also referred to herein as "excitatory opioid receptor antagonists". The effects of the combination of tramadol and an opioid antagonist (e.g., naltrexone) on analgesia or analgesic potency were measured. The effects of such combination on tramadol's side effects in humans (e.g., dizziness, nausea, sedation, etc.) were also measured.

In this study, one objective was to determine whether an opioid antagonist such as naltrexone hydrochloride (hereafter referred to as naltrexone or NTX) enhances the analgesic properties of tramadol hydrochloride (hereafter referred to as tramadol or T) in human subjects/patients with pain following dental surgery. An additional objective was to evaluate whether an opioid antagonist such as NTX attenuated (e.g., reduced, blocked or prevented) tramadol's adverse side effects in humans. A positive control (T) and a negative control (placebo) was employed.

For this randomized, double-blind, active-controlled and placebo-controlled, parallel-group study, human subjects were randomized into one of the following five treatment groups:

Group 1: T (50 mg) with NTX (1 mg)
Group 2: T (50 mg) with NTX (0.1 mg)
Group 3: T (50 mg) with NTX (0.01 mg)
Group 4: T (50 mg) with Placebo
Group 5: Placebo with Placebo A positive control (T, Group 4) was used to determine the sensitivity of the clinical end points. A negative control (placebo, Group 5) was used to establish the frequency and magnitude of changes in clinical end points that may occur in the absence of an active treatment. A single oral dose of study medication was administered when the subject experienced moderate to severe pain following the surgical extraction of three or four third molars. At least one of the molars was required to be mandibular bony impacted.

The study included one investigator and sufficient patients to provide two hundred fifty (250) subjects for statistical analysis. Fifty subjects were to be randomly assigned to each of the five treatment groups. Two hundred fifty-four (254) subjects were actually entered in the study. The following numbers of subjects were actually assigned to the five treatment groups: 50 in Group 1; 52 in Group 2; 51 in Group 3; 50 in Group 4; and 51 in Group 5. Observations were made by subjects for up to eight hours after dosing with the study medication.

Inclusion Criteria were as follows: (1) male or female subjects of any race and at least sixteen years of age (a subject under eighteen years old participated only if emancipated or if a parent (or guardian) gave written informed consent); (2) able to speak and understand English and provide meaningful written informed consent; (3) outpatients in generally good health (in particular, the subject must have had no history of liver or kidney disease); (4) three or four third molars to be extracted (at least one tooth must be mandibular bony impacted) and the subject was considered to have had surgery significant enough to warrant an opioid analgesic; (5) an initial categorical pain intensity score of at least moderate on a scale of none, mild, moderate or severe, and the subject willing and able to complete the subject evaluations; (6) able to remain at the study site for at least eight hours following the dose of study drug; and (7) if female, postmenopausal, or physically incapable of childbearing, or practicing an acceptable method of birth control (IUD or hormones or diaphragm and spermicide or abstinence), and if practicing an acceptable method of birth control, must also have maintained a normal menstrual pattern for the three months prior to study entry and have had a negative urine pregnancy test performed within seven days before surgery.

Exclusion Criteria were as follows: (1) pregnant or breast-feeding; (2) have a history of hepatic or renal disease; (3) have a history of seizures, however, subjects with a history of juvenile febrile seizures could be included if there was no seizure history within the past ten years; (4) have a medical or psychiatric condition that compromises the subject's ability to give informed consent or appropriately complete the study evaluations; (5) have a known allergy or significant reaction to opioids, tramadol or naltrexone; (6) have a history of chronic opioid use or opioid abuse within six months prior to study; (7) have used an anticonvulsant drug or tricyclic antidepressant drugs (including serotonin reuptake inhibitors and doses of St. John's Wort exceeding 1,000 mg per day) within four weeks prior to study entry; (8) currently taking a monoamine oxidase inhibitor (MAOI) or have taken a MAOI within two weeks prior to study entry; (9) consumed alcohol twelve hours prior to surgery and consumed alcohol or caffeine-containing products during the eight-hour observation period; (10) have taken any of the following drugs from at least four hours prior to dosing until the end of the study: analgesics, including aspirin, acetaminophen, nonsteroidal anti-inflammatory drugs (NSAIDS) and opioids (or opioid combinations); minor tranquilizers; muscle relaxants and antihistamines, as well as long-acting analgesics (e.g., long-acting NSAIDs) from twelve hours prior to dosing until completion of study observations; (11) have previously participated in this study; and (12) have been a participant in a study of an investigational drug or device within thirty days prior to this study.

Following compliance with all Inclusion/Exclusion Criteria, all subjects with moderate to severe pain received one dose of study medication. Subjects received two capsules to take by mouth, one tramadol or placebo, the other naltrexone or placebo. Study medication was packaged per subject in study drug containers.

Randomization was used to avoid bias in the assignment of subjects to treatment, to increase the likelihood that known and unknown subject attributes (e.g., demographics and baseline characteristics) were evenly balanced across treatment groups, and to enhance the validity of statistical comparisons across treatment groups. Blinded treatment was used to reduce potential bias during data collection and evaluation of clinical end points.

Prior to randomization, the following was accomplished: (1) informed consent; (2) medical history and demographics; (3) inclusion and exclusion criteria; and (4) prior and concomitant medication.

Subjects were assigned to treatment groups based on a computer generated randomization schedule prepared prior to the study. The randomization was balanced by using permuted blocks. Study drug for each subject was packaged and labeled according to this randomization code. In order to achieve balance among treatment groups with respect to starting pain, subjects with moderate starting pain were assigned medication with the lowest available number (next sequential treatment number in ascending order). Subjects with severe starting pain were assigned medication with the highest available number.

Study medication was packaged in single-dose bottles identified by subject number and each contained 2 capsules. The label identified the study as PROTOCOL TA. Each bottle had a two-way drug disclosure label attached that listed the following information: subject number; cautionary statement; and general instructions. The labels bore the instructions: "Take contents when pain is moderate or severe." The tear-off portion of the label was removed prior to dispensing the study drug and attached unopened to the Label Page Case Report Form.

Any medications which a subject had taken in the twenty-four hours prior to surgery (including vitamins, thyroid or other prophylactic medication) had to be reported at the baseline visit on the concomitant medications Case Report Form. If the administration of any concomitant therapy became necessary due to treatment-emergent adverse events, it had to be reported on the appropriate Case Report Form. The medical monitor was notified in advance of (or as soon as possible after) any instances in which prohibited therapies according to the Exclusion Criteria were administered.

A pain assessment was performed pre-treatment. Following the dental surgery and, the subject's pain level was assessed by a trained observer. The subject reported the initial pain intensity by both (1) verbalizing one pain category (0=none, 1=mild, 2=moderate or 3=severe), and (2) using a Visual Analog Scale (VAS) of 0–100 mm where 0=no pain and 100=worst pain imaginable, by placing a single slash on the scale. The decision to medicate was based only on the categorical response. When the categorical pain level was moderate or severe, the subject then took the dose of study medication.

A pain assessment was also performed post-treatment. Following dosing, pain intensity and pain relief was recorded at the following times: 30 minutes, 60 minutes and hourly thereafter up to Hour 8 after dosing. All efficacy assessments were recorded by the subject in a diary in response to questioning by the trained observer. The observer questioned the subject for all observations and provided instruction as needed. Pain intensity was measured in response to the question, "How much pain do you have now?" with (1) subject response choices of none, mild, moderate and severe on a categorical scale, and (2) a mark on a 100-mm VAS. The pain relief relative to baseline was assessed in response to the question, "How much pain relief do you have now compared to when you took the medicine?" with subject response choices of none, a little, some, a lot, and complete. For the pain relief assessment, the subject was given a stopwatch and asked to stop it when any meaningful pain relief was felt.

Adverse events were assessed by non-directed questioning and recorded for the eight hours following dosing. A symptom checklist was also used for the most common adverse side effects of tramadol in humans (e.g., dizziness, drowsiness, nausea, vomiting, headache, pruritus). These assessments were self-recorded by the subject in a diary at 30 minutes, 60 minutes and hourly thereafter up to Hour 8 after dosing At the end of eight hours, or at the termination of hourly observations if sooner than eight hours, a global assessment was made by the subject and the observer in response to the question, "How do you rate the pain relief?" with response choices of excellent, very good, good, fair or poor. Assessment of adverse events continued for at least one hour following rescue medication. Subjects not completing at least the Hour 1 observation period were considered not evaluable for efficacy and were replaced.

The study was completed after eight hours of evaluation or upon receipt of rescue medication. Subjects could discontinue the study at any time.

Subjects who did not get adequate pain relief were provided a final set of pain observations. The subject was then given a rescue medication and discontinued from study. The subject was encouraged to wait at least until Hour 2 after administration of the study medication before using rescue medication. Subjects remedicating earlier than Hour 1 were not included in the analysis for efficacy. Subjects not remedicating during the eight hours of evaluation received a diary card and asked to record the time of remedication after they left the clinic.

Subjects were required to remain on the unit at least one hour after receiving rescue medication for adverse event evaluation. However, it was strongly recommended that these subjects remain at the site for the full eight hours after receiving study drug.

Efficacy Evaluations were performed using primary and secondary efficacy parameters. The primary efficacy parameters included: (1) 4-hour Total Pain Relief Scores (TOTPAR) (described below); (2) 4-hour Sum of Pain Intensity Differences (SPID), (categorical and VAS) (described below); (3) time to onset of meaningful pain relief within 8 hours; and (4) percent of subjects remedicating within 8 hours. The secondary efficacy parameters included: (1) 6 and 8 hour Total Pain Relief Scores (TOTPAR); (2) 6 and 8 hour Sum of Pain Intensity Difference (SPID), (Categorical and VAS); (3) hourly pain relief scores; (4) hourly pain intensity difference scores (categorical and VAS); (5) remedication time within 8 hours; and (6) global evaluations.

Safety Evaluations included: (1) Adverse Events (AE); and (2) symptom checklist. All adverse events occurring during the study had to be recorded on the case report forms. An adverse event was defined as any untoward medical occurrence connected with the subject being treated during the study, whether or not it was considered related to the study. All serious or unexpected adverse events, whether or not they were considered related to the study medication, had to be reported by telephone to the medical monitor immediately (no later than twenty-four hours after the investigator's receipt of the information) according to Ethical and Regulatory Requirements. The symptom checklist was used, as described above, to record the most common adverse side effects of tramadol in humans.

In this study, standard measurements and determinations were utilized. For example, pain intensity was evaluated using both a categorical scale and a VAS, which are standard measurement instruments in analgesic studies. A global assessment of pain relief using a categorical scale and measurements of time to rescue medication are both standard measurements. The safety measures (history, adverse events, and concomitant medications) were also standard determinations.

For the data analysis, computed parameters were as follows. The extent to which pain intensity changed over the test period were measured by the Total Pain Relief Score (TOTPAR) and the Sum of Pain Intensity Differences (SPID). TOTPAR was defined as the sum of Pain Relief Scores (PAR) (0=none, 1=a little, 2=some, 3=a lot, 4=complete) over the 4, 6 and 8-hour observation period. The Pain Intensity Difference (PID) at each time point was calculated as the difference between the Pain Intensity Score at Hour 0 and that score at the observation point (0=none, 1=mild, 2=moderate, 3=severe). SPID was defined as the sum of PIDs over the 4, 6 and 8-hour observation period. VAS-PID and VAS-SPID were defined similarly for the VAS scores. Missing values and evaluations performed after rescue medication were imputed by the Last Observation Carried Forward procedure (LOCF).

The primary analysis population was the Intent-To-Treat (ITT) population, which comprised all subjects who were randomized. All efficacy analyses were conducted on the ITT population. In addition, efficacy analyses were also conducted on the evaluable population which comprised subjects who were randomized, had pain or relief assessments after dosing, and stayed on the study for at least one hour.

One-way analysis of variance (ANOVA) was performed on TOTPAR, SPID and VAS-SPID. Each combination treatment was compared with the tramadol alone treatment with Fisher's least significant difference test (LSD), using Hochberg's (*Biometrik* 75: 800 (1988)) procedure to control the family-wise type 1 error. For all pairwise comparisons, the error mean square from the overall analysis of variance with all treatments were used as the estimate of error variance. Similar techniques were used for pain relief, PID and VAS-PID.

Time to remediation (or rescue medication) was analyzed using the Kaplan-Meier estimate to compute the survival distribution function. The distribution was compared among groups using the Log Rank Test. A subject was considered censored at eight hours if remediation had not occurred. Pairwise comparisons were made using the LIFETEST methodology. Hochberg's procedure was used to control the family-wise type 1 error. Time to Onset of Meaningful Relief (determined by the stopwatch) was similarly analyzed. Subjects who did not achieve meaningful relief or take rescue medications were considered treatment failures and were assigned a value of 8 hours or the time when the rescue medication was taken. In all the above analyses baseline pain intensity could be used as a stratification factor. The distribution of Starting Pain Intensity, Global Evaluations and Adverse Side Effects were displayed. The sample size was estimated from historical data and from practical considerations rather than from calculation of expected measured differences.

Efficacy analyses were conducted on 2 populations: the ITT population and the evaluable population (Table 1). The ITT population comprised all subjects who were randomized, took study drug, and had postrandomization data. The evaluable population comprised of only the ITT subjects who had pain or relief assessments after dosing and did not take rescue medication within the first hour following dosing.

A total of 254 subjects were randomized; among them, 253 subjects were deemed evaluable. One subject in Treatment Group I was not evaluable because the subject took rescue medication within 1 hour after dosing.

TABLE 1

Subject Evaluation Groups
All Subjects Screened

|  | Group 5 Placebo with Placebo | Group 4 T (50 mg) with Placebo | Group 1 Treatments T (50 mg) with NTX (1 mg) | Group 2 T (50 mg) with NTX (0.1 mg) | Group 3 T (50 mg) with NTX (0.01 mg) |
|---|---|---|---|---|---|
| Number of Subjects Screened = 254 | | | | | |
| Analyzed for Efficacy: | | | | | |
| Intent-To-Treat Subject | 51 | 50 | 50 | 52 | 51 |
| Evaluable Subjects | 51 | 50 | 49 | 52 | 51 |
| Analyzed for Safety: | 51 | 50 | 50 | 52 | 51 |
| Intent-To-Treat Subjects | | | | | |

The demographic and baseline characteristics were summarized by treatment groups for the ITT population and the evaluable population (Table 2). Demographic characteristics included age, race, sex, weight, height, medical history, teeth extracted (impacted and non-impacted), baseline pain intensity, and baseline visual analog scale.

The demographics were comparable across all 5 treatment groups. The baseline pain intensity scores and visual analog scale scores also were comparable across treatment groups (Table 3).

TABLE 2

Summary of Demographics
Intent-To-Treat Subjects

|  |  | Group 5 Placebo with Placebo | Group 4 T (50 mg) with Placebo | Group 1 Treatments T (50 mg) with NTX (1 mg) | Group 2 T (50 mg) with NTX (0.1 mg) | Group 3 T (50 mg) with NTX (0.01 mg) |
|---|---|---|---|---|---|---|
| Number of Subjects | | 51 | 50 | 50 | 52 | 51 |
| Sex | Male | 27 (52.9%) | 16 (32.0%) | 18 (36.0%) | 26 (50.0%) | 17 (33.3%) |
|  | Female | 24 (47.1%) | 34 (68.0%) | 32 (64.0%) | 26 (50.0%) | 34 (66.7%) |
| Age (yrs) | N | 51 | 50 | 50 | 52 | 51 |
|  | Mean | 22.61 | 20.66 | 21.98 | 20.38 | 22.20 |
|  | SD | 5.58 | 4.41 | 4.47 | 4.14 | 5.47 |
|  | Median | 21 | 20 | 22 | 19 | 20 |
|  | Range | 16~44 | 16~39 | 16~36 | 16~36 | 16~37 |
| Height (cm) | N | 51 | 50 | 50 | 52 | 51 |
|  | Mean | 172.53 | 168.76 | 168.30 | 170.01 | 171.49 |
|  | SD | 10.43 | 9.36 | 10.94 | 9.65 | 9.65 |
|  | Median | 172.72 | 167.64 | 168.91 | 170.18 | 170.18 |
|  | Range | 151.13~193.04 | 153.67~190.50 | 147.32~190.50 | 151.13~190.50 | 154.94~190.50 |
| Weight (kg) | N | 51 | 50 | 50 | 52 | 51 |
|  | Mean | 78.84 | 70.32 | 67.59 | 68.11 | 71.47 |
|  | SD | 18.51 | 16.57 | 14.20 | 13.31 | 17.81 |
|  | Median | 76.82 | 66.20 | 63.64 | 66.80 | 64.55 |
|  | Range | 45.45~142.50 | 45.45~113.64 | 47.27~111.36 | 50.00~124.32 | 41.36~122.73 |
| Ethnic Origin | Caucasian | 40 (78.4%) | 33 (66.0%) | 36 (72.0%) | 41 (78.8%) | 33 (64.7%) |
|  | Black | 2 (3.9%) | 1 (2.0%) | 2 (4.0%) | 2 (3.8%) | 6 (11.8%) |
|  | Hispanic | 8 (15.7%) | 14 (28.0%) | 11 (22.0%) | 8 (15.4%) | 10 (19.6%) |
|  | Asian | 0 (0.0%) | 0 (0.0%) | 1 (2.0%) | 0 (0.0%) | 0 (0.0%) |
|  | Other | 1 (2.0%) | 2 (4.0%) | 0 (0.0%) | 1 (1.9%) | 2 (3.9%) |

TABLE 3

Summary of Baseline Pain Intensity and Visual Analog Scale
Intent-To-Treat Subjects

|  | Group 5 | Group 4 | Group 1 | Group 2 | Group 3 |
|---|---|---|---|---|---|
|  | | | Treatments | | |
|  | Placebo with Placebo | T (50 mg) with Placebo | T (50 mg) with NTX (1 mg) | T (50 mg) with NTX (0.1 mg) | T (50 mg) with NTX (0.01 mg) |
| Number of Subjects | 51 | 50 | 50 | 52 | 51 |
| Baseline Pain Intensity | | | | | |
| None | 0 (0.0%) | 0 (0.0%) | 0 (0.0%) | 0 (0.0%) | 0 (0.0%) |
| Mild | 0 (0.0%) | 0 (0.0%) | 0 (0.0%) | 0 (0.0%) | 0 (0.0%) |
| Moderate | 35 (68.6%) | 35 (70.0%) | 34 (68.0%) | 36 (69.2%) | 36 (70.6%) |
| Severe | 16 (31.4%) | 15 (30.0%) | 16 (32.0%) | 16 (30.8%) | 15 (29.4%) |
| Baseline Visual Analog Scale | | | | | |
| N | 51 | 50 | 50 | 52 | 51 |
| Mean | 68.08 | 68.34 | 69.24 | 66.65 | 68.29 |
| SD | 12.47 | 12.38 | 12.23 | 13.44 | 11.34 |
| Median | 68 | 70 | 68 | 63 | 69 |
| Range | 47–100 | 36–99 | 48–100 | 45–96 | 45–100 |

Figure 14:
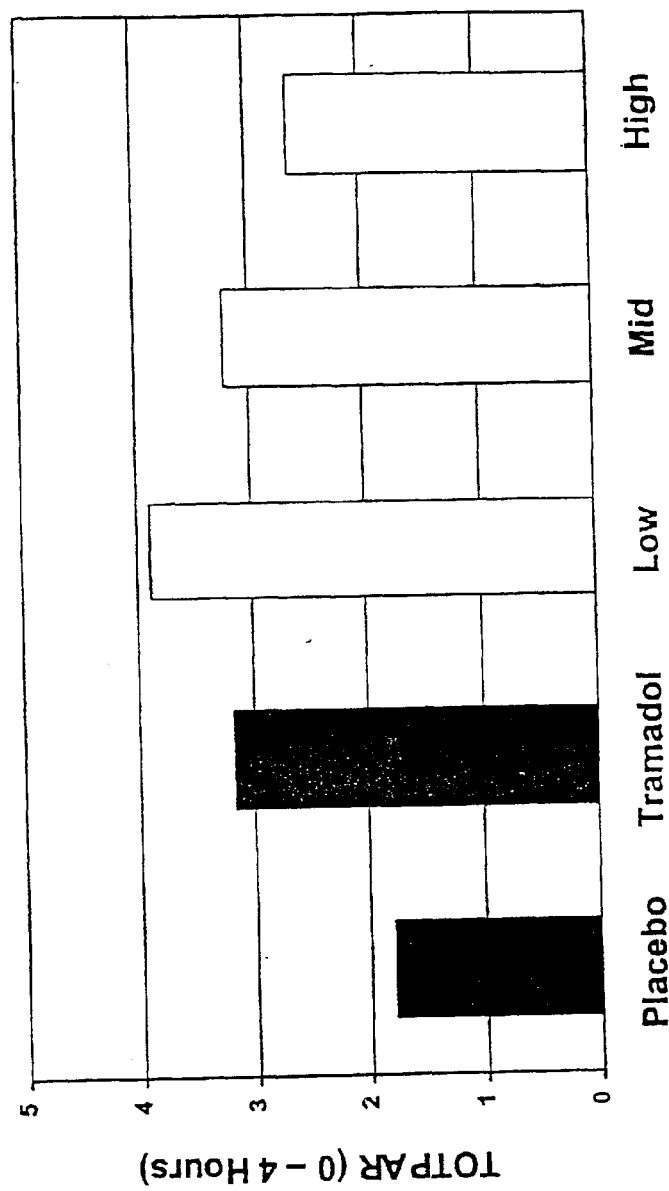
FIG. 14 represents the 4-hour Total Pain Relief Scores (TOTPAR) as presented in Table 4 for placebo (Group 5), tramadol (Group 4), "low" dose (0.01 mg) naltrexone (NTX) combination (Group 3), "mid" dose (0.1 mg) naltrexone combination (Group 2) and "high" dose (1.0 mg) naltrexone combination (Group 1).

The TOTPAR results are summarized in Table 4. The placebo treatment group had the lowest mean 4-hour TOTPAR scores (mean±SD=1.80±3.14) as shown in FIG. 14. All 4 of the active treatment groups exhibited mean 4-hour TOTPAR scores that were numerically higher than placebo. The combination treatments had a reverse dose-response relation in the mean 4-hour TOTPAR scores, i.e., the highest dose of NTX had the lowest mean 4-hour TOTPAR scores and the lowest dose of NTX had the highest mean 4-hour TOTPAR scores. The mean 4-hour TOTPAR scores for the 0.01-mg NTX and 0.1-mg NTX combination treatments were higher than that for the T alone treatment, whereas the 1.0-mg NTX combination treatment mean was lower than that for the T alone treatment.

Analyses of TOTPAR for the evaluable subgroup yielded results similar to those for the ITT population.

TABLE 4

Summary and Analysis of TOTPAR
Intent-To-Treat Subjects

|  | Group 5 | Group 4 | Group 1 | Group 2 | Group 3 |  |
|---|---|---|---|---|---|---|
|  | | | Treatments | | | |
|  | Placebo with Placebo | T (50 mg) with Placebo | T (50 mg) with NTX (1 mg) | T (50 mg) with NTX (0.1 mg) | T (50 mg) with NTX (0.01 mg) | Overall P-value[2] |
| Number of Subjects | 51 | 50 | 50 | 52 | 51 | |
| TOTPAR [1] up to 4 Hours | | | | | | |
| N | 51 | 50 | 50 | 52 | 51 | |
| Mean | 1.80 | 3.18 | 2.62 | 3.21 | 3.88 | |
| SD | 3.14 | 3.92 | 3.97 | 4.19 | 3.92 | |
| Median | 0 | 2 | 0 | 1 | 3 | |
| Range | 0~11 | 0~15 | 0~15 | 0~14 | 0~12 | |
| p-value of analysis against T[3] | | | 0.4672 | 0.9670 | 0.3596 | |
| p-value of analysis against Placebo[2] | | 0.0733 | 0.2872 | 0.0644 | 0.0068* | 0.0841 |
| TOTPAR up to 6 Hours | | | | | | |
| N | 51 | 50 | 50 | 52 | 51 | |
| Mean | 2.61 | 4.88 | 3.88 | 5.17 | 5.80 | |
| SD | 4.85 | 6.01 | 6.25 | 6.73 | 6.16 | |
| Median | 0 | 2 | 0 | 1 | 3 | |
| Range | 0~17 | 0~23 | 0~23 | 0~22 | 0~19 | |
| p-value of analysis against T[2] | | | 0.4082 | 0.8065 | 0.4425 | |
| p-value of analysis against Placebo[2] | | 0.0597 | 0.2906 | 0.0320* | 0.0080* | 0.0706 |
| TOTPAR up to 8 Hours | | | | | | |
| N | 51 | 50 | 50 | 52 | 51 | |
| Mean | 3.47 | 6.56 | 5.24 | 7.21 | 7.59 | |
| SD | 6.80 | 8.26 | 8.72 | 9.38 | 8.55 | |
| Median | 0 | 2 | 0 | 1 | 3 | |

TABLE 4-continued

Summary and Analysis of TOTPAR
Intent-To-Treat Subjects

|  | Group 5 | Group 4 | Group 1 | Group 2 | Group 3 | |
|---|---|---|---|---|---|---|
|  |  |  | Treatments |  |  |  |
|  | Placebo with Placebo | T (50 mg) with Placebo | T (50 mg) with NTX (1 mg) | T (50 mg) with NTX (0.1 mg) | T (50 mg) with NTX (0.01 mg) | Overall P-value[2] |
| Range | 0~23 | 0~31 | 0~31 | 0~30 | 0~26 |  |
| p-value of analysis against T[2] |  |  | 0.4321 | 0.6953 | 0.5385 |  |
| p-value of analysis against Placebo[2] |  | 0.0654 | 0.2902 | 0.0245* | 0.0138* | 0.0886 |

[1]Pain Relief Scores (PAR): 0 = None, 1 = A little, 2 = Some, 3 = A lot, 4 = Complete.
TOTPAR up to 4 hours is defined as sum of Pain Relief Scores from 0.5 hour to 4 hour.
TOTPAR up to 6 hours is defined as sum of Pain Relief Scores from 0.5 hour to 6 hour.
TOTPAR up to 8 hours is defined as sum of Pain Relief Scores from 0.5 hour to 8 hour.
P-values comparing all five treatment groups and pairwise comparisons are determined using ANOVA. Reference: Appendix D1.1
[2]Significance is at 0.05 nominal level.
[3]Significance for pairwise comparisons is determined using Hochberg's procedure.
Last Observation Carried Forward method is used to impute missing values for ITT population.

Table 5 summarizes the results of the 4, 6, and 8-hour SPID results. The placebo treatment had the lowest mean 4-hour SPID scores (−1.24±2.94). All 4 of the active treatment groups exhibited improved profiles in mean 4-hour SPID relative to placebo. The mean 4-hour SPID scores for the 0.01-mg NTX and 0.1-mg NTX combination treatments were higher than that for the T alone treatment, whereas the 1.0-mg NTX combination treatment was lower than that for the T alone treatment.

The patterns of the 6-hour and 8-hour SPID scores were similar to those at 4 hours. Analyses of SPID for the evaluable subgroup also yielded profiles that were similar to those found in the ITT population.

TABLE 5

Summary and Analysis of SPID
Intent-To-Treat Subjects

|  | Group 5 | Group 4 | Group 1 | Group 2 | Group 3 | |
|---|---|---|---|---|---|---|
|  |  |  | Treatments |  |  |  |
|  | Placebo with Placebo | T (50 mg) with Placebo | T (50 mg) with NTX (1 mg) | T (50 mg) with NTX (0.1 mg) | T (50 mg) with NTX (0.01 mg) | Overall P-value[2] |
| Number of Subjects | 51 | 50 | 50 | 52 | 51 |  |
| SPID[1] up to 4 Hours |  |  |  |  |  |  |
| N | 51 | 50 | 50 | 52 | 51 |  |
| Mean | −1.24 | −0.58 | −0.64 | 0.13 | 0.04 |  |
| SD | 2.94 | 3.27 | 3.10 | 3.28 | 3.10 |  |
| Median | 0 | 0 | 0 | 0 | 0 |  |
| Range | −5~6 | −5~7 | −5~9 | −5~8 | −5~7 |  |
| p-value of analysis against T[3] |  |  | 0.9240 | 0.2516 | 0.3227 |  |
| p-value of analysis against Placebo[2] |  | 0.2954 | 0.3417 | 0.0277* | 0.0414* | 0.1685 |
| SPID up to 6 Hours |  |  |  |  |  |  |
| N | 51 | 50 | 50 | 52 | 51 |  |
| Mean | −1.76 | −0.54 | −0.72 | 0.46 | 0.33 |  |
| SD | 4.48 | 4.96 | 5.02 | 4.98 | 4.77 |  |
| Median | 0 | 0 | 0 | 0 | 0 |  |
| Range | −7~10 | −7~11 | −7~15 | −7~12 | −7~12 |  |
| p-value of analysis against T[2] |  |  | 0.8527 | 0.2975 | 0.3658 |  |
| p-value of analysis against Placebo[2] |  | 0.2051 | 0.2795 | 0.0205* | 0.0297* | 0.1342 |
| SPID up to 8 Hours |  |  |  |  |  |  |
| N | 51 | 50 | 50 | 52 | 51 |  |
| Mean | −2.24 | −0.54 | −0.84 | 0.87 | 0.49 |  |
| SD | 6.19 | 6.64 | 7.03 | 6.80 | 6.37 |  |
| Median | 0 | 0 | 0 | 0 | 0 |  |
| Range | −9~16 | −9~15 | −9~21 | −9~16 | −9~16 |  |

TABLE 5-continued

Summary and Analysis of SPID
Intent-To-Treat Subjects

| | Group 5 | Group 4 | Group 1 | Group 2 | Group 3 | |
|---|---|---|---|---|---|---|
| | | | Treatments | | | |
| | Placebo with Placebo | T (50 mg) with Placebo | T (50 mg) with NTX (1 mg) | T (50 mg) with NTX (0.1 mg) | T (50 mg) with NTX (0.01 mg) | Overall P-value[2] |
| p-value of analysis against T[2] | | | 0.8207 | 0.2842 | 0.4344 | |
| p-value of analysis against Placebo[2] | | 0.1988 | 0.2900 | 0.0181* | 0.0384 | 0.1400 |

[1]Pain Intensity Score: 0 = None, 1 = Mild, 2 = Moderate, 3 = Severe. The Pain Intensity Difference (PID) at each time point is calculated as the difference between the Pain Intensity Score at Hour 0 and the score at observation time.
SPID up to 4 hours is defined as sum of Pain Intensity Score Differences from 0.5 hour to 4 hour.
SPID up to 6 hours is defined as sum of Pain Intensity Score Differences from 0.5 hour to 6 hour.
SPID up to 8 hours is defined as sum of Pain Intensity Score Differences from 0.5 hour to 8 hour.
P-values comparing all five treatment groups and pairwise comparisons are determined using ANOVA. Reference: Appendix D2. 1
[2]Significance is at 0.05 nominal level.
[3]Significance for pairwise comparisons is determined using Hochberg's procedure. Last Observation Carried Forward method is used to impute missing values for ITT population.

Table 6 summarizes the results of the 4, 6, and 8 hour Visual Analog Scale SPID results. The placebo treatment had the lowest mean 4-hour VAS-SPID scores with a mean of −44.98 and a standard deviation of 92.76.

The 4 active treatment groups exhibited mean VAS-SPID scores that were higher than that for the placebo. The mean 4-hour VAS-SPID for the 3 NTX combination treatments was higher than that for T alone.

The profiles of 6-hour and 8-hour VAS-SPID scores were similar to those at 4 hours.

TABLE 6

Summary and Analysis of Visual Analog Scale-SPID
Intent-To-Treat Subjects

| | Group 5 | Group 4 | Group 1 | Group 2 | Group 3 | |
|---|---|---|---|---|---|---|
| | | | Treatments | | | |
| | Placebo with Placebo | T (50 mg) with Placebo | T (50 mg) with NTX (1 mg) | T (50 mg) with NTX (0.1 mg) | T (50 mg) with NTX (0.01 mg) | Overall P-value[2] |
| Number of Subjects | 51 | 50 | 50 | 52 | 51 | |
| VAS-SPID[1] up to 4 Hours | | | | | | |
| N | 51 | 50 | 50 | 52 | 51 | |
| Mean | −44.98 | −16.54 | −12.58 | 0.21 | 10.51 | |
| SD | 92.76 | 122.18 | 89.53 | 104.91 | 93.90 | |
| Median | −62 | −19 | −17 | −10 | 7 | |
| Range | −208~224 | −215~300 | −135~262 | −185~313 | −155~265 | |
| p-value of analysis against T[3] | | | 0.8452 | 0.4047 | 0.1810 | |
| p-value of analysis against Placebo[2] | | 0.1597 | 0.1094 | 0.0245* | 0.0061* | 0.0704 |
| VAS-SPID up to 6 Hours | | | | | | |
| N | 51 | 50 | 50 | 52 | 51 | |
| Mean | −63.39 | −14.02 | −13.46 | 8.96 | 25.27 | |
| SD | 144.17 | 189.30 | 146.37 | 162.94 | 154.92 | |
| Median | −89 | −18 | −32 | −3 | 7 | |
| Range | −294~390 | −311~440 | −205~433 | −279~487 | −225~445 | |
| p-value of analysis against T[2] | | | 0.9861 | 0.4699 | 0.2192 | |
| p-value of analysis against Placebo[2] | | 0.1230 | 0.1188 | 0.0228* | 0.0056* | 0.0670 |
| VAS-SPID up to 8 Hours | | | | | | |
| N | 51 | 50 | 50 | 52 | 51 | |
| Mean | −79.20 | −15.14 | −13.74 | 21.10 | 38.47 | |
| SD | 201.83 | 254.21 | 206.77 | 224.70 | 217.68 | |
| Median | −115 | −27 | −45 | 2 | 0 | |
| Range | −395~555 | −407~580 | −285~605 | −373~661 | −297~610 | |

TABLE 6-continued

Summary and Analysis of Visual Analog Scale-SPID
Intent-To-Treat Subjects

|  | Group 5 | Group 4 | Group 1 | Group 2 | Group 3 | |
| --- | --- | --- | --- | --- | --- | --- |
|  | | | Treatments | | | |
|  | Placebo with Placebo | T (50 mg) with Placebo | T (50 mg) with NTX (1 mg) | T (50 mg) with NTX (0.1 mg) | T (50 mg) with NTX (0.01 mg) | Overall P-value[2] |
| p-value of analysis against T[2] | | | 0.9748 | 0.4101 | 0.2256 | |
| p-value of analysis against Placebo[2] | | 0.1479 | 0.1393 | 0.0226* | 0.0079 | 0.0793 |

[1]The Visual Analog Scale Difference (VAS-PID) at each time point is calculated as the difference between the Visual Analog Scale and Hour 0 and the score at observation time.
VAS-SPID up to 4 hours is defined as sum of Visual Analog Scale Differences from 0.5 hour to 4 hour.
VAS-SPID up to 6 hours is defined as sum of Visual Analog Scale Differences from 0.5 hour to 6 hour.
VAS-SPID up to 8 hours is defined as sum of Visual Analog Scale Differences from 0.5 hour to 8 hour.
P-values comparing all five treatment groups and pairwise comparisons are determined using ANOVA. Reference: Appendix D4.1
[2]Significance is at 0.05 nominal level.
[3]Significance for pairwise comparisons is determined using Hochberg's procedure. Last Oservation Carried Forward method is used to impute missing values for ITT population.

Figure 15:
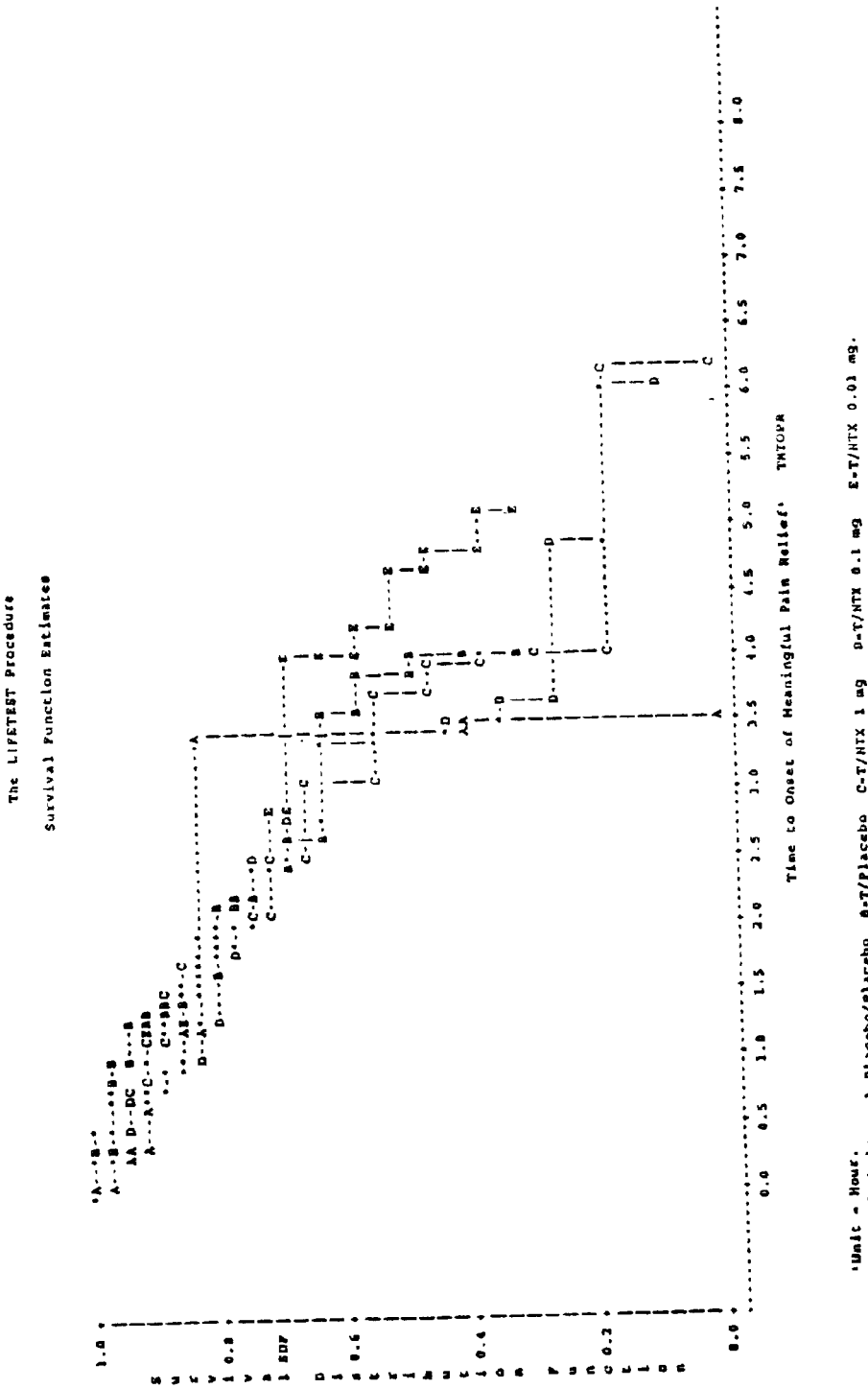
FIG. 15 represents the time to onset of meaningful pain relief scores as presented in Table 7 where A=placebo (Group 5); B=tramadol (Group 4); C=tramadol with 1.0 mg NTX (Group 1); D=tramadol with 0.1 mg NTX (Group 2); E=tramadol with 0.01 mg NTX (Group 3).

FIG. 15 is a visual presentation of the summary and analysis of time to onset of meaningful pain relief scores presented in Table 7. The median times to onset of meaningful pain relief ranged from 3.45 hours for placebo to 4.65 hours for the 0.01-mg NTX combination treatment. The placebo treatment had the lowest number of subjects who reached meaningful pain relief. In addition, all the combination treatment groups had higher numbers of subjects reaching meaningful pain relief than did the group that received T alone.

Analyses of times to onset of meaningful pain relief for the evaluable subgroup yielded similar result.

Figure 16:
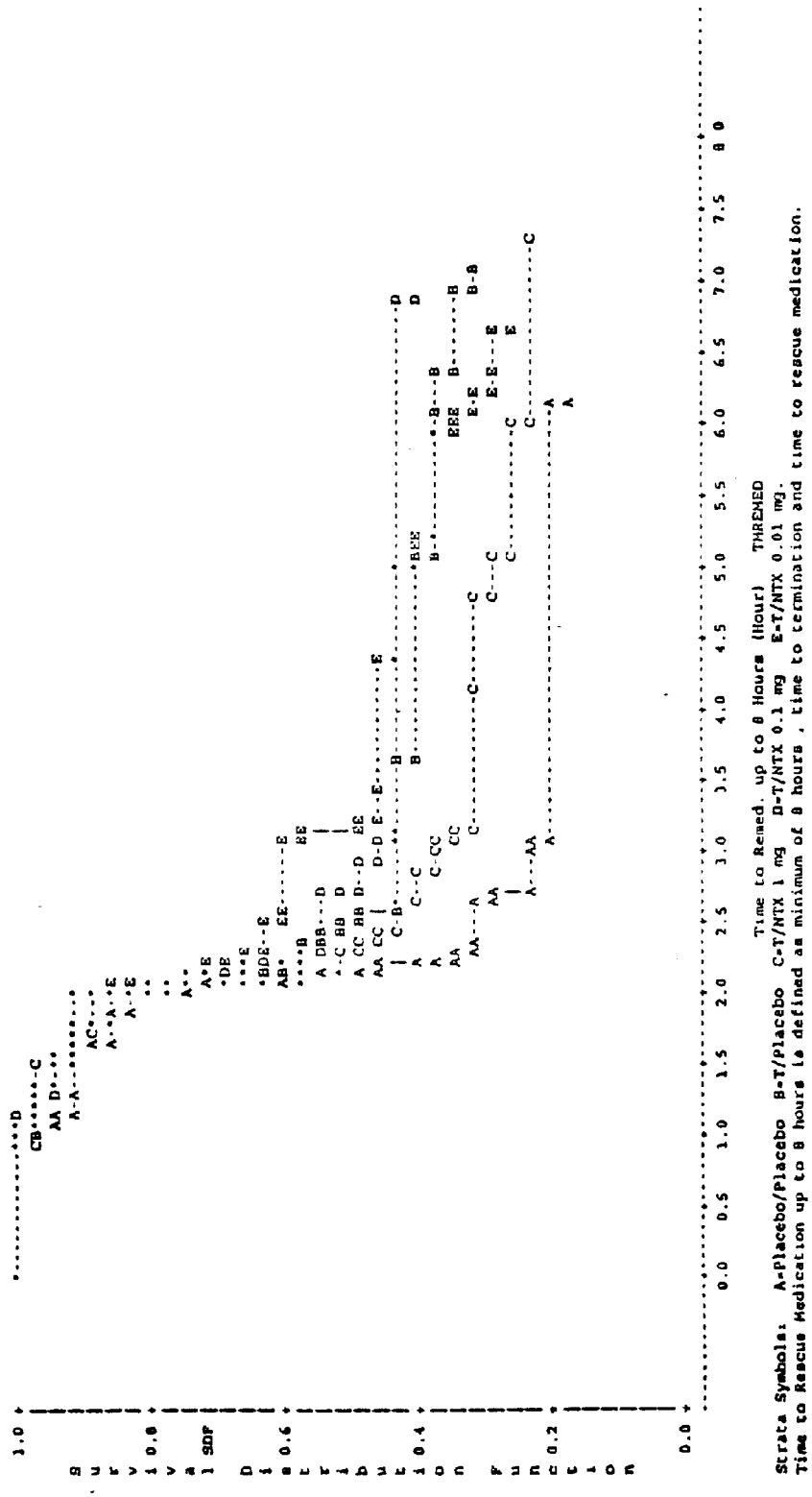
FIG. 16 represents the time to remedication up to 8 hours as presented in Table 8 where A-E represent the same groups as in FIG. 15.

FIG. 16 is a visual presentation of the summary and analysis of time to remedication up to 8 and 24 hours presented in Table 8. The median times to remedication up to 8 hours ranged from 2.15 hours for placebo to 3.17 hours for the 0.01-mg NTX combination treatment. By the end of 8 hours, the numbers of subjects who had taken remedication were comparable among all treatment groups.

Analyses of time to remedication up to 24 hours yielded similar results, however, the data should be viewed with caution because subjects were not under close supervision after 8 hours. Analyses for the evaluable subjects yielded results similar to those for the ITT population.

TABLE 7

Summary and Analysis of Time to Onset of Meaningful Pain Relief
Intent-To-Treat Subjects

|  | Group 5 | Group 4 | Group 1 | Group 2 | Group 3 | |
| --- | --- | --- | --- | --- | --- | --- |
|  | | | Treatments | | | |
|  | Placebo with Placebo | T (50 mg) with Placebo | T (50 mg) with NTX (1 mg) | T (50 mg) with NTX (0.1 mg) | T (50 mg) with NTX (0.01 mg) | Overall P-value[2] |
| Number of Subjects | 51 | 50 | 50 | 52 | 51 | |
| Time to Onset of Meaningful Pain Relief (Hour) | | | | | | |
| N | 51 | 50 | 50 | 52 | 51 | |
| Number of Subjects with Meaningful Pain Relief | 11 | 17 | 20 | 21 | 20 | |
| Number of Subjects Censored | 40 | 33 | 30 | 31 | 31 | |
| Median | 3.45 | 3.85 | 3.70 | 3.45 | 4.65 | |
| Range | 0.07~3.50 | 0.35~8.00 | 0.52~6.13 | 0.25~8.00 | 0.50~6.63 | |
| p-value of analysis against T[3] | | | 0.2985 | 0.2400 | 0.8613 | |
| p-value of analysis against Placebo[2] | | 0.8327 | 0.7287 | 0.5635 | 0.9170 | 0.4706 |

N and Range are based on both censored and non-censored observations.
Median is calculated from Kaplan-Meier curve.
[1]P-value of comparison among all 5 treatment groups and p-values of pairwise comparisons are determined using Log Rank test. Reference: Appendix D5, FIG. 5Significance for pairwise comparisons is determined using Hochberg's procedure.
[3]Significance is at 0.05 nominal level.

TABLE 8

Summary and Analysis of Time to Remediation up to 8 and 24 Hours
Intent-To-Treat Subjects

|  | Group 5 | Group 4 | Group 1 | Group 2 | Group 3 |  |
|---|---|---|---|---|---|---|
|  | Treatments | | | | | |
|  | Placebo with Placebo | T (50 mg) with Placebo | T (50 mg) with NTX (1 mg) | T (50 mg) with NTX (0.1 mg) | T (50 mg) with NTX (0.01 mg) | Overall P-value[2] |
| Number of Subjects | 51 | 50 | 50 | 52 | 51 | |
| Time to Remediation up to 8 Hours (Hours) | | | | | | |
| N | 51 | 50 | 50 | 52 | 51 | |
| Number of Subjects taken Rescue Medication | 41 | 35 | 39 | 31 | 38 | |
| Number of Subjects Censored | 10 | 15 | 11 | 21 | 13 | |
| Median | 2.15 | 2.48 | 2.24 | 2.72 | 3.17 | |
| Range | 1.05~8.00 | 1.02~8.00 | 0.92~8.00 | 1.13~8.00 | 1.10~8.00 | |
| p-value of analysis against T[3] | | | 0.3553 | 0.3761 | 0.9730 | |
| p-value of analysis against Placebo[2] | | 0.0625 | 0.3056 | 0.0072* | 0.0145* | 0.0345* |
| Time to Remediation up to 24 Hours (Hours) | | | | | | |
| N | 51 | 50 | 50 | 52 | 51 | |
| Number of Subjects taken Rescue Medication | 47 | 42 | 44 | 46 | 49 | |
| Number of Subjects Censored | 4 | 8 | 6 | 6 | 2 | |
| Median | 2.13 | 2.48 | 2.24 | 2.70 | 3.17 | |
| Range | 1.05~24.00 | 1.02~24.00 | 0.92~24.00 | 1.13~24.00 | 1.10~24.00 | |
| p-value of analysis against T[3] | | | 0.4264 | 0.8779 | 0.4214 | |
| p-value of analysis against Placebo[2] | | 0.0517 | 0.2122 | 0.0283* | 0.0852 | 0.1375 |

Time to Remediation up to 8 hours is defined as minimum of 8 hours, time to termination and time to rescue medication. Time to Remediation up to 24 hours is defined as minimum of 24 hours and time to rescue medication. N and Range are based on both censored and non-censored observations. Median is calculated from Kaplan-Meier curve.
[1]P-value of comparison among all 5 treatment groups and p-values of pairwise comparisons are determined using Log Rank test. Reference: Appendix D11, FIG. 6Significance for pairwise comparisons is determined using Hochberg's procedure.
[3]Significance is at 0.05 nominal level.

Figure 17:
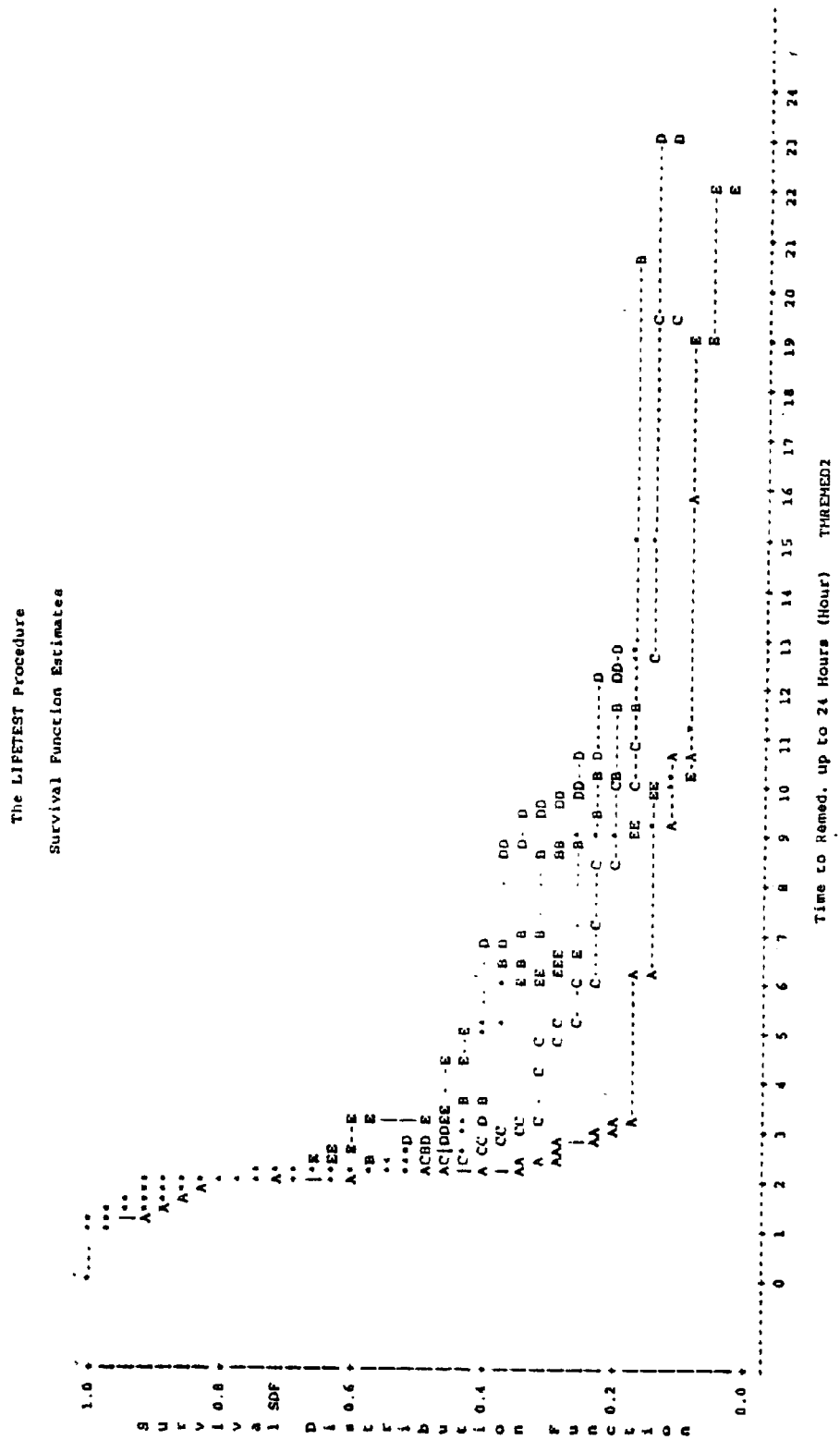
FIG. 17 represents the time to remedication up to 24 hours as presented in Table 9 where A-E represent the same groups as in FIG. 16.

FIG. 17 is a visual presentation of the summary and analysis of percent of subjects who took remedication up to 8 and 24 hours presented in Table 9. The percentage of subjects who remedicated within 8 hours ranged from 61.5% for the 0.1-mg NTX group to 84.3% for the placebo group.

Analyses of the percentage of subjects who remedicated within 24 hours indicated that all 5 treatment groups were comparable, however, the data should be interpreted with caution because subjects were not under close supervision after 8 hours. Analyses for the evaluable subjects led to conclusions similar to those for the ITT population.

TABLE 9

Summary and Analysis of Percent of Subjects who Took Remediation up to 8 and 24 Hours
Intent-to-Treat Subjects

|  | Treatments | | | | | |
|---|---|---|---|---|---|---|
|  | Placebo with Placebo | T (50 mg) with Placebo | T (50 mg) with NTX (1 mg) | T (50 mg) with NTX (0.1 mg) | T (50 mg) with NTX (0.01 mg) | Overall P-value[1] |
| Number of Subjects | 51 | 50 | 50 | 52 | 51 | |
| Percent of Subject who take Remediation up to 8 hours | | | | | | |
| Yes | 43 (84.3%) | 35 (70.0%) | 39 (78.0%) | 32 (61.5%) | 38 (74.5%) | |
| No | 8 (15.7%) | 15 (30.0%) | 11 (22.0%) | 20 (38.5%) | 13 (25.5%) | |
| p-value of analysis against T | | | 0.4945 | 0.4091 | 0.6611 | |
| p-value of analysis against Placebo | | 0.1011 | 0.4550 | 0.0142* | 0.3275 | 0.1037 |
| Percent of Subject who take Remediation up to 8 hours | | | | | | |
| Yes | 47 (92.2%) | 42 (84.0%) | 44 (88.0%) | 46 (88.5%) | 49 (96.1%) | |
| No | 4 (7.8%) | 8 (16.0%) | 6 (12.0%) | 6 (11.5%) | 2 (3.9%) | |
| p-value of analysis against T | | | 0.7742 | 0.5741 | 0.0514 | |
| p-value of analysis against Placebo | | 0.2343 | 0.5251 | 0.7412 | 0.6779 | 0.3032 |

YES or NO is determined from medication page.
[1]P-values of comparison among treatment groups and p-values of pairwise comparison are determined using Fisher's Exact test.
*Significance is at 0.05 nominal level.

Figure 18:
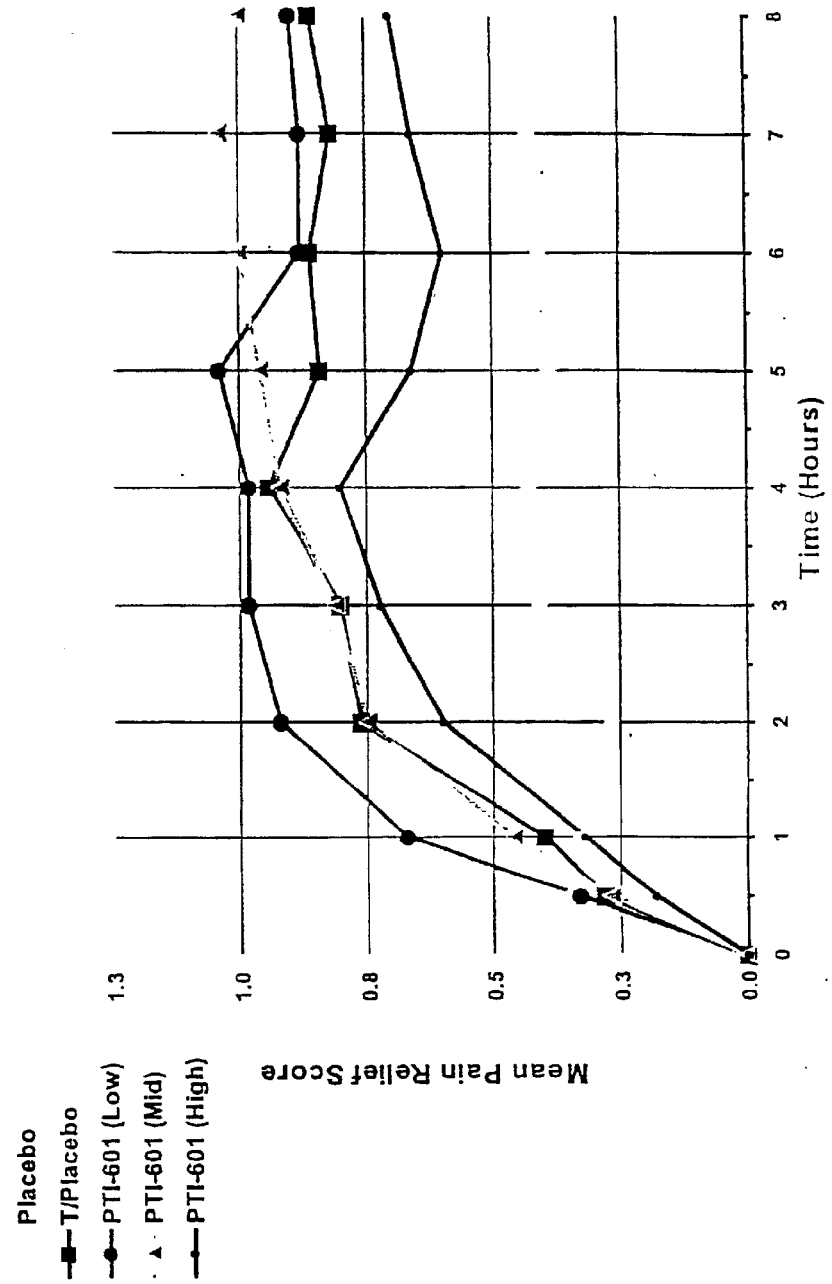
FIGS. 18 and 19 represent hourly pain relief scores from 0–8 and 0–4 hours, respectively, as presented in Table 10, where A or small diamonds (◇) represent placebo (Group 5); B or squares (□) represent tramadol (Group 4); E or larger circles (○) represent tramadol with 0.01 mg NTX (Group 3); D or triangles (Δ) represent tramadol with 0.1 mg NTX (Group 2); C or small circles (o) represent tramadol with 1.0 mg NTX (Group 1), and where the pain relief score 0=none; 1=a little; 2=some; 3=a lot; and 4=complete.
Figure 19:
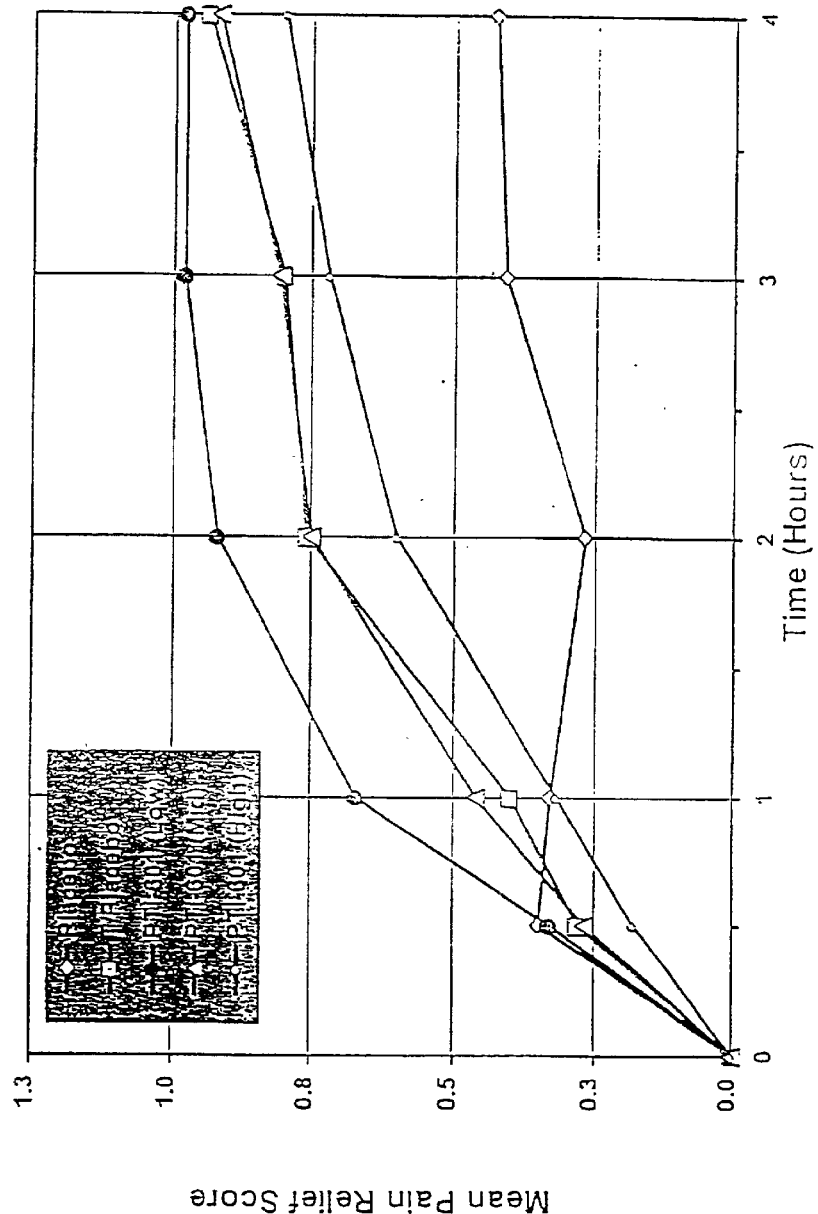

FIGS. 18 and 19 are visual presentations of the hourly pain relief scores presented in Table 10. The hourly pain relief scores were summarized and analyzed in 2 ways: first as a categorical variable and second as a numerical variable. Because results of these two methods were similar, only the results from the numerical version are presented here. Whereas the hourly pain relief scores for the placebo treatment were generally flat, those for the active treatment groups were generally improving over time. There was separation between the placebo and the active treatment groups that continued throughout the 8-hour study period.

TABLE 10

Summary and Analysis of Hourly Pain Relief Scores - PAR as a numerical variable
Intent-To-Treat Subjects

| | Group 5 | Group 4 | Group 1 | Group 2 | Group 3 | |
| --- | --- | --- | --- | --- | --- | --- |
| | | | Treatments | | | |
| | Placebo with Placebo | T (50 mg) with Placebo | T (50 mg) with NTX (1 mg) | T (50 mg) with NTX (0.1 mg) | T (50 mg) with NTX (0.01 mg) | Overall P-value[2] |
| Number of Subjects | 51 | 50 | 50 | 52 | 51 | |
| Hour 0.5 | | | | | | |
| N | 51 | 50 | 50 | 52 | 51 | |
| Mean | 0.35 | 0.28 | 0.18 | 0.27 | 0.33 | |
| SD | 0.66 | 0.54 | 0.44 | 0.56 | 0.59 | |
| Median | 0 | 0 | 0 | 0 | 0 | |
| Range | 0–2 | 0–2 | 0–2 | 0–2 | 0–2 | |
| p-value of analysis against T | | | 0.3746 | 0.9230 | 0.6340 | 0.5739 |
| p-value of analysis against Placebo | | 0.5150 | 0.1234 | 0.4506 | 0.8603 | |
| Hour 1 | | | | | | |
| N | 51 | 50 | 50 | 52 | 51 | |
| Mean | 0.33 | 0.40 | 0.32 | 0.46 | 0.67 | |
| SD | 0.62 | 0.78 | 0.62 | 0.80 | 0.89 | |
| Median | 0 | 0 | 0 | 0 | 0 | |
| Range | 0–2 | 0–3 | 0–2 | 0–3 | 0–3 | |
| p-value of analysis against T | | | 0.5948 | 0.6795 | 0.0756 | |
| p-value of analysis against Placebo | | 0.6560 | 0.9290 | 0.3873 | 0.0259* | 0.1328 |
| Hour 2 | | | | | | |
| N | 51 | 50 | 50 | 52 | 51 | |
| Mean | 0.27 | 0.76 | 0.60 | 0.75 | 0.92 | |
| SD | 0.67 | 1.04 | 1.09 | 1.05 | 1.00 | |
| Median | 0 | 0 | 0 | 0 | 1 | |
| Range | 0–3 | 0–4 | 0–4 | 0–3 | 0–3 | |
| p-value of analysis against T | | | 0.4147 | 0.9589 | 0.4078 | |
| p-value of analysis against Placebo | | 0.0134* | 0.0961 | 0.0144* | 0.0010* | 0.0144* |
| Hour 3 | | | | | | |
| N | 51 | 50 | 50 | 52 | 51 | |
| Mean | 0.41 | 0.80 | 0.72 | 0.81 | 0.98 | |
| SD | 0.90 | 1.14 | 1.21 | 1.17 | 1.14 | |
| Median | 0 | 0 | 0 | 0 | 1 | |
| Range | 0–3 | 0–4 | 0–4 | 0–4 | 0–3 | |
| p-value of analysis against T | | | 0.7209 | 0.9723 | 0.4185 | |
| p-value of analysis against Placebo | | 0.0824 | 0.1674 | 0.0737 | 0.0108* | 0.1346 |
| Hour 4 | | | | | | |
| N | 51 | 50 | 50 | 52 | 51 | |
| Mean | 0.43 | 0.94 | 0.80 | 0.92 | 0.98 | |
| SD | 0.94 | 1.22 | 1.34 | 1.38 | 1.26 | |
| Median | 0 | 0 | 0 | 0 | 0 | |
| Range | 0–3 | 0–4 | 0–4 | 0–4 | 0–4 | |
| p-value of analysis against T | | | 0.5725 | 0.9451 | 0.8700 | |
| p-value of analysis against Placebo | | 0.0401* | 0.1361 | 0.0450* | 0.0261* | 0.1555 |
| Hour 5 | | | | | | |
| N | 51 | 50 | 50 | 52 | 51 | |
| Mean | 0.39 | 0.84 | 0.66 | 0.96 | 1.04 | |
| SD | 0.87 | 1.15 | 1.27 | 1.41 | 1.34 | |
| Median | 0 | 0 | 0 | 0 | 0 | |
| Range | 0–3 | 0–4 | 0–4 | 0–4 | 0–4 | |
| p-value of analysis against T | | | 0.4634 | 0.6170 | 0.4148 | |
| p-value of analysis against Placebo | | 0.0675 | 0.2732 | 0.0192* | 0.0082* | 0.0610 |
| Hour 6 | | | | | | |
| N | 51 | 50 | 50 | 52 | 51 | |
| Mean | 0.41 | 0.86 | 0.60 | 1.00 | 0.88 | |
| SD | 0.96 | 1.23 | 1.29 | 1.44 | 1.28 | |
| Median | 0 | 0 | 0 | 0 | 0 | |
| Range | 0–3 | 0–4 | 0–4 | 0–4 | 0–3 | |

TABLE 10-continued

Summary and Analysis of Hourly Pain Relief Scores - PAR as a numerical variable
Intent-To-Treat Subjects

|  | Group 5 | Group 4 | Group 1 | Group 2 | Group 3 | |
| --- | --- | --- | --- | --- | --- | --- |
|  | | | Treatments | | | |
|  | Placebo with Placebo | T (50 mg) with Placebo | T (50 mg) with NTX (1 mg) | T (50 mg) with NTX (0.1 mg) | T (50 mg) with NTX (0.01 mg) | Overall P-value[2] |
| p-value of analysis against T | | | 0.2997 | 0.5726 | 0.9285 | |
| p-value of analysis against Placebo | | 0.0730 | 0.4503 | 0.0178* | 0.0586 | 0.1162 |
| Hour 7 | | | | | | |
| N | 51 | 50 | 50 | 52 | 51 | |
| Mean | 0.43 | 0.82 | 0.66 | 1.04 | 0.88 | |
| SD | 1.02 | 1.26 | 1.33 | 1.47 | 1.31 | |
| Median | 0 | 0 | 0 | 0 | 0 | |
| Range | 0–4 | 0–4 | 0–4 | 0–4 | 0–4 | |
| p-value of analysis against T | | | 0.5347 | 0.3922 | 0.8078 | |
| p-value of analysis against Placebo | | 0.1304 | 0.3729 | 0.0174* | 0.0780 | 0.1609 |
| Hour 8 | | | | | | |
| N | 51 | 50 | 50 | 52 | 51 | |
| Mean | 0.43 | 0.86 | 0.70 | 1.00 | 0.90 | |
| SD | 1.02 | 1.29 | 1.36 | 1.46 | 1.33 | |
| Median | 0 | 0 | 0 | 0 | 0 | |
| Range | 0–4 | 0–4 | 0–4 | 0–4 | 0–4 | |
| p-value of analysis against T | | | 0.5392 | 0.5874 | 0.8714 | |
| p-value of analysis against Placebo | | 0.0991 | 0.3006 | 0.0275* | 0.0690 | 0.2046 |

Pain Relief Scores (PAR): 0 = None, 1 = A little; 3 - A lot; 4 = Complete.
[1]P-values comparing all 5 treatment groups and pairwise comparisons are determined using ANOVA. Reference: Appendix D15.1 and FIG. 4.1
*Significance is at 0.05 nominal level. Last Observation Carried Forward method is used to impute missing values for ITT population.

Figure 20:
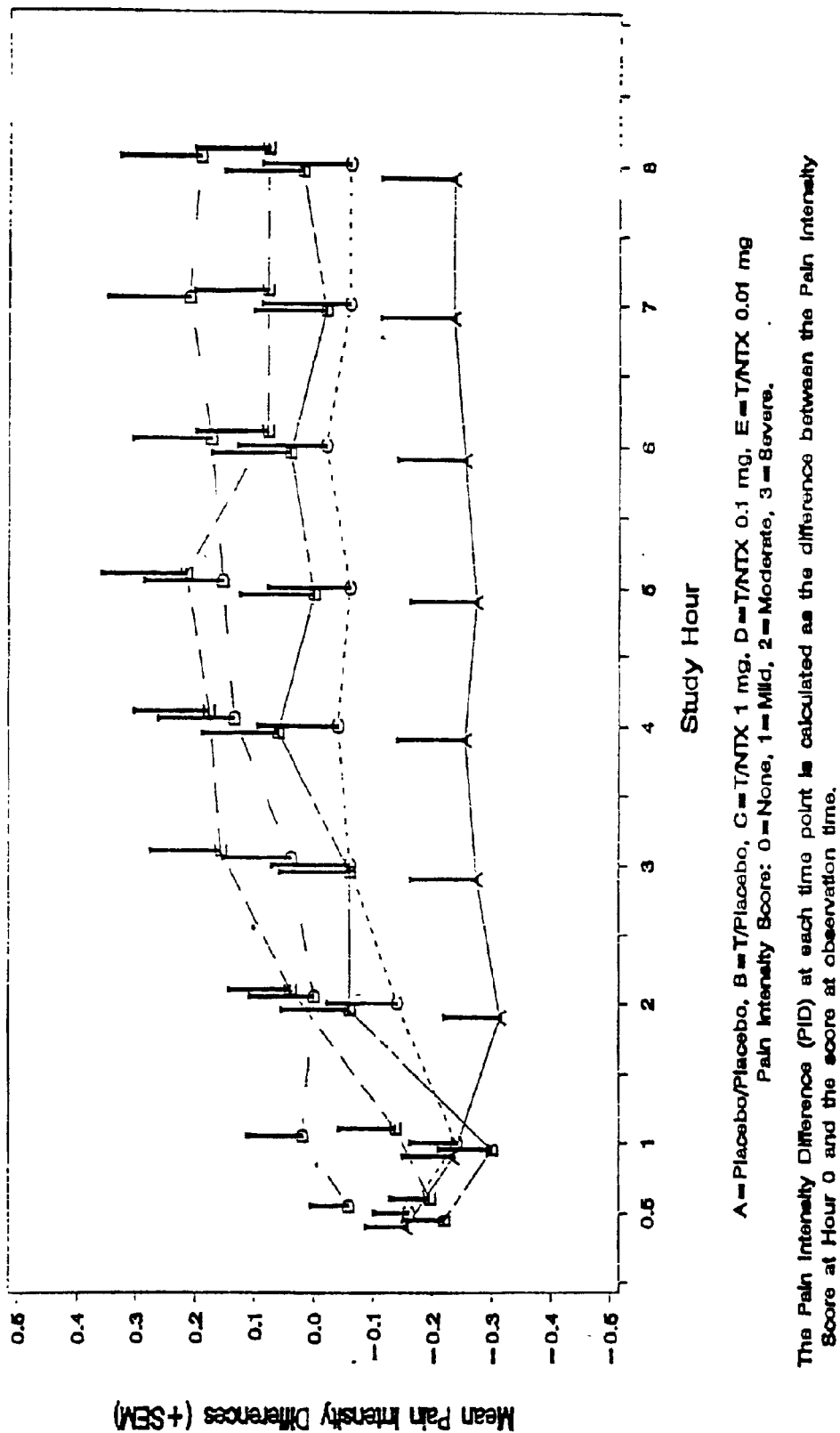
FIG. 20 represents hourly pain intensity different (PID) scores as presented in Table 11 where A-E represent the same groups as in FIG. 15 and where the pain intensity score of 0=none; 1=mild; 2 moderate and 3=severe and where PID at each time point is calculated as the difference between the pain intensity score at 0 hour and the score at the observation time (study hour).

The hourly PID scores were summarized and analyzed 2 ways: first as a categorical variable and second as a numerical variable. Only the results from the numerical version are presented here. FIG. 20 summarizes the hourly PID data presented in Table 11. The hourly PID scores for the placebo treatment were generally flat while the hourly PID scores generally improved over time for the active treatment groups. The 4 active treatment groups were comparable in analgesic response. The 0.1-mg NTX combination was statistically superior to placebo at hour 1 only and approached statistical significance at hour 0.5. At hour 1, 2, 4, 5, 6, 7, and 8 the 0.1-mg NTX combination was superior to placebo. The 0.01-mg NTX combination was superior to placebo at hours 2, 3, 4, and 5. No other time points were found to be statistically different to placebo for all other treatment groups.

TABLE 11

Summary and Analysis of Hourly Pain Intensity Difference Scores - PID as a numerical variable
Intent-To-Treat Subjects

|  | Group 5 | Group 4 | Group 1 | Group 2 | Group 3 | |
| --- | --- | --- | --- | --- | --- | --- |
|  | | | Treatments | | | |
|  | Placebo with Placebo | T (50 mg) with Placebo | T (50 mg) with NTX (1 mg) | T (50 mg) with NTX (0.1 mg) | T (50 mg) with NTX (0.01 mg) | Overall P-value[2] |
| Number of Subjects | 51 | 50 | 50 | 52 | 51 | |
| Hour 0.5 | | | | | | |
| N | 51 | 50 | 50 | 52 | 51 | |
| Mean | −0.16 | −0.22 | −0.16 | −0.06 | −0.20 | |
| SD | 0.50 | 0.51 | 0.42 | 0.46 | 0.49 | |
| Median | 0 | 0 | 0 | 0 | 0 | |
| Range | −1–1 | −1–1 | −1–1 | −1–1 | −1–1 | |
| p-value of analysis against T | | | 0.5309 | 0.0878 | 0.8017 | |
| p-value of analysis against Placebo | | 0.5076 | 0.9737 | 0.2936 | 0.6791 | 0.4864 |
| Hour 1 | | | | | | |
| N | 51 | 50 | 50 | 52 | 51 | |
| Mean | −0.24 | −0.30 | −0.24 | 0.02 | −0.14 | |
| SD | 0.62 | 0.65 | 0.56 | 0.67 | 0.69 | |
| Median | 0 | 0 | 0 | 0 | 0 | |
| Range | −1–1 | −1–1 | −1–1 | −1–1 | −1–2 | |
| p-value of analysis against T | | | 0.6394 | 0.0123* | 0.2022 | |
| p-value of analysis against Placebo | | 0.6116 | 0.9705 | 0.0445* | 0.4395 | 0.1007 |

TABLE 11-continued

Summary and Analysis of Hourly Pain Intensity Difference Scores - PID as a numerical variable
Intent-To-Treat Subjects

|  | Group 5 | Group 4 | Group 1 | Group 2 | Group 3 | |
|---|---|---|---|---|---|---|
|  |  |  | Treatments |  |  |  |
|  | Placebo with Placebo | T (50 mg) with Placebo | T (50 mg) with NTX (1 mg) | T (50 mg) with NTX (0.1 mg) | T (50 mg) with NTX (0.01 mg) | Overall P-value[2] |
| Hour 2 |  |  |  |  |  |  |
| N | 51 | 50 | 50 | 52 | 51 |  |
| Mean | −0.31 | −0.06 | −0.14 | 0.00 | 0.04 |  |
| SD | 0.68 | 0.82 | 0.83 | 0 | 0.75 |  |
| Median | 0 | 0 | 0 | 0.79 | 0 |  |
| Range | −1–1 | −1–2 | −1–3 | −1–2 | −1–2 |  |
| p-value of analysis against T |  |  | 0.6064 | 0.6964 | 0.5209 |  |
| p-value of analysis against Placebo |  | 0.1014 | 0.2614 | 0.0411* | 0.0224* | 0.1601 |
| Hour 3 |  |  |  |  |  |  |
| N | 51 | 50 | 50 | 52 | 51 |  |
| Mean | −0.27 | −0.06 | −0.06 | 0.04 | 0.16 |  |
| SD | 0.80 | 0.84 | 0.93 | 0.84 | 0.86 |  |
| Median | 0 | 0 | 0 | 0 | 0 |  |
| Range | −1–2 | −1–2 | −1–3 | −1–2 | −1–2 |  |
| p-value of analysis against T |  |  | 1.0000 | 0.5620 | 0.2042 |  |
| p-value of analysis against Placebo |  | 0.2092 | 0.2092 | 0.0648 | 0.0115* | 0.1387 |
| Hour 4 |  |  |  |  |  |  |
| N | 51 | 50 | 50 | 52 | 51 |  |
| Mean | −0.25 | 0.06 | −0.04 | 0.13 | 0.18 |  |
| SD | 0.82 | 0.91 | 0.97 | 0.93 | 0.91 |  |
| Median | 0 | 0 | 0 | 0 | 0 |  |
| Range | −1–2 | −1–2 | −1–3 | −1–2 | −1–2 |  |
| p-value of analysis against T |  |  | 0.5829 | 0.6790 | 0.5204 |  |
| p-value of analysis against Placebo |  | 0.0831 | 0.2362 | 0.0307* | 0.0173* | 0.1242 |
| Hour 5 |  |  |  |  |  |  |
| N | 51 | 50 | 50 | 52 | 51 |  |
| Mean | 0.27 | 0.00 | −0.06 | 0.15 | 0.22 |  |
| SD | 0.80 | 0.88 | 0.98 | 0.96 | 1.03 |  |
| Median | 0 | 0 | 0 | 0 | 0 |  |
| Range | −1–2 | −1–2 | −1–3 | −1–2 | −1–3 |  |
| p-value of analysis against T |  |  | 0.7479 | 0.4055 | 0.2461 |  |
| p-value of analysis against Placebo |  | 0.1402 | 0.2487 | 0.0205* | 0.0084* | 0.0707 |
| Hour 6 |  |  |  |  |  |  |
| N | 51 | 50 | 50 | 52 | 51 |  |
| Mean | −0.25 | 0.04 | −0.02 | 0.17 | 0.08 |  |
| SD | 0.82 | 0.95 | 1.06 | 0.96 | 0.87 |  |
| Median | 0 | 0 | 0 | 0 | 0 |  |
| Range | −1–2 | −1–2 | −1–3 | −1–2 | −1–2 |  |
| p-value of analysis against T |  |  | 0.7486 | 0.4731 | 0.8366 |  |
| p-value of analysis against Placebo |  | 0.1143 | 0.2080 | 0.0210* | 0.0731 | 0.1998 |
| Hour 7 |  |  |  |  |  |  |
| N | 51 | 50 | 50 | 52 | 51 |  |
| Mean | −0.24 | −0.02 | −0.06 | 0.21 | 0.08 |  |
| SD | 0.89 | 0.87 | 1.06 | 1.00 | 0.89 |  |
| Median | 0 | 0 | 0 | 0 | 0 |  |
| Range | −1–3 | −1–2 | −1–3 | −1–2 | −1–2 |  |
| p-value of analysis against T |  |  | 0.8322 | 0.2162 | 0.6003 |  |
| p-value of analysis against Placebo |  | 0.2523 | 0.3511 | 0.0169* | 0.0941 | 0.1770 |
| Hour 8 |  |  |  |  |  |  |
| N | 51 | 50 | 50 | 52 | 51 |  |
| Mean | −0.24 | 0.02 | −0.06 | 0.19 | 0.08 |  |
| SD | 0.89 | 0.94 | 1.06 | 0.99 | 0.89 |  |
| Median | 0 | 0 | 0 | 0 | 0 |  |
| Range | −1–3 | −1–2 | −1–3 | −1–2 | −1–2 |  |
| p-value of analysis against T[3] |  |  | 0.6754 | 0.3628 | 0.7586 |  |
| p-value of analysis against Placebo[2] |  | 0.1801 | 0.3569 | 0.0238* | 0.0981 | 0.2199 |

Pain Intensity Score: 0=None, 1=Mild, 2=Moderate, 3=Severe. The Pain Intensity Difference (PID) at each time point is calculated as the difference between the Pain Intensity Score at Hour 0 and the score at observation time.
[1]P-values comparing all 5 treatment groups and pairwise comparisons are determined using ANOVA. Reference: Appendix D14.1 and FIG. 3.1
*Significance is at 0.05 nominal level. Last Observation Carried Forward method is used to impute missing values for ITT population.

Figure 21:
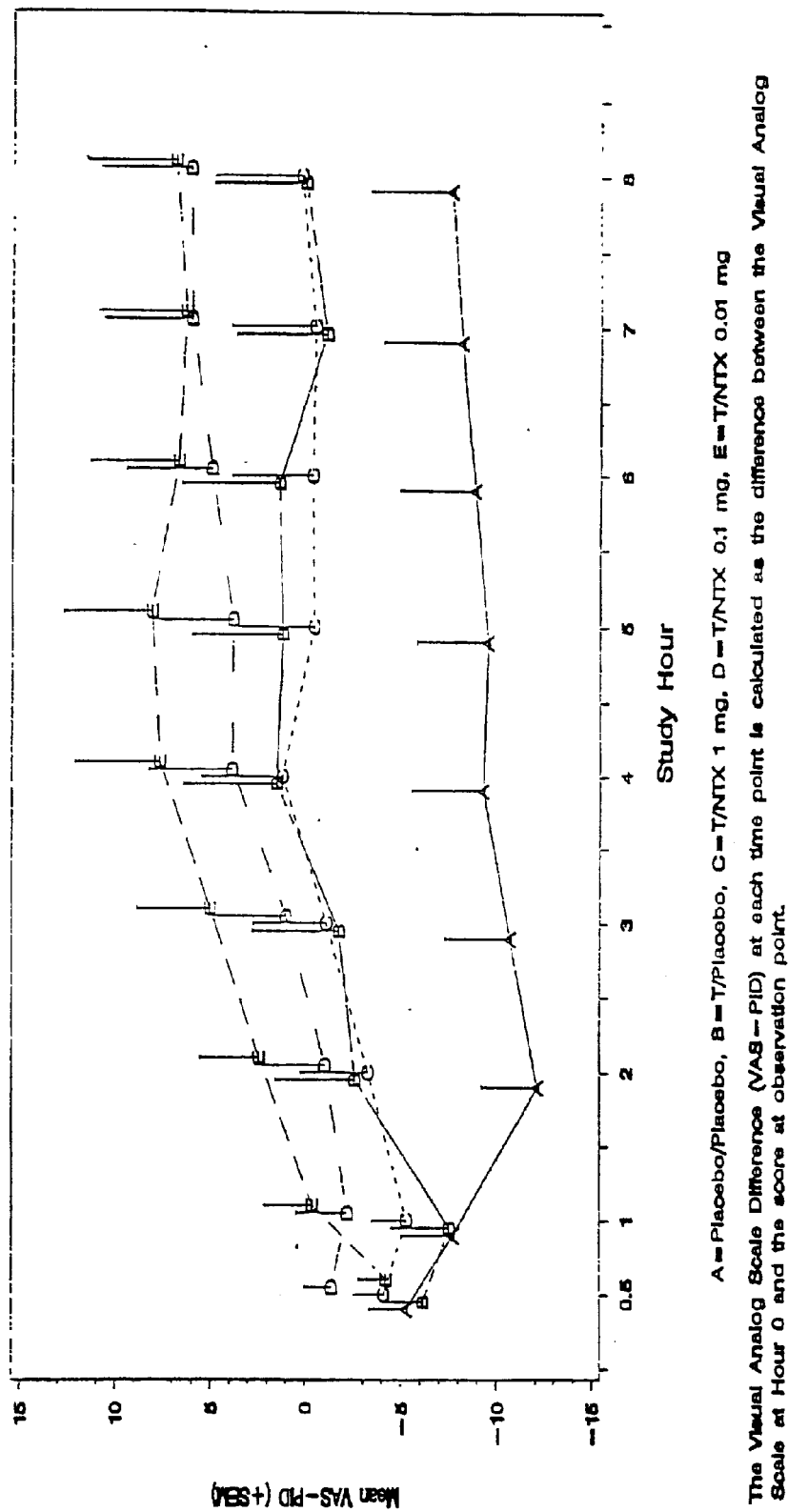
FIG. 21 represents hourly visual analog scale (VAS) pain intensity difference (PID) scores as presented in Table 12 where A–E represent the same groups as in FIG. 15.

Whereas the hourly VAS-PID scores for the placebo treatment were generally flat, those for the active treatment groups generally improved over time. The 4 active treatment groups separated from the placebo. FIG. 21 visually presents the hourly VAS-PID data presented in Table 12. At all time points, the VAS-PID scores of the 0.1-mg combination were higher than T alone.

TABLE 12

Summary and Analysis of Hourly Visual Analog-PID Scores
Intent-To-Treat Subjects

|  | Group 5 | Group 4 | Group 1 | Group 2 | Group 3 | |
| --- | --- | --- | --- | --- | --- | --- |
|  | | | Treatments | | | |
|  | Placebo with Placebo | T (50 mg) with Placebo | T (50 mg) with NTX (1 mg) | T (50 mg) with NTX (0.1 mg) | T (50 mg) with NTX (0.01 mg) | Overall P-value[2] |
| Number of Subjects | 51 | 50 | 50 | 52 | 51 | |
| Hour 0.5 | | | | | | |
| N | 51 | 50 | 50 | 52 | 51 | |
| Mean | −5.28 | −6.16 | −4.10 | −1.38 | −4.24 | |
| SD | 13.77 | 14.78 | 10.96 | 10.01 | 10.40 | |
| Median | −5 | −4 | −4 | −1 | −1 | |
| Range | −39~31 | −43~37 | −28~36 | −23~25 | −28~21 | |
| p-value of analysis against T[3] | | | 0.3960 | 0.0477* | 0.4254 | |
| p-value of analysis against Placebo[2] | | 0.7167 | 0.6266 | 0.1057 | 0.6651 | 0.3430 |
| Hour 1 | | | | | | |
| N | 51 | 50 | 50 | 52 | 51 | |
| Mean | −7.73 | −7.54 | −5.30 | −2.19 | −0.39 | |
| SD | 18.92 | 21.23 | 13.09 | 19.13 | 18.19 | |
| Median | −12 | −7 | −5 | −1 | 0 | |
| Range | −43~37 | −43~53 | −33~31 | −39~50 | −33~53 | |
| p-value of analysis against T[3] | | | 0.5416 | 0.1419 | 0.0511 | |
| p-value of analysis against Placebo[2] | | 0.9595 | 0.5066 | 0.1268 | 0.0444* | 0.1729 |
| Hour 2 | | | | | | |
| N | 51 | 50 | 50 | 52 | 51 | |
| Mean | −12.10 | −2.58 | −3.26 | −1.06 | 2.43 | |
| SD | 20.85 | 29.35 | 24.59 | 26.60 | 22.30 | |
| Median | −18 | −4 | −5 | −3 | 4 | |
| Range | −53~58 | −48~70 | −40~86 | −47~71 | −37~69 | |
| p-value of analysis against T[3] | | | 0.8916 | 0.7579 | 0.3131 | |
| p-value of analysis against Placebo[2] | | 0.0560 | 0.0759 | 0.0254* | 0.0035* | 0.0522 |
| Hour 3 | | | | | | |
| N | 51 | 50 | 50 | 52 | 51 | |
| Mean | −10.67 | −1.76 | −1.10 | 1.00 | 5.04 | |
| SD | 24.09 | 32.25 | 26.92 | 29.40 | 27.43 | |
| Median | −17 | −2 | −6 | −2 | 3 | |
| Range | −52~69 | −49~70 | −40~86 | −47~86 | −43~78 | |
| p-value of analysis against T[3] | | | 0.9067 | 0.6209 | .02259 | |
| p-value of analysis against Placebo[2] | | 0.1130 | 0.0889 | 0.0364* | 0.0052* | 0.0755 |
| Hour 4 | | | | | | |
| N | 51 | 50 | 50 | 52 | 51 | |
| Mean | −9.31 | 1.50 | 1.18 | 3.85 | 7.67 | |
| SD | 26.73 | 34.66 | 30.33 | 31.97 | 31.85 | |
| Median | −17 | −2 | −6 | −2 | 0 | |
| Range | −52~76 | −49~70 | −40~86 | −47~87 | −43~84 | |
| p-value of analysis against T[3] | | | 0.9592 | 0.7046 | 0.3217 | |
| p-value of analysis against Placebo[2] | | 0.0829 | 0.0924 | 0.0333* | 0.0064* | 0.0831 |
| Hour 5 | | | | | | |
| N | 51 | 50 | 50 | 52 | 51 | |
| Mean | −9.55 | 1.16 | −0.48 | 3.81 | 8.08 | |
| SD | 26.58 | 34.42 | 30.04 | 31.70 | 32.98 | |
| Median | −17 | −2 | −6 | −2 | 0 | |
| Range | −52~82 | −49~75 | −40~86 | −47~87 | −43~91 | |
| p-value of analysis against T[3] | | | 0.7932 | 0.6692 | 0.2671 | |
| p-value of analysis against Placebo[2] | | 0.0864 | 0.1461 | 0.0311* | 0.0048* | 0.0663 |
| Hour 6 | | | | | | |
| N | 51 | 50 | 50 | 52 | 51 | |
| Mean | −8.86 | 1.36 | −0.40 | 4.94 | 6.69 | |
| SD | 28.02 | 36.41 | 30.44 | 32.28 | 33.12 | |
| Median | −17 | −2 | −6 | −2 | −1 | |
| Range | −52~84 | −49~88 | −40~85 | −47~87 | −43~89 | |
| p-value of analysis against T[3] | | | 0.7846 | 0.5744 | 0.4062 | |
| p-value of analysis against Placebo[2] | | 0.1115 | 0.1874 | 0.0304* | 0.0153* | 0.1265 |

TABLE 12-continued

Summary and Analysis of Hourly Visual Analog-PID Scores
Intent-To-Treat Subjects

|  | Group 5 | Group 4 | Group 1 | Group 2 | Group 3 | |
| --- | --- | --- | --- | --- | --- | --- |
|  | Treatments | | | | | |
|  | Placebo with Placebo | T (50 mg) with Placebo | T (50 mg) with NTX (1 mg) | T (50 mg) with NTX (0.1 mg) | T (50 mg) with NTX (0.01 mg) | Overall P-value[2] |
| Hour 7 | | | | | | |
| N | 51 | 50 | 50 | 52 | 51 | |
| Mean | −8.18 | −1.10 | −0.50 | 6.04 | 6.31 | |
| SD | 29.22 | 33.82 | 31.17 | 33.06 | 33.02 | |
| Median | −17 | −2 | −7 | −2 | −1 | |
| Range | −52~83 | −49~70 | −40~86 | −47~87 | −43~84 | |
| p-value of analysis against T[3] | | | 0.9256 | 0.2627 | 0.2470 | |
| p-value of analysis against Placebo[2] | | 0.2691 | 0.2307 | 0.0255* | 0.0235* | 0.1335 |
| Hour 8 | | | | | | |
| N | 51 | 50 | 50 | 52 | 51 | |
| Mean | −7.63 | −0.02 | 0.22 | 6.10 | 6.88 | |
| SD | 30.40 | 34.69 | 32.65 | 34.10 | 33.64 | |
| Median | −17 | −2 | −7 | −2 | −1 | |
| Range | −52~83 | −49~76 | −40~86 | −47~87 | −43~81 | |
| p-value of analysis against T[3] | | | 0.9711 | 0.3523 | 0.2962 | |
| p-value of analysis against Placebo[2] | | 0.2497 | 0.2352 | 0.0366* | 0.0279* | 0.1771 |

The Visual Analog Scale Difference (VAS-PID) at each time point is calculated as the difference between the Visual Analog Scale at Hour 0 and the score at observation point.
[1]P-values comparing all 5 treatment groups and apirwise comparisons are determined using ANOVA. Reference: Appendix D3. 1
*Significance is at 0.05 nominal level. Last Observation Carried Forward method is used to impute missing values for ITT population.

Table 13 presents the summary and analysis of global evaluations. The placebo treatment had the highest number of subjects who had poor global evaluation scores based on subject evaluation. All 4 active treatment groups had comparable global evaluation scores.

The profiles of the global evaluations scores based on observer evaluation were similar to those based on subjects' evaluations. Analyses of global evaluations for the evaluable subgroup also yielded similar results.

TABLE 13

Summary and Analysis of Global Evaluations
Intent-To-Treat Subjects

|  | Group 5 | Group 4 | Group 1 | Group 2 | Group 3 | |
| --- | --- | --- | --- | --- | --- | --- |
|  | Treatments | | | | | |
|  | Placebo with Placebo | T (50 mg) with Placebo | T (50 mg) with NTX (1 mg) | T (50 mg) with NTX (0.1 mg) | T (50 mg) with NTX (0.01 mg) | Overall P-value[1] |
| Number of Subjects | 51 | 50 | 50 | 52 | 51 | |
| Subject Evaluation | | | | | | |
| Excellent | 1 (2.0%) | 1 (2.0%) | 3 (6.0%) | 2 (3.8%) | 3 (5.9%) | |
| Very Good | 1 (2.0%) | 6 (12.0%) | 5 (10.0%) | 6 (11.5%) | 9 (17.6%) | |
| Good | 3 (5.9%) | 4 (8.0%) | 5 (10.0%) | 10 (19.2%) | 5 (9.8%) | |
| Fair | 6 (11.8%) | 13 (26.0%) | 4 (8.0%) | 6 (11.5%) | 8 (15.7%) | |
| Poor | 40 (78.4%) | 26 (52.0%) | 33 (66.0%) | 28 (53.8%) | 26 (51.0%) | |
| P-value of analysis against T[2] | | | 0.4037 | 0.7481 | 0.5051 | |
| P-Value of analysis against Placebo | | 0.0060* | 0.0953 | 0.0042* | 0.0018* | 0.0165* |
| Observer Evaluation | | | | | | |
| Excellent | 1 (2.0%) | 2 (4.0%) | 3 (6.0%) | 5 (9.6%) | 5 (9.8%) | |
| Very Good | 5 (9.8%) | 5 (10.0%) | 4 (8.0%) | 8 (15.4%) | 8 (15.7%) | |
| Good | 1 (2.0%) | 5 (10.0%) | 5 (10.0%) | 5 (9.6%) | 5 (9.8%) | |
| Fair | 6 (11.8%) | 13 (26.0%) | 6 (12.0%) | 6 (11.5%) | 11 (21.6%) | |
| Poor | 38 (74.5%) | 25 (50.0%) | 32 (64.0%) | 28 (53.8%) | 22 (43.1%) | |
| P-value of analysis against T[2] | | | 0.3201 | 0.7139 | 0.2533 | |
| P-Value of analysis against Placebo | | 0.0211* | 0.2334 | 0.0180* | 0.0014* | 0.0176* |

[1]P-value comparing the treatment groups is determined using Kruskal-Wallis test. Reference: Appendix D10.1
[2]P-values of pairwise comparison are determined using Wilcoxon rank-sum test.
P-values are calculated based on non-missing observations.
*Significance is at 0.05 nominal level.

For the safety evaluation, no deaths were reported and there were no clinically serious adverse events.

Two hundred and nine subjects out of a total of 254 subjects reported 584 adverse events. Table 14 presents a summary and analysis of incidence of adverse events by treatment and MEDDRA body system. The majority of adverse events reported were categorized as gastrointestinal disorders (nausea or vomiting) as further shown in Table 15 or nervous system disorders (dizziness, headache or sedation). Eighty-five events were reported by the placebo group; 134 events were reported by the T alone group; 153, 116 and 96 events were reported by the T with NTX 1.0 mg, 0.1 mg, and 0.01 mg groups, respectively.

Table 16 presents a summary and analysis of incidence of adverse events by treatment; body system, and severity (mild (Table 16A), moderate (Table 16B) and severe (marked severity) (Table 16C)). Twenty-one events were considered by the investigator to be severe.

FIG. 22 represents a summary of exemplary adverse side effects attenuated according to methods and compositions of the invention.

TABLE 14

Incidence of Adverse Events by Treatment and MEDDRA Body System
Intent-To-Treat Subjects

| | Group 5 | Group 4 | Group 1 | Group 2 | Group 3 | |
| --- | --- | --- | --- | --- | --- | --- |
| | | | Treatments | | | |
| | Placebo with Placebo | T (50 mg) with Placebo | T (50 mg) with NTX (1 mg) | T (50 mg) with NTX (0.1 mg) | T (50 mg) with NTX (0.01 mg) | Overall P-value[1] |
| Number of Subjects | 51 | | 50 | 50 | 52 | 51 |
| Number (%) with Events | 39 (76%) | 40 (80%) | 45 (90%) | 41 (79%) | 44 (86%) | 0.3447 |
| Number of Events | 85 | 134 | 153 | 116 | 96 | |
| Gastrointestinal Disorders | 9 (17.6%) 14 | 20 (40.0%) 40 | 26 (52.0%) 55 | 19 (36.5%) 34 | 13 (25.5%) 24 | 0.0030* |
| Nausea | 9 (17.6%) 11 | 20 (40.0%) 28 | 24 (48.0%) 38 | 17 (32.7%) 22 | 11 (21.6%) 16 | 0.0050* |
| Vomiting Nos | 3 (3.0%) 3 | 10 (20.0%) 12 | 12 (24.0%) 17 | 8 (15.4%) 12 | 7 (13.7%) 8 | 0.0412* |
| Nervous System Disorders | 36 (70.6%) 70 | 40 (80.0%) 89 | 41 (82.0%) 94 | 36 (69.2%) 82 | 43 (84.3%) 71 | 0.2533 |
| Dizziness (Exc Vertigo) | 9 (17.6%) 10 | 15 (30.0%) 19 | 17 (34.0%) 25 | 12 (23.1%) 14 | 8 (15.7%) 8 | 0.1523 |
| Headache Nos | 27 (52.9%) 33 | 28 (56.0%) 38 | 29 (58.0%) 41 | 28 (53.8%) 38 | 26 (51.0%) 29 | 0.9628 |
| Sedation | 22 (43.1%) 27 | 28 (56.0%) 32 | 25 (50.0%) 28 | 22 (42.3%) 30 | 25 (49.0%) 33 | 0.6446 |
| Syncope | | | | | 1 (2.0%) 1 | 0.7953 |
| Skin & Subcutaneous Tissue Disorders | 1 (2.0%) 1 | 2 (4.0%) 2 | 3 (6.0%) 4 | | | 0.1049 |
| Pruritus Nos | 1(2.0%) 1 | 2(4.0%) 2 | 3(6.0%) 4 | | | 0.1049 |

'10 (26%) = frequency (percentage) occurrence'. Adverse Events are counted once per subject. Occurrence counts all events in that category.
[1]P-values of comparison among treatment groups are determined using Fisher's exact test.
*Significance is at 0.05 nominal level. Reference: Appendix D12

TABLE 15

Summary and Analysis of Incidence Nausea and Vomiting by Treatment
Intent-To-Treat Subjects

| | Group 5 | Group 4 | Group 1 | Group 2 | Group 3 | |
| --- | --- | --- | --- | --- | --- | --- |
| | | | Treatments | | | |
| | Placebo with Placebo | T (50 mg) with Placebo | T (50 mg) with NTX (1 mg) | T (50 mg) with NTX (0.1 mg) | T (50 mg) with NTX (0.01 mg) | Overall P-value[2] |
| Number of Subjects | 51 | 50 | 50 | 52 | 51 | |
| Nausea | | | | | | |
| Yes | 9 (17.6%) | 20 (40.0%) | 24 (48.0%) | 17 (32.7%) | 11 (21.6%) | |
| No | 42 (82.4%) | 30 (60.0%) | 26 (52.0%) | 35 (67.3%) | 40 (78.4%) | |
| p-value of analysis against T[3] | | 0.0161* | 0.5459 | 0.5375 | 0.0539 | |
| p-value of analysis against Placebo[2] | | | 0.0014* | 0.1119 | 0.8036 | 0.0050* |
| Vomiting Nos) | | | | | | |
| Yes | 2 (3.9%) | 10 (20.0%) | 12 (24.0%) | 8 (15.4%) | 7 (13.7%) | |
| No | 49 (96.1%) | 40 (80.0%) | 38 (76.0%) | 44 (84.6%) | 44 (86.3%) | |
| p-value of analysis against T[3] | | | 0.8097 | 0.6091 | 0.4366 | |
| p-value of analysis against Placebo[2] | | 0.0148* | 0.0039* | 0.0923 | 0.1599 | 0.0412* |

Nausea and vomiting are counted once per subject.
P-values of comparison among treatment groups and p-values of pairwise comparison are determined using Fisher's Exact test.
*Significance is at 0.05 nominal level. Reference: Appendix D16

TABLE 16A

Incidence of Adverse Events by Treatment, Body System and Severity
Intent-To-Treat Subjects Severity = Mild

|  | Group 5 | Group 4 | Group 1 | Group 2 | Group 3 |
|---|---|---|---|---|---|
|  |  |  | Treatments |  |  |
|  | Placebo with Placebo | T (50 mg) with Placebo | T (50 mg) with NTX (1 mg) | T (50 mg) with NTX (0.1 mg) | T (50 mg) with NTX (0.01 mg) |
| Number of Subjects | 51 | 50 | 50 | 52 | 51 |
| Number (%) with Events | 23 (45.1%) | 15 (30.0%) | 20 (40.0%) | 20 (38.5%) | 19 (37.3%) |
| Number of Events | 62 | 84 | 102 | 74 | 61 |
| Gastrointestinal Disorders | 6 (11.8%) 10 | 6 (12.0%) 15 | 14 (28.0%) 31 | 8 (15.4%) 16 | 4 (7.8%) 11 |
| Nausea | 8 (15.7%) 10 | 9 (18.0%) 14 | 16 (32.0%) 27 | 11 (21.2%) 15 | 6 (11.8%) 10 |
| Vomiting Nos | 0 (0.0%) 1 | 3 (6.0%) 4 | 1 (1.9%) 1 | 1 (2.0%) 1 |  |
| Nervous System Disorders | 21 (41.2%) 51 | 23 (46.0%) 66 | 22 (44.0%) 67 | 21 (40.4%) 58 | 24 (47.1%) 49 |
| Dizziness (Exc Vertigo) | 8 (15.7%) 9 | 12 (24.0%) 16 | 10 (20.0%) 15 | 6 (11.5%) 8 | 5 (9.8%) 5 |
| Headache Nos | 17 (33.3%) 23 | 17 (34.0%) 26 | 16 (32.0%) 27 | 19 (36.5%) 26 | 17 (33.3%) 20 |
| Sedation | 15 (29.4%) 19 | 21 (42.0%) 24 | 22 (44.0%) 25 | 17 (32.7%) 24 | 16 (31.4%) 24 |
| Syncope |  |  |  |  |  |
| Skin & Subcutaneous Tissue Disorders | 1 (2.0%) 1 | 2 (4.0%) 2 | 3 (6.0%) 4 |  |  |
| Pruritus Nos | 1 (2.0%) 1 | 2 (4.0%) 2 | 3 (6.0%) 4 |  |  |

'10 (26%) 23' = frequency (percentage) occurrence'.
Adverse Events are counted once per subject as the most severe report. Occurrence counts all events in that category.

TABLE 16B

Incidence of Adverse Events by Treatment, Body System and Severity
Intent-To-Treat Subjects Severity = Moderate

|  | Group 5 | Group 4 | Group 1 | Group 2 | Group 3 |
|---|---|---|---|---|---|
|  |  |  | Treatments |  |  |
|  | Placebo with Placebo | T (50 mg) with Placebo | T (50 mg) with NTX (1 mg) | T (50 mg) with NTX (0.1 mg) | T (50 mg) with NTX (0.01 mg) |
| Number of Subjects | 51 | 50 | 50 | 52 | 51 |
| Number (%) with Events | 14 (27.5%) | 22 (44.0%) | 19 (38.0%) | 17 (32.7%) | 24 (47.1%) |
| Number of Events | 21 | 47 | 42 | 36 | 34 |
| Gastrointestinal Disorders | 2 (3.9%) 3 | 12 (24.0%) 23 | 10 (20.0%) 22 | 10 (19.2%) 17 | 9 (17.6%) 13 |
| Nausea | 1 (2.0%) 1 | 10 (20.0%) 13 | 6 (12.0%) 9 | 5 (9.6%) 6 | 5 (9.8%) 6 |
| Vomiting Nos | 1 (2.0%) 2 | 9 (18.0%) 10 | 9 (18.0%) 13 | 7 (13.5%) 11 | 6 (11.8%) 7 |
| Nervous System Disorders | 14 (27.5%) 18 | 16 (32.0%) 22 | 13 (26.0%) 20 | 11 (21.2%) 19 | 18 (35.3%) 21 |
| Dizziness (Exc Vertigo) | 1 (2.0%) 1 | 3 (6.0%) 3 | 5 (10.0%) 8 | 5 (9.6%) 5 | 3 (5.9%) 3 |
| Headache Nos | 9 (17.6%) 9 | 10 (20.0%) 11 | 9 (18.0%) 10 | 6 (11.5%) 9 | 8 (15.7%) 8 |
| Sedation | 7 (13.7%) 8 | 7 (14.0%) 8 | 2 (4.0%) 2 | 4 (7.7%) 5 | 9 (17.6%) 9 |
| Syncope |  |  |  |  | 1 (2.0%) 1 |
| Skin & Subcutaneous Tissue Disorders |  |  |  |  |  |
| Pruritus Nos |  |  |  |  |  |

'10 (26%) 23' = frequency (percentage) occurrence'.
Adverse Events are counted once per subject as the most severe report. Occurrence counts all events in that category.

TABLE 16C

Incidence of Adverse Events by Treatment, Body System and Severity
Intent-To-Treat Subjects Severity = Severe

|  | Group 5 | Group 4 | Group 1 | Group 2 | Group 3 |
|---|---|---|---|---|---|
|  |  |  | Treatments |  |  |
|  | Placebo with Placebo | T (50 mg) with Placebo | T (50 mg) with NTX (1 mg) | T (50 mg) with NTX (0.1 mg) | T (50 mg) with NTX (0.01 mg) |
| Number of Subjects | 51 | 50 | 50 | 52 | 51 |
| Number (%) with Events | 2 (3.9%) | 3 (6.0%) | 6 (12.0%) | 4 (7.7%) | 1 (2.0%) |
| Number of Events | 2 | 3 | 9 | 6 | 1 |
| Gastrointestinal Disorders | 1 (2.0%) 1 | 2 (4.0%) 2 | 2 (4.0%) 2 | 1 (1.9%) 1 |  |

TABLE 16C-continued

Incidence of Adverse Events by Treatment, Body System and Severity
Intent-To-Treat Subjects Severity = Severe

| | Group 5 | Group 4 | Group 1 | Group 2 | Group 3 |
|---|---|---|---|---|---|
| | | | Treatments | | |
| | Placebo with Placebo | T (50 mg) with Placebo | T (50 mg) with NTX (1 mg) | T (50 mg) with NTX (0.1 mg) | T (50 mg) with NTX (0.01 mg) |
| Nausea | 1 (2.0%) 1 | 2 (4.0%) 2 | 1 (1.9%) 1 | | |
| Vomiting Nos | 1 (2.0%) 1 | 1 (2.0%) 1 | | | |
| Nervous System Disorders | 1 (2.0%) 1 | 1 (2.0%) 1 | 6 (12.0%) 7 | 4 (7.7%) 5 | 1 (2.0%) 1 |
| Dizziness (Exc Vertigo) | | | 2 (4.0%) 2 | 1 (1.9%) 1 | |
| Headache Nos | 1 (2.0%) 1 | 1 (2.0%) 1 | 4 (8.0%) 4 | 3 (5.8%) 3 | 1 (2.0%) 1 |
| Sedation | | | 1 (2.0%) 1 | 1 (1.9%) 1 | |
| Syncope | | | | | |
| Skin & Subcutaneous Tissue Disorders | | | | | |
| Pruritus Nos | | | | | |

'10 (26%) 23' = frequency (percentage) occurrence'.
Adverse Events are counted once per subject as the most severe report. Occurrence counts all events in that category.

Although the invention herein has been described with reference to particular embodiments, it is to be understood that these embodiments are merely illustrative of various aspects of the invention. Thus, it is to be understood that numerous modifications may be made in the illustrative embodiments and other arrangements may be devised without departing from the spirit and scope of the invention.

What is claimed is:

1. A method for selectively enhancing the analgesic potency of tramadol and simultaneously attenuating anti-analgesia, hyperalgesia, hyperexcitability, physical dependence and/or tolerance effects associated with the administration of tramadol to a human subject, said method comprising administering to a human subject an analgesic or sub-analgesic amount of tramadol and an amount of an excitatory opioid receptor antagonist effective to enhance the analgesic potency of tramadol and the anti-analgesia, hyperalgesia, hyperexcitability, physical dependence and/or tolerance effects of tramadol.

2. The method of claim 1 wherein the excitatory opioid receptor antagonist is selected from the group consisting of naltrexone, naloxone, nalmefene, etorphine, dihydroetorphine and similarly acting opioid alkaloids and opioid peptides.

3. The method of claim 1 wherein the excitatory opioid receptor antagonist is naltrexone.

4. The method of claim 1 wherein the excitatory opioid receptor antagonist is naloxone.

5. The method of claim 1 wherein the excitatory opioid receptor antagonist is nalmefene.

6. The method of claim 1 wherein the amount of antagonist administered is 1000–10,000,000 fold less than the amount of tramadol administered.

7. The method of claim 1 wherein the amount of antagonist administered is 10,000–1,000,000 fold less than the amount of tramadol administered.

8. The method of claim 1 wherein the mode of administration is selected from the group consisting of oral, sublingual, intramuscular, subcutaneous, intravenous and transdermal.

9. A method for treating pain in a human subject comprising administering to the human subject an analgesic or sub-analgesic amount of tramadol and an amount of an excitatory opioid receptor antagonist effective to enhance the analgesic potency of tramadol and attenuate anti-analgesia, hyperalgesia, hyperexcitability, physical dependence and/or tolerance effects of tramadol.

10. The method of claim 9 wherein the excitatory opioid receptor antagonist is selected from the group consisting of naltrexone, naloxone, nalmefene, etorphine, dihydroetorphine and similarly acting opioid alkaloids and opioid peptides.

11. The method of claim 9 wherein the excitatory opioid receptor antagonist is naltrexone.

12. The method of claim 9 wherein the excitatory opioid receptor antagonist is naloxone.

13. The method of claim 9 wherein the excitatory opioid receptor antagonist is nalmefene.

14. The method of claim 9 wherein the amount of the antagonist administered is 1000–10,000,000 fold less than the amount of tramadol administered.

15. The method of claim 9 wherein the amount of the antagonist administered is 10,000–1,000,000 fold less than the amount of tramadol administered.

16. The method of claim 9 wherein the mode of administration is selected from the group consisting of oral, sublingual, intramuscular, subcutaneous, intravenous and transdermal.

17. A composition comprising an analgesic or sub-analgesic amount of tramadol and an amount of an excitatory opioid receptor antagonist effective to enhance the analgesic potency of tramadol and attenuate the anti-analgesia, hyperalgesia, hyperexcitability, physical dependence and/or tolerance effects of tramadol in a human subject administered the composition.

18. The composition of claim 17 wherein the excitatory opioid receptor antagonist is selected from the group consisting of naltrexone, naloxone, nalmefene, etorphine, dihydroetorphine and similarly acting opioid alkaloids and opioid peptides.

19. The composition of claim 17 wherein the excitatory opioid receptor antagonist is naltrexone.

20. The composition of claim 17 wherein the excitatory opioid receptor antagonist is naloxone.

21. The composition of claim 17 wherein the excitatory opioid receptor antagonist is nalmefene.

22. The composition of claim 17 wherein the amount of the antagonist is 1000–10,000,000 fold less than the amount of tramadol.

23. The composition of claim 17 wherein the amount of the antagonist is 10,000–1,000,000 fold less than the amount of tramadol.

24. A method for enhancing the potency of tramadol in a human subject comprising administering to the human subject an analgesic or subanalgesic amount of tramadol and an amount of an opioid antagonist effective to enhance the analgesic potency of tramadol.

25. The method of claim 24 wherein the opioid antagonist is naltrexone, naloxone, or nalmefene.

26. The method of claim 24 wherein the opioid antagonist is naltrexone.

27. The method of claim 24 wherein the opioid antagonist is nalmefene.

28. The method of claim 24 wherein the administration is oral, sublingual, intramuscular, subcutaneous, intravenous or transdermal.

29. The method of claim 24 wherein the administration is oral.

30. A method for attenuating an adverse side effect associated with administration of tramadol to a human subject comprising administering to the human subject an analgesic or subanalgesic amount of tramadol and an amount of an opioid antagonist effective to attenuate the adverse side effect.

31. The method of claim 30 wherein the adverse side effect is nausea, vomiting, dizziness, headache, sedation or pruritis.

32. The method of claim 30 wherein the opioid antagonist is naltrexone, naloxone, or nalmefene.

33. The method of claim 30 wherein the opioid antagonist is naltrexone.

34. The method of claim 30 wherein the opioid antagonist is nalmefene.

35. The method of claim 30 wherein the administration is oral, sublingual, intramuscular, subcutaneous, intravenous and transdermal.

36. The method of claim 30 wherein the administration is oral.

37. A method for enhancing the potency of tramadol and attenuating an adverse side effect associated with administration of tramadol to a human subject comprising administering to the human subject an analgesic or subanalgesic amount of tramadol and an amount of an opioid antagonist effective to enhance the analgesic potency of tramadol and attenuate the adverse side effect.

38. The method of claim 37 wherein the adverse side effect is nausea, vomiting, dizziness, headache, sedation or pruritis.

39. The method claim 37 wherein the opioid antagonist is naltrexone, naloxone, or nalmefene.

40. The method of claim 37 wherein the opioid antagonist is naltrexone.

41. The method of claim 37 wherein the opioid antagonist is nalmefene.

42. The method of claim 37 wherein the administration is oral, sublingual, intramuscular, subcutaneous, intravenous and transdermal.

43. The method of claim 37 wherein the administration is oral.

44. A method for treating pain in a human subject comprising administering to the human subject an analgesic or subanalgesic amount of tramadol and an amount of an opioid antagonist effective to enhance the analgesic potency of tramadol.

45. The method claim 44 wherein the opioid antagonist is naltrexone, naloxone, or nalmefene.

46. The method of claim 44 wherein the opioid antagonist is naltrexone.

47. The method of claim 44 wherein the opioid antagonist is nalmefene.

48. The method of claim 44 wherein the administration is oral, sublingual, intramuscular, subcutaneous, intravenous or transdermal.

49. The method of claim 44 wherein the administration is oral.

50. A method for treating pain with tramadol and attenuating an adverse side effect of tramadol in a human subject comprising administering to the human subject an analgesic or subanalgesic amount of tramadol and an amount of an opioid antagonist effective to enhance the analgesic potency of tramadol and attenuate the adverse side effect.

51. The method of claim 50 wherein the adverse side effect is nausea, vomiting, dizziness, headache, sedation or pruritis.

52. The method claim 50 wherein the opioid antagonist is naltrexone, naloxone, or nalmefene.

53. The method of claim 50 wherein the opioid antagonist is naltrexone.

54. The method of claim 50 wherein the opioid antagonist is nalmefene.

55. The method of claim 50 wherein the administration is oral, sublingual, intramuscular, subcutaneous, intravenous or transdermal.

56. The method of claim 50 wherein the administration is oral.

57. A composition comprising an analgesic or subanalgesic amount of tramadol and an amount of an opioid antagonist effective to enhance the analgesic potency of tramadol in a human subject.

58. The composition of claim 57 wherein the opioid antagonist is naltrexone, naloxone, or nalmefene.

59. The composition of claim 57 wherein the opioid antagonist is naltrexone.

60. The composition of claim 57 wherein the opioid antagonist is nalmefene.

61. The composition of claim 57 wherein the administration is oral, sublingual, intramuscular, subcutaneous, intravenous or transdermal.

62. The composition of claim 57 wherein the administration is oral.

63. A composition comprising an analgesic or subanalgesic amount of tramadol and an amount of an opioid antagonist effective to attenuate an adverse side effect of tramadol in a human subject.

64. The composition of claim 63 wherein the adverse side effect is nausea, vomiting, dizziness, headache, sedation or pruritis.

65. The composition of claim 63 wherein the opioid antagonist is naltrexone, naloxone, or nalmefene.

66. The composition of claim 63 wherein the opioid antagonist is naltrexone.

67. The composition of claim 63 wherein the opioid antagonist is nalmefene.

68. The composition of claim 63 wherein the administration is oral, sublingual, intramuscular, subcutaneous, intravenous or transdermal.

69. The composition of claim 63 wherein the administration is oral.

70. A composition comprising an analgesic or subanalgesic amount of tramadol and an amount of an opioid antagonist effective to enhance the analgesic potency of tramadol and attenuate an adverse side effect of tramadol in a human subject.

71. The composition of claim 70 wherein the adverse side effect is nausea, vomiting, dizziness, headache, sedation or pruritis.

72. The composition of claim 70 wherein the opioid antagonist is naltrexone, naloxone, or nalmefene.

73. The composition of claim 70 wherein the opioid antagonist is naltrexone.

74. The composition of claim 70 wherein the opioid antagonist is nalmefene.

75. The composition of claim 70 wherein the administration is oral, sublingual, intramuscular, subcutaneous, intravenous or transdermal.

76. The composition of claim 70 wherein the administration is oral.

* * * * *